United States Patent
Fu et al.

(10) Patent No.: US 9,815,804 B2
(45) Date of Patent: *Nov. 14, 2017

(54) ISOXAZOLE HYDROXAMIC ACID COMPOUNDS AS LPXC INHIBITORS

(71) Applicant: Novartis AG, Basel (CH)

(72) Inventors: Jiping Fu, Danville, CA (US); Xianming Jin, San Ramon, CA (US); Subramanian Karur, Dublin, CA (US); Guillaume Lapointe, San Francisco, CA (US); Ann Marie Madera, Dublin, CA (US); Zachary Kevin Sweeney, Redwood City, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/375,560

(22) Filed: Dec. 12, 2016

(65) Prior Publication Data

US 2017/0088525 A1  Mar. 30, 2017

Related U.S. Application Data

(63) Continuation of application No. 14/969,930, filed on Dec. 15, 2015, now Pat. No. 9,549,916.

(60) Provisional application No. 62/092,402, filed on Dec. 16, 2014.

(51) Int. Cl.
| | |
|---|---|
| C07D 261/08 | (2006.01) |
| A61K 31/42 | (2006.01) |
| A61K 45/06 | (2006.01) |
| C07D 413/12 | (2006.01) |
| A61K 31/422 | (2006.01) |
| C07D 413/06 | (2006.01) |

(52) U.S. Cl.
CPC ........... *C07D 261/08* (2013.01); *A61K 31/42* (2013.01); *A61K 31/422* (2013.01); *A61K 45/06* (2013.01); *C07D 413/06* (2013.01); *C07D 413/12* (2013.01)

(58) Field of Classification Search
None
See application file for complete search history.

(56) References Cited

U.S. PATENT DOCUMENTS 8,748,466 B2 * 6/2014 Abramite ............. C07D 261/08
514/378
8,809,333 B2    8/2014 Brown

FOREIGN PATENT DOCUMENTS

| EP | 418667 | 9/1990 |
|---|---|---|
| WO | 2004/062601 | 7/2004 |
| WO | 2006/082404 | 8/2006 |
| WO | 2010/032147 | 3/2010 |
| WO | 2011/073845 | 6/2011 |
| WO | 2012/137099 | 10/2011 |
| WO | 2012/032014 | 3/2012 |
| WO | 2012/120397 | 9/2012 |
| WO | 2012/137094 | 10/2012 |
| WO | 2012/154204 | 11/2012 |
| WO | 2014/160649 | 10/2014 |

OTHER PUBLICATIONS

McAllister et al., "Heterocyclic Methylsulfone Hydroxamic Acid LpxC Inhibitors as Gram-Negative Antibacterial Agents" Bioorganic & Medicinal Chemistry Letters 22:6832-6838, 2012.

Grazia Piizzi, "Design, Synthesis and Properties of Potent Inhibitors of Pseudomonas Aeruginosa Deacetylase LpxC" Global Discovery Chemistry Novartis AG, Switzerland EFMC Meeting, Lisbon, Sep. 9, 2014.

* cited by examiner

Primary Examiner — Kamal Saeed
(74) Attorney, Agent, or Firm — Mark H. Hopkins

(57) ABSTRACT

This invention pertains generally to compounds of Formula I as described herein and compositions containing such compounds, as well as methods of using such compounds to treat bacterial infections. In certain aspects, the invention provides methods and compositions comprising these compounds for treating infections caused by Gram-negative bacteria.

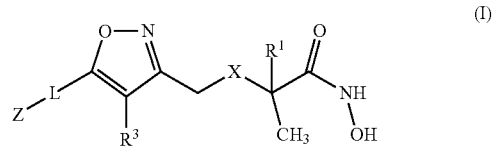

(I)

19 Claims, No Drawings

ISOXAZOLE HYDROXAMIC ACID COMPOUNDS AS LPXC INHIBITORS

RELATED APPLICATIONS

This application is a continuation of U.S. Ser. No. 14/969,930, filed 15 Dec. 2015, which claims benefit of priority from U.S. Provisional Application Ser. No. 62/092,402, filed on 16 Dec. 2014; the contents of which are incorporated herein by reference in their entirety.

FIELD OF THE INVENTION

This invention pertains generally to compounds and compositions and methods for treating bacterial infections. In certain aspects, the invention pertains to treating infections caused by Gram-negative bacteria. More particularly, the invention pertains to treating Gram-negative infections using compounds disclosed herein. Without being bound by theory, the compounds are believed to act by inhibiting the activity of UDP-3-O—(R-3-hydroxydecanoyl)-N-acetylglucosamine deacetylase (LpxC). The invention includes compounds of Formula (I) which inhibit LpxC, pharmaceutical formulations containing such inhibitors, methods of treating patients with such compounds and pharmaceutical formulations, and methods of preparing such pharmaceutical formulations and inhibitors. The inhibitors can be used to treat bacterial infections, especially Gram-negative infections in subjects, including humans. These compounds may be used alone or in combination with other antibacterials.

BACKGROUND

Over the past several decades, the frequency of antimicrobial resistance and its association with serious infectious diseases have increased at alarming rates. The increasing prevalence of pathogens resistant to one or more of the approved antibiotics for treating agents causing nosocomial infections, also called hospital-acquired infections, is particularly disconcerting. Of the over 2 million nosocomial infections occurring each year in the United States, 50 to 60% are caused by antimicrobial-resistant strains of bacteria. The high rate of resistance to commonly-used antibacterial agents increases the morbidity, mortality, and costs associated with nosocomial infections. In the United States, nosocomial infections are thought to contribute to or cause more than 77,000 deaths per year and cost approximately $5 to $10 billion annually. Only a few classes of approved antibacterials are effective on Gram-negative bacteria. Important causes of Gram-negative resistance include extended-spectrum β-lactamases (ESBLs) in *Klebsiella pneumoniae, Escherichia coli*, and *Proteus mirabilis*, high-level third-generation cephalosporin (Amp C) β-lactamase resistance among *Enterobacter* species and *Citrobacter freundii*, and multidrug-resistance genes observed in *Pseudomonas* species, *Acinetobacter* species, and *Stenotrophomonas* species.

The problem of antibacterial resistance is compounded by the existence of bacterial strains resistant to multiple families of antibacterials. For example, *Pseudomonas aeruginosa* isolates resistant to fluoroquinolones are virtually all resistant to additional antibacterial medicines as well. Much of the antibacterial discovery effort in the pharmaceutical industry is aimed at the development of drugs effective against Gram-positive bacteria. However, there is also a need for new Gram-negative antibacterials, which are in general more resistant to a large number of antibacterials and chemotherapeutic agents than are Gram-positive bacteria. Such antibacterial compounds acting on lipopolysaccharide biosynthesis have been reported, including various hydroxamic acid compounds: see for example WO2004/062601, WO2010/032147, WO2011/073845, WO2012/120397, and WO2012/137094. One lipopolysaccharide biosynthesis enzyme, UDP-3-O—(R-3-hydroxydecanoyl)-N-acetylglucosamine deacetylase (LpxC), has been reported as a validated target for antibacterials (Mdluli, et al., *Antimicrobial Agents and Chemotherapy*, 50(6), 2178-84 (2006). While inhibitors of LpxC have been described, there remains a need for new LpxC inhibitors. The current invention provides new antibacterial hydroxamic acid compounds that are believed to act by inhibition of LpxC and that avoid at least some of the prevalent mechanisms of resistance to known antibacterial agents.

BRIEF SUMMARY

The present invention provides novel compounds, pharmaceutical formulations including the compounds, and methods of inhibiting UDP-3-O—(R-3-hydroxydecanoyl)-N-acetylglucosamine deacetylase (LpxC) and treating Gram-negative bacterial infections using those novel compounds.

In one aspect, the invention provides compounds of Formula (I)

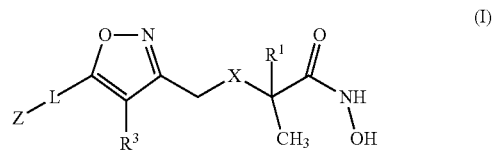

or a pharmaceutically acceptable salt thereof, wherein:
X is —NH—, and $R^1$ is —CH(OH)—Y;
or
X is —CH$_2$—, and $R^1$ is —CH(OH)—Y or —SO$_2R^2$ where $R^2$ is $C_1$-$C_3$ alkyl;
$R^3$ is H or halo;
Y is selected from a 5-membered heteroaryl ring containing 1-3 heteroatoms selected from N, O and S as ring members, phenyl, and $C_{1-3}$ alkyl, and each Y is optionally substituted with one to three $R^4$;
each $R^4$ is independently selected from halo, $C_{1-3}$ alkyl, and $C_{3-6}$ cycloalkyl, wherein the $C_{1-3}$ alkyl and $C_{3-6}$ cycloalkyl are each optionally substituted with up to three groups selected from halo, CN and —OH;
L is —C≡C— or —CR$^5$=CR$^5$—;
$R^5$ is independently selected at each occurrence from H, halo and methyl;
and
Z is selected from $C_{1-6}$ alkyl, $C_3$-$C_6$ cycloalkyl, pyridinyl, and phenyl, each of which is optionally substituted with up to three groups selected from halogen, hydroxy, $C_{1-4}$ alkoxy, $C_{1-4}$ haloalkoxy, CN, and $C_{1-4}$ alkyl that is optionally substituted with one to three groups selected from halogen, hydroxy, amino, CN, and $C_{1-3}$ alkoxy;
or, when L is —CR$^5$=CR$^5$—, Z taken together with one of the $R^5$ groups and any atoms between Z and the $R^5$ group can form a 3-7 membered cycloalkyl or cycloalkenyl group that is optionally substituted with up to three groups selected from halogen, hydroxy, $C_{1-4}$ alkoxy, $C_{1-4}$ haloalkoxy, CN, and $C_{1-4}$ alkyl that is optionally substituted with one to three groups selected from halogen, hydroxy, amino, CN, and $C_{1-3}$ alkoxy. Various embodiments of these compounds are described further herein.

In one aspect, the invention provides a method of inhibiting a deacetylase enzyme in Gram-negative bacteria, thereby affecting bacterial growth, comprising contacting the bacteria with a compound of formula I. In this and the following summary of aspects and embodiments of the invention, compounds of Formula I include any of the subsets or specific examples of such compounds that are disclosed herein.

In another aspect, the invention provides a method of inhibiting LpxC, thereby modulating the virulence of a bacterial infection, comprising administering to a patient in need of such inhibition (or in need of treatment for such bacterial infection) a compound of Formula I.

In another aspect, the invention provides a method for treating a subject with a Gram-negative bacterial infection, wherein the method comprises administering to the subject an antibacterially effective amount of a compound of formula I; optionally, the compound may be combined with a pharmaceutically acceptable carrier for such administration. In certain embodiments, the subject is a mammal and in some embodiments, the subject is a human. Gram-negative bacterial infections suitable for treatment with the compounds and compositions of the invention are disclosed herein.

In another aspect, the invention provides a method of administering an inhibitory amount of a compound of formula I to fermentative or non-fermentative Gram-negative bacteria, which can be carried out in vivo, e.g. in a subject infected with the Gram-negative bacteria, or in vitro, e.g. in cell culture. In certain embodiments of the method of administering an inhibitory amount of a compound of formula I to fermentative or non-fermentative Gram-negative bacteria, the Gram-negative bacteria are selected from the group consisting of *Pseudomonas aeruginosa* and other *Pseudomonas* spp., *Stenotrophomonas maltophilia*, *Burkholderia cepacia* and other *Burkholderia* spp., *Alcaligenes xylosoxidans*, *Acinetobacter* spp., *Achromobacter* spp., *Aeromonas* spp., *Enterobacter* spp., *Eschericia coli*, *Haemophilus* spp., *Klebsiella* spp., *Moraxella* spp., *Bacteroides* spp., *Francisella* spp., *Shigella* spp., *Proteus* spp., *Porphyromonas* spp., *Prevotella* spp., *Mannheimia haemolyiticus*, *Pastuerella* spp., *Providencia* spp., *Vibrio* spp., *Salmonella* spp., *Bordetella* spp., *Borrelia* spp., *Helicobacter* spp., *Legionella* spp., *Citrobacter* spp., *Cedecea* spp., *Serratia* spp., *Campylobacter* spp., *Yersinia* spp., *Fusobacterium* spp., and *Neisseria* spp.

In another embodiment, the invention provides a method of administering an inhibitory amount of a compound of formula I to Gram-negative bacteria, such as members from the Pseudomonadales and Enterobacteriaceae species which is selected from the group consisting of organisms such as *Pseudomonas, Acinetobacter, Stenotrophomonas, Burkholderia, Serratia, Proteus, Klebsiella, Enterobacter, Citrobacter, Salmonella, Shigella, Providencia, Morganella, Cedecea, Yersina* and *Edwardsiella* species and *Escherichia coli*.

Another embodiment of the invention provides a pharmaceutical composition comprising a compound of Formula I admixed with a pharmaceutically acceptable carrier or excipient. Optionally, the pharmaceutical composition may comprise at least two pharmaceutically acceptable carriers and/or excipients. In certain embodiments, the pharmaceutical composition is prepared for administration in the form of a unit dosage that contains a therapeutically effective amount of a compound of Formula I for treatment of a subject having a Gram-negative bacterial infection. Typically, the unit dosage is in a form suitable for injection, infusion, inhalation or oral delivery.

Pharmaceutical formulations according to the present invention are provided which include any of the compounds described above and a pharmaceutically acceptable carrier. In certain of these embodiments, the pharmaceutical composition comprises two or more pharmaceutically acceptable carriers and/or excipients.

The invention also provides for the use of the compounds of Formula I in preparing medicaments and pharmaceutical formulations, for use of the compounds in inhibiting LpxC, and for use of the compounds as medicaments, especially for treating bacterial infections in a subject.

The present invention is also directed to methods of combination therapy for treating or preventing a Gram-negative bacterial infection in patients, using the compounds of the invention or pharmaceutical compositions thereof, or kits containing these compounds or pharmaceutical compositions, in combination with at least one other therapeutic agent. Other aspects of the invention are discussed infra.

DETAILED DESCRIPTION

For purposes of interpreting this specification, the following definitions will apply, and whenever appropriate, terms used in the singular will also include the plural.

Terms used in the specification have the following meanings unless the context clearly indicates otherwise:

"LpxC" is an abbreviation that stands for UDP-3-O—(R-3-hydroxydecanoyl)-N-acetylglucosamine deacetylase. While not limited by the theory, it is believed that the compounds of the invention provide their antibacterial effect primarily by inhibiting LpxC.

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "antibacterial agent" refers to agents synthesized or modified in the laboratory that have either bactericidal or bacteriostatic activity. An "active" agent in this context will inhibit the growth of P. aeruginosa and/or other Gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population is even eliminated. If an enzyme activity assay is used to screen for inhibitors, one can make modifications in bacterial uptake/efflux, solubility, half-life, etc. to compounds in order to correlate enzyme inhibition with growth inhibition.

"Optionally substituted" means the group referred to can be substituted at one or more positions by any one or any combination of the radicals suitable for substitution on that group. The number, placement and selection of substituents is understood to encompass only those substitutions that a skilled chemist would expect to be reasonably stable; thus 'oxo' would not be a substituent on an aryl or heteroaryl ring, for example, and a single carbon atom would not have three hydroxy or amino substituents.

"Halo" or "halogen", as used herein, may be fluorine, chlorine, bromine or iodine.

"$C_1$-$C_6$ alkyl", or "$C_{1-6}$ alkyl" as used herein, denotes straight chain or branched alkyl having 1-6 carbon atoms. If a different number of carbon atoms is specified, such as $C_4$ or $C_3$, then the definition is to be amended accordingly, such as "$C_1$-$C_4$ alkyl" will represent methyl, ethyl, propyl, isopropyl, butyl, isobutyl, sec-butyl and tert-butyl.

"$C_1$-$C_6$ alkoxy", or "$C_{1-6}$ alkoxy" as used herein, denotes straight chain or branched alkoxy having 1-6 carbon atoms. If a different number of carbon atoms is specified, such as $C_4$ or $C_3$, then the definition is to be amended accordingly, such as "$C_1$-$C_4$ alkoxy" will represent methoxy, ethoxy, propoxy, isopropoxy, butoxy, isobutoxy, sec-butoxy and tert-butoxy.

"$C_1$-$C_4$ haloalkyl" or "$C_{1-4}$ haloalkyl" as used herein, denotes straight chain or branched alkyl having 1-4 carbon atoms wherein at least one hydrogen has been replaced with a halogen. The number of halogen replacements can be from one up to the number of hydrogen atoms on the unsubstituted alkyl group. If a different number of carbon atoms is specified, such as $C_6$ or $C_3$, then the definition is to be amended accordingly. Thus "$C_1$-$C_4$ haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_3$-$C_8$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be amended accordingly.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings; unless otherwise specified, such rings contain 1 to 7, 1 to 5, or 1 to 3 heteroatoms selected from the group consisting of nitrogen, oxygen and sulphur as ring members, and the rings may be saturated, or partially saturated but not aromatic. The heterocyclic group can be attached at a heteroatom or a carbon atom. The term "heterocyclyl" includes single ring groups, fused ring groups and bridged groups. Examples of such heterocyclyl include, but are not limited to pyrrolidine, piperidine, piperazine, pyrrolidine, pyrrolidinone, morpholine, tetrahydrofuran, tetrahydrothiophene, tetrahydrothiopyran, tetrahydropyran, 1,4-dioxane, 1,4-oxathiane, 8-aza-bicyclo[3.2.1]octane, 3,8-diazabicyclo[3.2.1]octane, 3-Oxa-8-aza-bicyclo[3.2.1]octane, 8-Oxa-3-aza-bicyclo[3.2.1] octane, 2-Oxa-5-aza-bicyclo[2.2.1]heptane, 2,5-Diaza-bicyclo[2.2.1]heptane, azetidine, ethylenedioxo, oxetane or thiazole.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring or ring system (e.g., 5-7 membered monocyclic group or an 8-10 membered bicyclic group), often a 5-6 membered ring. Typical heteroaryl groups include furan, isothiazole, thiadiazole, oxadiazole, indazole, indole, quinoline, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2,3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "hydroxy" or "hydroxyl" refers to the group —OH.

Various embodiments of the invention are described herein. It will be recognized that features specified in each embodiment may be combined with other specified features to provide further embodiments. The following enumerated embodiments are representative:

1. A compound of Formula (I):

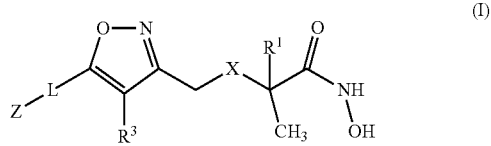

or a pharmaceutically acceptable salt thereof, wherein:

X is —NH—, and $R^1$ is —CH(OH)—Y;

or

X is —$CH_2$—, and $R^1$ is —CH(OH)—Y or —$SO_2R^2$ where $R^2$ is $C_1$-$C_3$ alkyl;

$R^3$ is H or halo;

Y is selected from a 5-membered heteroaryl ring containing 1-3 heteroatoms selected from N, O and S as ring members, phenyl, and $C_{1-3}$ alkyl, and each Y is optionally substituted with one to three $R^4$;

each $R^4$ is independently selected from halo, $C_{1-3}$ alkyl, and $C_{3-6}$ cycloalkyl, wherein the $C_{1-3}$ alkyl and $C_{3-6}$ cycloalkyl are each optionally substituted with up to three groups selected from halo, CN and —OH;

L is —C≡C— or —CR$^5$=CR$^5$—;

R$^5$ is independently selected at each occurrence from H, halo and methyl;

and

Z is selected from C$_{1-6}$ alkyl, C$_3$-C$_6$ cycloalkyl, pyridinyl, and phenyl, each of which is optionally substituted with up to three groups selected from halogen, hydroxy, C$_{1-4}$ alkoxy, C$_{1-4}$ haloalkoxy, CN, and C$_{1-4}$ alkyl that is optionally substituted with one to three groups selected from halogen, hydroxy, amino, CN, and C$_{1-3}$ alkoxy;

or, when L is —CR$^5$=CR$^5$—, Z taken together with one of the R$^5$ groups and any atoms connecting Z with the R$^5$ group can form a 3-7 membered cycloalkyl or cycloalkenyl group that is optionally substituted with up to three groups selected from halogen, hydroxy, C$_{1-4}$ alkoxy, C$_{1-4}$ haloalkoxy, CN, and C$_{1-4}$ alkyl that is optionally substituted with one to three groups selected from halogen, hydroxy, amino, CN, and C$_{1-3}$ alkoxy.

In certain of these embodiments, the compound is a compound of Formula (I):

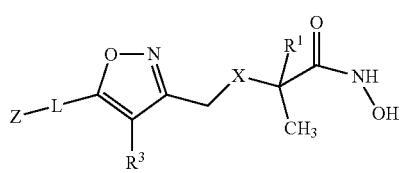

(I)

or a pharmaceutically acceptable salt thereof, wherein:

X is —NH—, and R$^1$ is —CH(OH)—Y;

or

X is —CH$_2$—, and R$^1$ is —CH(OH)—Y or —SO$_2$R$^2$ where R$^2$ is C$_1$-C$_3$ alkyl;

R$^3$ is H or halo;

Y is selected from a 5-membered heteroaryl ring containing 1-3 heteroatoms selected from N, O and S as ring members, phenyl, and C$_{1-3}$ alkyl, and each Y is optionally substituted with one to three R$^4$;

each R$^4$ is independently selected from halo, C$_{1-3}$ alkyl and C$_{3-6}$ cycloalkyl, wherein the C$_{1-3}$ alkyl and C$_{3-6}$ cycloalkyl are each optionally substituted with up to three groups selected from halo, CN and —OH;

L is —C≡C— or —CR$^5$=CR$^5$—;

R$^5$ is independently selected at each occurrence from H, halo and methyl;

and

Z is selected from C$_{1-6}$ alkyl, C$_3$-C$_6$ cycloalkyl, pyridinyl, and phenyl, each of which is optionally substituted with up to three groups selected from halogen, hydroxy, C$_{1-4}$ alkoxy, C$_{1-4}$ haloalkoxy, CN, and C$_{1-4}$ alkyl that is optionally substituted with one to three groups selected from halogen, hydroxy, amino, CN, and C$_{1-3}$ alkoxy.

In some of these embodiments, R$^3$ is H.

Specific compounds of the invention include, but are not limited to those in Table 1, e.g. any one or any subset of these compounds:

(R)-4-(5-(cyclopropylethynyl)isoxazol-3-yl)-N-hydroxy-2-methyl-2-(methylsulfonyl)butanamide (R)-4-(5-(cyclobutylethynyl)isoxazol-3-yl)-N-hydroxy-2-methyl-2-(methylsulfonyl)butanamide (R)-4-(5-(3,3-dimethylbut-1-yn-1-yl)isoxazol-3-yl)-N-hydroxy-2-methyl-2-(methylsulfonyl)butanamide (R)—N-hydroxy-2-methyl-2-(methylsulfonyl)-4-(5-(prop-1-yn-1-yl)isoxazol-3-yl)butanamide (R)-4-(5-(but-1-yn-1-yl)isoxazol-3-yl)-N-hydroxy-2-methyl-2-(methylsulfonyl)butanamide (R)—N-hydroxy-2-methyl-4-(5-(3-methylbut-1-yn-1-yl)isoxazol-3-yl)-2-(methylsulfonyl)butanamide (R)—N-hydroxy-2-methyl-2-(methylsulfonyl)-4-(5-(pent-1-yn-1-yl)isoxazol-3-yl)butanamide (R)—N-hydroxy-2-methyl-4-(5-((1-methylcyclopropyl)ethynyl)isoxazol-3-yl)-2-(methylsulfonyl)butanamide (R)-4-(5-(5-fluorobut-1-yn-1-yl)isoxazol-3-yl)-N-hydroxy-2-methyl-2-(methylsulfonyl)butanamide (R)-4-(5-(5-fluoropent-1-yn-1-yl)isoxazol-3-yl)-N-hydroxy-2-methyl-2-(methylsulfonyl)butanamide (R)-4-(5-(5,5-Difluoropent-1-yn-1-yl)isoxazol-3-yl)-N-hydroxy-2-methyl-2-(methylsulfonyl)butanamide (R)-4-(5-((3,3-difluorocyclobutyl)ethynyl)isoxazol-3-yl)-N-hydroxy-2-methyl-2-(methylsulfonyl)butanamide (R)-4-(5-((3-fluorocyclobutyl)ethynyl)isoxazol-3-yl)-N-hydroxy-2-methyl-2-(methylsulfonyl)butanamide (R)—N-hydroxy-4-(5-(5-hydroxy-5-methylhex-1-yn-1-yl)isoxazol-3-yl)-2-methyl-2-(methylsulfonyl)butanamide (R)—N-hydroxy-4-(5-((3-(methoxymethyl)cyclobutyl)ethynyl)isoxazol-3-yl)-2-methyl-2-(methylsulfonyl)butanamide (R)—N-hydroxy-4-(5-((3-(2-hydroxypropan-2-yl)cyclobutyl)ethynyl)isoxazol-3-yl)-2-methyl-2-(methylsulfonyl)butanamide N-hydroxy-4-(5-((4-(hydroxymethyl)phenyl)ethynyl)isoxazol-3-yl)-2-methyl-2-(methylsulfonyl)butanamide N-hydroxy-4-(5-((4-(2-hydroxyethyl)phenyl)ethynyl)isoxazol-3-yl)-2-methyl-2-(methylsulfonyl)butanamide N-hydroxy-4-(5-((4-(2-hydroxy-1-methoxyethyl)phenyl)ethynyl)isoxazol-3-yl)-2-methyl-2-(methylsulfonyl)butanamide N-hydroxy-2-methyl-2-(methylsulfonyl)-4-(5-(phenylethynyl) isoxazol-3-yl) butanamide N-hydroxy-4-(5-((4-((R)-2-hydroxypropyl)phenyl)ethynyl) isoxazol-3-yl)-2-methyl-2-(methylsulfonyl)butanamide (R)—N-hydroxy-4-(5-((4-((S)-2-hydroxy-1-methoxyethyl)phenyl)ethynyl)-isoxazol-3-yl)-2-methyl-2-(methylsulfonyl)butanamide (R)-4-(5-((4-((S)-1,2-dihydroxyethyl)phenyl)ethynyl)isoxazol-3-yl)-N-hydroxy-2-methyl-2-(methylsulfonyl)butanamide (R)-4-(5-((4-((R)-1,2-dihydroxyethyl)phenyl)ethynyl)isoxazol-3-yl)-N-hydroxy-2-methyl-2-(methylsulfonyl)butanamide (2S,3R)-2-(((5-(cyclopropylethynyl)isoxazol-3-yl)methyl)amino)-N,3-dihydroxy-2-methyl-3-(5-methylisoxazol-3-yl)propanamide (2S,3R)-2-(((5-(cyclobutylethynyl)isoxazol-3-yl)methyl)amino)-N,3-dihydroxy-2-methyl-3-(5-methylisoxazol-3-yl)propanamide (2S,3R)—N,3-dihydroxy-2-methyl-3-(5-methylisoxazol-3-yl)-2-(((5-(phenylethynyl)isoxazol-3-yl)methyl)amino)propanamide N,3-dihydroxy-3-(5-(hydroxymethyl)isoxazol-3-yl)-2-methyl-2-(((5-(phenylethynyl)isoxazol-3-yl)methyl)amino)propanamide]

(2S,3R)—N,3-dihydroxy-2-(((5-(6-methoxyhex-1-yn-1-yl)isoxazol-3-yl)methyl)amino)-2-methyl-3-(5-methylisoxazol-3-yl)propanamide 2-(((5-(cyclopropylethynyl) isoxazol-3-yl) methyl) amino)-3-(5-cyclopropylisoxazol-3-yl)-N,3-dihydroxy-2-methyl-propanamide (R,E)-4-(5-(but-1-en-1-yl)isoxazol-3-yl)-N-hydroxy-2-methyl-2-(methylsulfonyl)butanamide (R,E)-4-(5-(2-cyclopropylvinyl)isoxazol-3-yl)-N-hydroxy-2-methyl-2-(methylsulfonyl)butanamide (R,E)-4-(5-(but-2-en-2-yl)isoxazol-3-yl)-N-hydroxy-2-methyl-2-(methylsulfonyl)butanamide (R,Z)-4-(5-(but-2-en-2-yl)isoxazol-3-yl)-N-hydroxy-2-methyl-2-(methylsulfonyl)butanamide (R,Z)-4-(5-(2-cyclopropyl-1-fluorovinyl)isoxazol-3-yl)-N-hydroxy-2-methyl-2-(methylsulfonyl)butanamide and (R,E)-4-(5-(2-cyclopropyl-1-fluorovinyl)isoxazol-3-yl)-N-hydroxy-2-methyl-2-(methylsulfonyl)butanamide (R,Z)-4-(5-(2-cyclopropyl-2-fluorovinyl) isoxazol-3-yl)-N-hydroxy-2-methyl-2-(methylsulfonyl)butanamide (R)-4-(5-(cyclohex-1-en-1-yl)isoxazol-3-yl)-N-hydroxy-2-methyl-2-(methylsulfonyl)butanamide 2. The compound of embodiment 1, wherein $R^1$ is —CH(OH)—Y. In certain of these embodiments, Y is an isoxazole such as

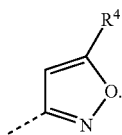

In some of these embodiments, $R^4$ is selected from methyl, ethyl, isopropyl, and cyclopropyl.

3. The compound of embodiment 1, wherein $R^1$ is —$SO_2R^2$. In some of these embodiments, $R^2$ is methyl.

4. The compound of any of embodiments 1-3, wherein X is —$CH_2$—.

5. The compound of any of embodiments 1-2, wherein X is —NH—.

6. The compound of embodiment 2, 4, or 5, wherein Y is isoxazole, optionally substituted with one or two $R^4$.

7. The compound of embodiment 6, wherein Y is

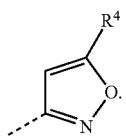

In certain of these embodiments, $R^4$ is $C_{1-3}$ alkyl or $C_{3-5}$ cycloalkyl; for example $R^4$ is methyl or cyclopropyl. The dashed line in this and other substituent groups drawn as partial structures indicates which position on the group is attached to the remainder of the molecule.

8. The compound of any of embodiments 1-7, wherein Z is phenyl substituted with up to three groups selected from halogen, $C_{1-4}$ alkoxy, $C_{1-4}$ haloalkoxy, CN, and $C_{1-4}$ alkyl optionally substituted with one to three groups selected from halogen, hydroxy, amino, CN, and $C_{1-3}$ alkoxy. In some of these embodiments, Z is a phenyl group of the formula

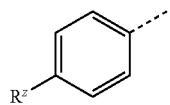

wherein $R^z$ is selected from H, halogen, $C_{1-4}$ alkoxy, $C_{1-4}$ haloalkoxy, CN, and $C_{1-4}$ alkyl optionally substituted with one to three groups selected from halogen, hydroxy, amino, CN, and $C_{1-3}$ alkoxy.

In some of these embodiments, $R^z$ is $C_{1-3}$ alkyl substituted with one or two groups selected from hydroxy and $C_{1-3}$ alkoxy.

9. The compound of any of embodiments 1-7, wherein Z is $C_1$-$C_4$ alkyl or $C_3$-$C_6$ cycloalkyl, and Z is optionally substituted with up to three groups selected from halogen, $C_{1-4}$ alkoxy, $C_{1-4}$ haloalkoxy, CN, and $C_{1-4}$ alkyl optionally substituted with one to three groups selected from halogen, hydroxy, amino, CN, and $C_{1-3}$ alkoxy. In some of these embodiments, Z is cyclopropyl or cyclobutyl. In other of these embodiments, Z is $C_{1-4}$ alkyl substituted with one to three groups selected from hydroxy, CN, and $C_{1-3}$ alkoxy.

10. The compound of any of the preceding embodiments, wherein L is —C≡C—. Alternatively, the compound of any of the preceding embodiments wherein L is —$CR^5$=$CR^5$—.

11. The compound of embodiment 1, wherein the compound is of Formula (II):

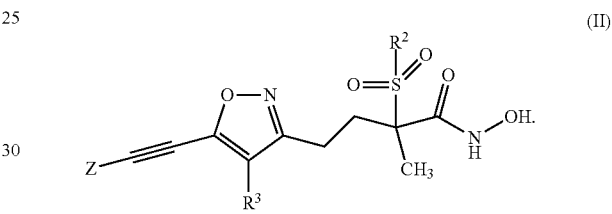

12. The compound of embodiment 1 or any of embodiments 5-10, wherein the compound is of Formula (III):

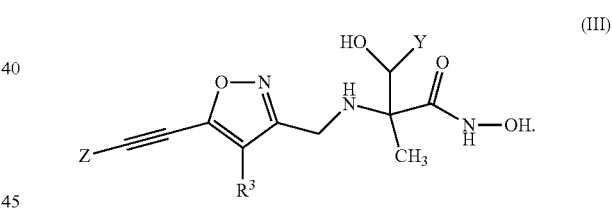

13. A pharmaceutical composition, comprising:
a compound according to any of embodiments 1 to 12 and
a pharmaceutically acceptable carrier or excipient. In some of these embodiments, the pharmaceutical composition comprises two or more pharmaceutically acceptable carriers.

14. A pharmaceutical combination composition, comprising:
a compound according to any of embodiments 1 to 12,
an antibacterially effective amount of a second therapeutic agent, and
a pharmaceutically acceptable carrier or excipient.

15. The pharmaceutical combination composition according to embodiment 14, wherein the second therapeutic agent is selected from the group consisting of Ampicillin, Piperacillin, Penicillin G, Ticarcillin, Imipenem, Meropenem, Azithromycin, Erythromycin, Aztreonam, Cefepime, Cefotaxime, Ceftriaxone, Ceftazidime, Ciprofloxacin, Levofloxacin, Clindamycin, Doxycycline, Gentamycin, Amikacin, Tobramycin, Tetracycline, Tigecycline, Rifampicin, Vancomycin and Polymyxin.

16. A method of inhibiting a deacetylase enzyme in a Gram-negative bacterium, comprising contacting the Gram-negative bacterium with the compound according to any one of embodiments 1 to 12.

17. A method for treating a subject with a Gram-negative bacterial infection, comprising:
administering to the subject in need thereof an antibacterially effective amount of the compound according to any of embodiments 1 to 12. In some of these embodiments, the compound is admixed with a pharmaceutically acceptable carrier.

18. The method of embodiment 17, wherein the Gram negative bacterial infection is an infection comprising at least one bacterium selected from the group consisting of *Pseudomonas aeruginosa* and other *Pseudomonas* spp., *Stenotrophomonas maltophilia*, *Burkholderia cepacia* and other *Burkholderia* spp., *Alcaligenes xylosoxidans*, *Acinetobacter* spp., *Achromobacter* spp., *Aeromonas* spp., *Enterobacter* spp., *Eschericia coli*, *Haemophilus* spp., *Klebsiella* spp., *Moraxella* spp., *Bacteroides* spp., *Francisella* spp., *Shigella* spp., *Proteus* spp., *Porphyromonas* spp., *Prevotella* spp., *Mannheimia haemolyiticus*, *Pastuerella* spp., *Providencia* spp., *Vibrio* spp., *Salmonella* spp., *Bordetella* spp., *Borrelia* spp., *Helicobacter* spp., *Legionella* spp., *Citrobacter* spp., *Cedecea* spp., *Serratia* spp., *Campylobacter* spp., *Yersinia* spp., *Fusobacterium* spp., and *Neisseria* spp.

19. The method of embodiment 18, wherein the bacterium is a member from the Pseudomonadales and Enterobacteriaceae species which is selected from the group consisting of organisms such as *Pseudomonas*, *Acinetobacter*, *Stenotrophomonas*, *Burkholderia*, *Serratia*, *Proteus*, *Klebsiella*, *Enterobacter*, *Citrobacter*, *Salmonella*, *Shigella*, *Providencia*, *Morganella*, *Cedecea*, *Yersina* and *Edwardsiella* species and *Escherichia coli*.

20. A compound according to any one of embodiments 1 to 12 or a pharmaceutically acceptable salt thereof, for use as a medicament.

21. The compound of embodiment 20, wherein the medicament is for the treatment of a Gram-negative bacterial infection.

22. A compound according to any one of embodiments 1 to 12 or a pharmaceutically acceptable salt thereof, for use in treatment of a Gram-negative bacterial infection, wherein the bacterial infection is selected from the Pseudomonadales and Enterobacteriaceae species which is selected from the group consisting of organisms such as *Pseudomonas*, *Acinetobacter*, *Stenotrophomonas*, *Burkholderia*, *Serratia*, *Proteus*, *Klebsiella*, *Enterobacter*, *Citrobacter*, *Salmonella*, *Shigella*, *Providencia*, *Morganella*, *Cedecea*, *Yersina* and *Edwardsiella* species and *Escherichia coli*.

23. Use of the compound according to any one of embodiments 1 to 12, for the preparation of a medicament for the treatment of a Gram-negative bacterial infection in a subject, wherein the bacterial infection is selected from the Pseudomonadales and Enterobacteriaceae species which is selected from the group consisting of organisms such as *Pseudomonas*, *Acinetobacter*, *Stenotrophomonas*, *Burkholderia*, *Serratia*, *Proteus*, *Klebsiella*, *Enterobacter*, *Citrobacter*, *Salmonella*, *Shigella*, *Providencia*, *Morganella*, *Cedecea*, *Yersina* and *Edwardsiella* species and *Escherichia coli*.

24. The use of embodiment 23, wherein the bacterial infection is from the Pseudomonadales and Enterobacteriaceae species which is selected from the group consisting of organisms such as *Pseudomonas*, *Acinetobacter*, *Stenotrophomonas*, *Burkholderia*, *Serratia*, *Proteus*, *Klebsiella*, *Enterobacter*, *Citrobacter*, *Salmonella*, *Shigella*, *Providencia*, *Morganella*, *Cedecea*, *Yersina* and *Edwardsiella* species and *Escherichia coli*.

The compounds and compositions described herein can be used or administered in combination with one or more therapeutic agents that act as immunomodulators, e.g., an activator of a costimulatory molecule, or an inhibitor of an immune-inhibitory molecule, or a vaccine. The Programmed Death 1 (PD-1) protein is an inhibitory member of the extended CD28/CTLA4 family of T cell regulators (Okazaki et al. (2002) *Curr Opin Immunol* 14: 391779-82; Bennett et al. (2003) *J. Immunol.* 170:711-8). PD-1 is expressed on activated B cells, T cells, and monocytes. PD-1 is an immune-inhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745), and is up-regulated in chronic infections. The interaction between PD-1 and PD-L1 can act as an immune checkpoint, which can lead to, e.g., a decrease in infiltrating lymphocytes, a decrease in T-cell receptor mediated proliferation, and/or immune evasion by cancerous or infected cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci. USA* 99:12293-7; Brown et al. (2003) *J. Immunol.* 170:1257-66). Immunomodulation can be achieved by binding to either the immune-inhibitory protein (e.g., PD-1) or to binding proteins that modulate the inhibitory protein (e.g., PD-L1, PD-L2).

In one embodiment, the combination therapies of the invention include an immunomodulator that is an inhibitor or antagonist of an inhibitory molecule of an immune checkpoint molecule. In another embodiment the immunomodulator binds to a protein that naturally inhibits the immuno-inhibitory checkpoint molecule. When used in combination with antibacterial compounds, these immunomodulators can enhance the antimicrobial response, and thus enhance efficacy relative to treatment with the antibacterial compound alone. Thus a compound of any one of embodiments 1-12 or a pharmaceutical composition of embodiment 13 can be administered to a subject who is being treated with an immunomodulator; the immunomodulator and compound can be administered together or separately, but are simultaneously used to treat an infection treatable with the compounds of Formula (I) as described herein.

The term "immune checkpoints" refers to a group of molecules on the cell surface of CD4 and CD8 T cells. These molecules can effectively serve as "brakes" to down-modulate or inhibit an adaptive immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and LAG3, which directly inhibit immune cells. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD160, 2B4 and/or TGFR beta. Inhibition of an inhibitory molecule can be performed by inhibition at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide, e.g., a soluble ligand, or an antibody or antigen-binding fragment thereof, that binds to the inhibitory molecule.

The immunomodulator can be administered concurrently with, prior to, or subsequent to, one or more compounds of the invention, and optionally one or more additional therapies or therapeutic agents. The therapeutic agents in the combination can be administered in any order. In general, each agent will be administered at a dose and/or on a time schedule determined for that agent. It will further be appreciated that the therapeutic agents utilized in this combination may be administered together in a single composition or administered separately in different compositions. In general, it is expected that each of the therapeutic agents utilized in combination be utilized at levels that do not exceed the levels at which they are utilized individually. In some embodiments, the levels utilized in combination will be lower than those utilized individually.

In certain embodiments, the antibacterial compounds described herein are administered in combination with one or more immunomodulators that are inhibitors of PD-1, PD-L1 and/or PD-L2. Each such inhibitor may be an antibody, an antigen binding fragment thereof, an immunoadhesin, a fusion protein, or an oligopeptide. Examples of such immunomodulators are known in the art.

In some embodiments, the immunomodulator is an anti-PD-1 antibody chosen from MDX-1106, Merck 3475 or CT-011.

In some embodiments, the immunomodulator is an immunoadhesin (e.g., an immunoadhesin comprising an extracellular or PD-1 binding portion of PD-LI or PD-L2 fused to a constant region (e.g., an Fc region of an immunoglobulin sequence).

In some embodiments, the immunomodulator is a PD-1 inhibitor such as AMP-224.

In some embodiments, the immunomodulator is a PD-LI inhibitor such as anti-PD-LI antibody.

In some embodiments, the immunomodulator is an anti-PD-LI binding antagonist chosen from YW243.55.S70, MPDL3280A, MEDI-4736, MSB-0010718C, or MDX-1105. MDX-1105, also known as BMS-936559, is an anti-PD-LI antibody described in WO2007/005874. Antibody YW243.55.S70 is an anti-PD-LI described in WO 2010/077634.

In some embodiments, the immunomodulator is nivolumab (CAS Registry Number: 946414-94-4). Alternative names for nivolumab include MDX-1106, MDX-1106-04, ONO-4538, or BMS-936558. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449, EP2161336 and WO2006/121168.

In some embodiments, the immunomodulator is an anti-PD-1 antibody Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509, WO2009/114335, and WO2013/079174.

In some embodiments, the immunomodulator is Pidilizumab (CT-011; Cure Tech), a humanized IgG1k monoclonal antibody that binds to PD1. Pidilizumab and other humanized anti-PD-1 monoclonal antibodies are disclosed in WO2009/101611.

Other anti-PD1 antibodies useful as immunomodulators for use in the methods disclosed herein include AMP 514 (Amplimmune), and anti-PD1 antibodies disclosed in U.S. Pat. No. 8,609,089, US 2010028330, and/or US 20120114649. In some embodiments, the anti-PD-L1 antibody is MSB0010718C. MSB0010718C (also referred to as A09-246-2; Merck Serono) is a monoclonal antibody that binds to PD-L1.

In some embodiments, the immunomodulator is MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents useful as immunomodulators for methods of the invention include YW243.55.S70 (see WO2010/077634), MDX-1105 (also referred to as BMS-936559), and anti-PD-L1 binding agents disclosed in WO2007/005874.

In some embodiments, the immunomodulator is AMP-224 (B7-DCIg; Amplimmune; e.g., disclosed in WO2010/027827 and WO2011/066342), is a PD-L2 Fc fusion soluble receptor that blocks the interaction between PD1 and B7-H1.

In some embodiments, the immunomodulator is an anti-LAG-3 antibody such as BMS-986016. BMS-986016 (also referred to as BMS986016) is a monoclonal antibody that binds to LAG-3. BMS-986016 and other humanized anti-LAG-3 antibodies are disclosed in US 2011/0150892, WO2010/019570, and WO2014/008218

In certain embodiments, the combination therapies disclosed herein include a modulator of a costimulatory molecule or an inhibitory molecule, e.g., a co-inhibitory ligand or receptor.

In one embodiment, the costimulatory modulator, e.g., agonist, of a costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the combination therapies disclosed herein include an immunomodulator that is a costimulatory molecule, e.g., an agonist associated with a positive signal that includes a costimulatory domain of CD28, CD27, ICOS and/or GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. No. 7,812,135, U.S. Pat. No. 8,388,967, U.S. Pat. No. 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the immunomodulator used is a soluble ligand (e.g., a CTLA-4-Ig), or an antibody or antibody fragment that binds to PD-L1, PD-L2 or CTLA4. For example, the anti-PD-1 antibody molecule can be administered in combination with an anti-CTLA-4 antibody, e.g., ipilimumab, for example. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, an anti-PD-1 antibody molecule is administered after treatment with a compound of the invention as described herein.

In another embodiment, an anti-PD-1 or PD-L1 antibody molecule is administered in combination with an anti-LAG-3 antibody or an antigen-binding fragment thereof. In another embodiment, the anti-PD-1 or PD-L1 antibody molecule is administered in combination with an anti-TIM-3 antibody or antigen-binding fragment thereof. In yet other embodiments, the anti-PD-1 or PD-L1 antibody molecule is administered in combination with an anti-LAG-3 antibody and an anti-TIM-3 antibody, or antigen-binding fragments thereof. The combination of antibodies recited herein can be administered separately, e.g., as separate antibodies, or linked, e.g., as a bispecific or trispecific antibody molecule. In one embodiment, a bispecific antibody that includes an anti-PD-1 or PD-L1 antibody molecule and an anti-TIM-3 or anti-LAG-3 antibody, or antigen-binding fragment thereof, is administered. In certain embodiments, the combination of antibodies recited herein is used to treat a bacterial infection selected from those described herein. The efficacy of the aforesaid combinations can be tested in animal models known in the art.

Exemplary immunomodulators that can be used in the combination therapies include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Exemplary doses of such immunomodulators that can be used in combination with the antibacterial compounds of the invention include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Examples of embodiments of the methods of using the antibacterial compounds of the invention in combination with an immunomodulator include these:

i. A method to treat a bacterial infection in a subject, comprising administering to the subject a compound of Formula (I) as described herein, and an immunomodulator.

ii. The method of embodiment i, wherein the immunomodulator is an activator of a costimulatory molecule or an inhibitor of an immune checkpoint molecule.

iii. The method of either of embodiments i and ii, wherein the activator of the costimulatory molecule is an agonist of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 and CD83 ligand.

iv. The method of any of embodiments i-iii above, wherein the inhibitor of the immune checkpoint molecule is chosen from PD-1, PD-L1, PD-L2, CTLA4, TIM3, LAG3, VISTA, BTLA, TIGIT, LAIR1, CD160, 2B4 and TGFR beta.

v. The method of any of any of embodiments i-iii, wherein the inhibitor of the immune checkpoint molecule is chosen from an inhibitor of PD-1, PD-L1, LAG-3, TIM-3 or CTLA4, or any combination thereof.

vi. The method of any of embodiments i-v, wherein the inhibitor of the immune checkpoint molecule is a soluble ligand or an antibody or antigen-binding fragment thereof, that binds to the immune checkpoint molecule.

vii. The method of any of embodiments i-vi, wherein the antibody or antigen-binding fragment thereof is from an IgG1 or IgG4 (e.g., human IgG1 or IgG4).

viii. The method of any of embodiments i-vii, wherein the antibody or antigen-binding fragment thereof is altered, e.g., mutated, to increase or decrease one or more of: Fc receptor binding, antibody glycosylation, the number of cysteine residues, effector cell function, or complement function.

ix. The method of any of embodiments i-viii, wherein the antibody molecule is a bispecific or multispecific antibody molecule that has a first binding specificity to PD-1 or PD-L1 and a second binding specificity to TIM-3, LAG-3, or PD-L2.

x. The method of any of embodiments i-ix, wherein the immunomodulator is an anti-PD-1 antibody chosen from Nivolumab, Pembrolizumab or Pidilizumab.

xi. The method of any of embodiments i-x, wherein the immunomodulator is an anti-PD-L1 antibody chosen from YW243.55.S70, MPDL3280A, MEDI-4736, MSB-0010718C, or MDX-1105.

xii. The method of any of embodiments i-x, wherein the immunomodulator is an anti-LAG-3 antibody molecule.

xiii. The method of embodiment xii, wherein the anti-LAG-3 antibody molecule is BMS-986016, xiv. The method of any of embodiments i-x, wherein the immunomodulator is an anti-PD-1 antibody molecule administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg., e.g., once a week to once every 2, 3, or 4 weeks.

xv. The method of embodiment xiv, wherein the anti-PD-1 antibody molecule is administered at a dose from about 10 to 20 mg/kg every other week.

xvi. The method of embodiment xv, wherein the anti-PD-1 antibody molecule, e.g., nivolumab, is administered intravenously at a dose from about 1 mg/kg to 3 mg/kg, e.g., about 1 mg/kg, 2 mg/kg or 3 mg/kg, every two weeks.

xvii. The method of embodiment xv, wherein the anti-PD-1 antibody molecule, e.g., nivolumab, is administered intravenously at a dose of about 2 mg/kg at 3-week intervals.

Compounds of the invention, particularly compounds of embodiments 1-12 described above, exhibit greater efficacy against important drug-resistant Gram-negative pathogens than hydroxamic acid compounds previously reported or improved off-target effect profiles; thus these compounds are especially useful to treat subjects with drug-resistant infections or avoid adverse side effects.

Compounds of the invention contain one or more chiral centers. These compounds may be made and used as single isomers or as mixtures of isomers. Methods for separating the isomers, including diastereomers and enantiomers, are known in the art, and examples of suitable methods are described herein. In certain embodiments, the compounds of the invention are used as a single substantially pure isomer, meaning at least 90% of a sample of the compound is the specified isomer and less than 10% of the sample is any other isomer or mixture of isomers. Preferably, at least 95% of the sample is a single isomer. Selection of a suitable isomer is within the ordinary level of skill, as one isomer will typically be more active in the LpxC in vitro assay described herein and will be the preferred isomer. Where in vitro activity differences between isomers are relatively small, e.g. less than about a factor of 4, a preferred isomer may be selected based on activity level against Gram-negative bacteria such as *P. aeruginosa* in cell culture, using methods such as those described herein: the isomer having a lower MIC (minimum inhibitory concentration) is preferred.

In certain embodiments, the compounds of the invention have the stereochemistry depicted in Formula (IA).

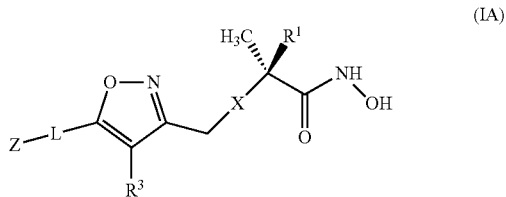

These compounds may or may not have a second chiral center at the hydroxyl-substituted carbon, depending on the selection of Y. Where a second chiral center is present, the preferred diastereomer is typically the one having a greater potency as an inhibitor of LpxC by at least a factor of 4; if the two isomers do not differ by a factor of 4 in in vitro activity, each isomer or a mixture of the two may suitably be used for the methods and compositions of the invention, or the isomer providing a lower MIC on a bacterial species of interest may be preferred.

The compounds of the invention may be synthesized by the general synthetic routes below, specific examples of which are described in more detail in the Examples.

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers or diastereomers, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is intended to represent unlabeled forms as well as isotopically labeled forms of the compounds of the present invention having up to three atoms with non-natural isotope distributions, e.g., sites that are enriched in deuterium or $^{13}C$ or $^{15}N$. Isotopically labeled compounds have structures depicted by the formulas given herein except that one or more atoms are replaced by an atom having a selected atomic mass or mass number other than the natural-abundance mass distribution. Examples of isotopes that can be usefully over-incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^3H$ and $^{14}C$, or those in which non-radioactive isotopes, such as $^2H$ and $^{13}C$ are present at levels substantially above normal isotope distribution. Such isotopically labelled compounds are useful in metabolic studies (with $^{14}C$, for example), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent typically employed. Labeled samples may be useful with quite low isotope incorporation, such as where a radiolabel is used to detect trace amounts of the compound.

Further, more extensive substitution with heavier isotopes, particularly deuterium (i.e., $^2H$ or D), may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention, and typically a sample of a compound having deuterium as a substituent has at least 50% deuterium incorporation at the labeled position(s). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The present invention provides novel compounds, pharmaceutical formulations including the compounds, methods of inhibiting UDP-3-O—(R-3-hydroxydecanoyl)-N-acetylglucosamine deacetylase (LpxC), and methods of treating Gram-negative bacterial infections.

In another aspect, the invention provides a method of inhibiting a deacetylase enzyme in a Gram-negative bacterium, the method comprising the step of contacting the Gram-negative bacteria with a compound of the invention, e.g., a compound of Formula I or salt thereof.

In still another aspect, the invention provides a method for treating a subject with a Gram-negative bacterial infection, the method comprising the step of administering to the subject in need thereof an antibacterially effective amount of a compound of the invention, e.g., a compound of Formula I or salt thereof with a pharmaceutically acceptable carrier.

The compounds of the invention can be administered by known methods, including oral, parenteral, inhalation, and the like. In certain embodiments, the compound of the invention is administered orally, as a pill, lozenge, troche, capsule, solution, or suspension. In other embodiments, a compound of the invention is administered by injection or infusion. Infusion is typically performed intravenously, often over a period of time between about 15 minutes and 4 hours. In other embodiments, a compound of the invention is administered intranasally or by inhalation; inhalation methods are particularly useful for treatment of respiratory infections. In other embodiments, a compound of the invention is administered intravenously, as by IV infusion, wherein the compound may be administered while it is dissolved in any suitable intravenous solution such as Ringer's lactate or an isotonic glucose or saline solution.

The compounds of the invention can be used for treating conditions caused by the bacterial production of endotoxin and, in particular, by Gram-negative bacteria and bacteria that use LpxC in the biosynthesis of lipopolysaccharide (LPS) or endotoxin.

The compounds of the invention also are useful in the treatment of patients suffering from or susceptible to respiratory tract infections (pneumonia, lung abscesses, bronchiectasis), bacteremia (sepsis), cystic fibrosis, skin and soft tissue infections (wound, surgical infections, complicated diabetic foot, complicated burns) complicated intraabdominal or complicated urinary track infections and sexually transmitted diseases caused by Gram-negative pathogens. The compounds of the invention also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, treatment includes the administration of a compound of the invention, or a combination of compounds of the invention, optionally with a second agent wherein the second agent is a second antibacterial agent or a second non-antibacterial agent.

For sepsis, septic shock, systemic inflammation, localized inflammation, chronic obstructive pulmonary disease (COPD) and acute exacerbations of chronic bronchitis (AECB), preferred second non-antibacterial agents include antiendotoxins including endotoxin receptor-binding antibodies, endotoxin-binding antibodies, antiCD14-binding protein antibodies, antilipopolysaccharide-binding protein antibodies and tyrosine kinase inhibitors.

In treatment of serious or chronic respiratory tract infections, the compounds of the present invention may also be used with second non-antibacterial agents administered via inhalation. Preferred non-antibacterial agents used in this treatment include anti-inflammatory steroids, non-steroidal anti-inflammatory agents, bronchiodilators, mucolytics, anti-asthma therapeutics and lung fluid surfactants. In particular, the non-antibacterial agent may be selected from a group consisting of albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, salneterol, bronchiodilators, mucolytics, calfactant, beractant, poractant alfa, surfaxin and pulmozyme (also called domase alfa).

The compounds of the invention can be used, alone or in combination with a second antibacterial agent for the treatment of a serious or chronic respiratory tract infection including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter baumanii, Alcaligenes xylosoxidans, Flavobacterium meningosepticum, Providencia stuartii* and *Citrobacter freundi*, community lung infections such as those caused by *Haemophilus influenzae, Legionella species, Moraxella catarrhalis, Enterobacter species, Acinetobacter species, Klebsiella* species, and *Proteus* species, and infections caused by other bacterial species such as *Neisseria* species, *Shigella* species, *Salmonella* species, *Helicobacter pylori, Vibrionaceae* and *Bordetella* species as well as the infections is caused by a *Brucella* species, *Francisella tularensis* and/or *Yersinia pestis*.

A compound of the present invention may also be used in combination with other agents (combination partners), e.g., an additional antibiotic agent that is or is not of the formula I, for treatment of a bacterial infection in a subject.

By the term "combination", is meant either a fixed combination in one dosage unit form, as separate dosage forms suitable for use together either simultaneously or sequentially, or as a kit of parts for the combined administration where a compound of the present invention and a combination partner may be administered independently at the same time or separately within time intervals that especially allow that the combination partners show a cooperative, e.g., synergistic, effect, or any combination thereof.

When used for treating Gram-negative bacteria, the compounds of the present invention can be used to sensitize Gram-negative bacteria to the effects of a second agent.

In certain embodiments of the present invention, a compound of the present invention is used in combination with a second antibacterial agent; non-limiting examples of second antibacterial agents for such use may be selected from the following groups:

(1) Macrolides or ketolides such as erythromycin, azithromycin, clarithromycin, and telithromycin;

(2) Beta-lactams including penicillin such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporin such as cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and carbapenems such as carbapenem, imipenem, meropenem and PZ-601;

(3) Monobactams such as aztreonam;

(4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin;

(5) Antibacterial sulfonamides and antibacterial sulphanilamides, including para-aminobenzoic acid, sulfadiazine, sulfisoxazole, sulfamethoxazole and sulfathalidine;

(6) Aminoglycosides such as streptomycin, neomycin, kanamycin, paromycin, gentamicin, tobramycin, amikacin, netilmicin, spectinomycin, sisomicin, dibekalin and isepamicin;

(7) Tetracyclines such as tetracycline, chlortetracycline, demeclocycline, minocycline, oxytetracycline, methacycline, doxycycline, tegacycline;

(8) Rifamycins such as rifampicin (also called rifampin), rifapentine, rifabutin, bezoxazinorifamycin and rifaximin;

(9) Lincosamides such as lincomycin and clindamycin;

(10) Glycopeptides such as vancomycin and teicoplanin;

(11) Streptogramins such as quinupristin and daflopristin;

(12) Oxazolidinones such as linezolid and tedizolid;

(13) Polymyxin, colistin and colymycin;

(14) Trimethoprim and bacitracin.

(15) Efflux pump inhibitors.

The second antibacterial agent may be administered in combination with the compounds of the present inventions, wherein the second antibacterial agent is administered prior to, simultaneously with, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

In some embodiments, a combination of a compound of the invention and a second antibacterial agent may provide synergistic activity. For example, use of a compound of the invention with vancomycin or a cephalosporin may be synergistic; thus in some embodiments, the compound of the invention is used in combination with vancomycin or a cephalosporin, typically by infusion. The compound of the invention and second antibacterial agent may be administered together, separate but simultaneously, or sequentially.

When used for treating serious or chronic respiratory tract infections, the compounds of the invention may be used alone or in combination with a second antibacterial agent; in some embodiments, the second antibacterial agent is administered via inhalation. Optionally, the combination may be administered as a single composition by inhalation. In the case of administration by inhalation, a suitable second antibacterial agent is selected from the group consisting of tobramycin, gentamicin, aztreonam, ciprofloxacin, polymyxin, colistin, colymycin, vancomycin, cephalosporins, azithromycin and clarithromycin. Vancomycin is sometimes preferred.

An "effective amount" of a compound is that amount necessary or sufficient to treat or prevent a bacterial infection and/or a disease or condition described herein. In an example, an effective amount of a LpxC inhibitor of Formula I is an amount sufficient to treat bacterial infection in a subject. In another example, an effective amount of the LpxC inhibitor is an amount sufficient to treat a bacterial infection, such as, but not limited to *Pseudomonas aeruginosa* and the like, in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of a compound of Formula (I) as active ingredient in combination with a pharmaceutically acceptable carrier, or optionally two or more pharmaceutically acceptable carriers.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable carriers are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Intravenous infusion is sometimes a preferred method of delivery for compounds of the invention. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, frequently from about 0.01 to about 50 mg per kg per day, and often from about 1.0 to about 50 mg per kg per day. Total daily dosage by intravenous administration is typically 1-4 grams/day for a typical subject (e.g., a 70 kg human subject); total daily dosage by inhalation would typically be 50-500 mg per day, or about 100-200 mg. An effective amount is that amount treats a bacterial infection.

If desired, the effective daily dose of the active compound may be administered as one, two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered intravenously are typically administered in one to three doses per day.

While it is possible for a compound of the present invention to be administered alone, it is preferable to administer the compound as a pharmaceutical composition such as those described herein.

The compounds as described herein may be synthesized by the general synthetic routes below, specific examples of which are described in more detail in the Examples.

General Synthetic Procedures

Compounds of the present invention are prepared from commonly available compounds using procedures known to those skilled in the art in view of the examples and schemes provided herein.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H$^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

In accordance with the foregoing the present invention provides in a yet further aspect:

A pharmaceutical combination comprising a) a first agent which is a compound of the invention, e.g. a compound of formula I or any subformulae thereof, and b) a co-agent, e.g. a second drug agent as defined above.

A method as defined above comprising co-administration, e.g. concomitantly or in sequence, of a therapeutically effective amount of a compound of the invention, e.g. a compound of formula I or any subformulae thereof, and a co-agent, e.g. a second therapeutic agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

EXAMPLES

The invention is further illustrated by the following examples, which should not be construed as limiting. The assays used throughout the Examples are well established in the art: demonstration of efficacy in these assays is generally regarded as predictive of efficacy in subjects.

ABBREVIATIONS

Ac acetyl
ACN Acetonitrile
AcOEt/EtOAc Ethyl acetate
AcOH acetic acid
aq aqueous
Ar aryl
Bn benzyl
Bu butyl (nBu=n-butyl, tBu=tert-butyl)
CDI Carbonyldiimidazole
$CH_3CN$ Acetonitrile
DBU 1,8-Diazabicyclo[5.4.0]-undec-7-ene
$Boc_2O$ di-tert-butyl dicarbonate
DCE 1,2-Dichloroethane
DCM Dichloromethane
DiBAl-H Diisobutylaluminum Hydride
DIPEA N-Ethyldiisopropylamine
DMAP Dimethylaminopyridine
DMF N,N'-Dimethylformamide
DMSO Dimethylsulfoxide
EI Electrospray ionisation
$Et_2O$ Diethylether
$Et_3N$ Triethylamine
Ether Diethylether
EtOAc Ethylacetate
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HMPA Hexamethylphosphoramide
HOBt 1-Hydroxybenzotriazole
HPLC High Performance Liquid Chromatography
$H_2O$ Water
L liter(s)
LC-MS Liquid Chromatography Mass Spectrometry
LiHMDS Lithium bis(trimethylsilyl)amide
$MgSO_4$ Magnesium Sulfate
Me methyl
MeI Iodomethane
MeOH Methanol
mg milligram
min minute(s)
mL milliliter
MS Mass Spectrometry
$NaHCO_3$ Sodium Bicarbonate
$Na_2SO_4$ Sodium Sulfate
$NH_2OH$ hydroxylamine
Pd/C palladium on charcoal
$Pd(OH)_2$ palladium hydroxide
PG protecting group
Ph phenyl
$Ph_3P$ triphenyl phosphine
Prep Preparative
Rf ratio of fronts
RP reverse phase
Rt Retention time
rt Room temperature
$SiO_2$ Silica gel
$SOCl_2$ Thionyl Chloride
TBAF Tetrabutylammonium fluoride
TBDMS t-Butyldimethylsilyl
TEA Triethylamine
TFA Trifluoroacetic acid
THF Tetrahydrofuran
TLC Thin Layer Chromatography
TsCl toluene sulfonyl chloride The compounds of the invention can be produced by organic synthesis methods known to one of ordinary skill in the art with reference to the following reaction schemes and examples. General methods for synthesis of compounds of Formula (I) are provided in Schemes A-C below.

General Synthetic Schemes

A general method to synthesize compounds of Formula (II) is depicted in Scheme A. The first step is to generate a nitrile oxide in situ from aldoxime A-2, which then undergoes cycloaddition with an alkyne A-1 to provide isoxazole A-3. The ester A-4 can be converted to hydroxamic acid II via direct amide synthesis in the presence of hydroxylamine and a base. Alternative hydroxamic acid II can be synthesized via saponification of the ester and amidation of the free acid with O-(tetrahydro-2H-pyran-2-yl)hydroxylamine (THPONH$_2$), followed by de-protection of the THP under acidic conditions (Step 3 and 4).

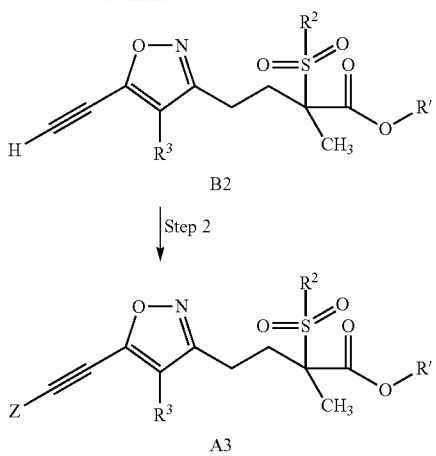

Scheme A

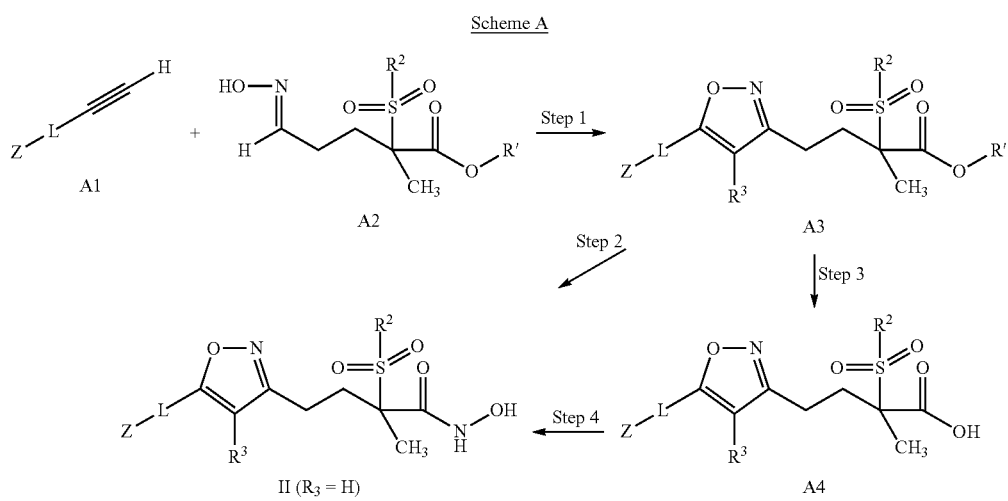

Scheme B illustrates an alternative method for the preparation of isoxazole intermediate A3. Terminal alkyne B2 can be obtained by using buta-1,3-diyn-1-yltrimethylsilane B1 as the cycloaddition partner. Various Z groups can be appended by standard transition metal catalyzed coupling reactions.

A general method to synthesize compounds of Formula (III) is depicted in Scheme C. Aldo reaction between N-Boc glycine methyl ester C1 and aldehyde C2 afforded adduct C3. The t-butyloxylcarbonyl group was cleaved under acid condition to provide primary amine C4, which can be coupled with aldehyde C5 under reductive amination condition. The ester C6 can be converted to hydroxamic acid III via direct amide synthesis in the presence of hydroxylamine and a base.

Scheme B

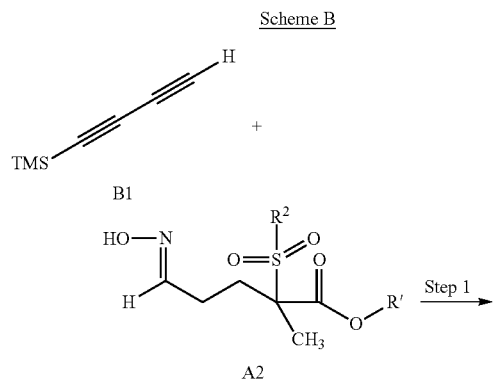

Scheme C

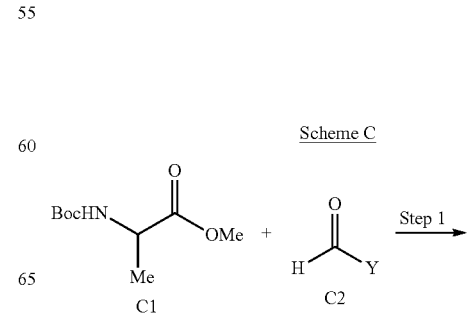

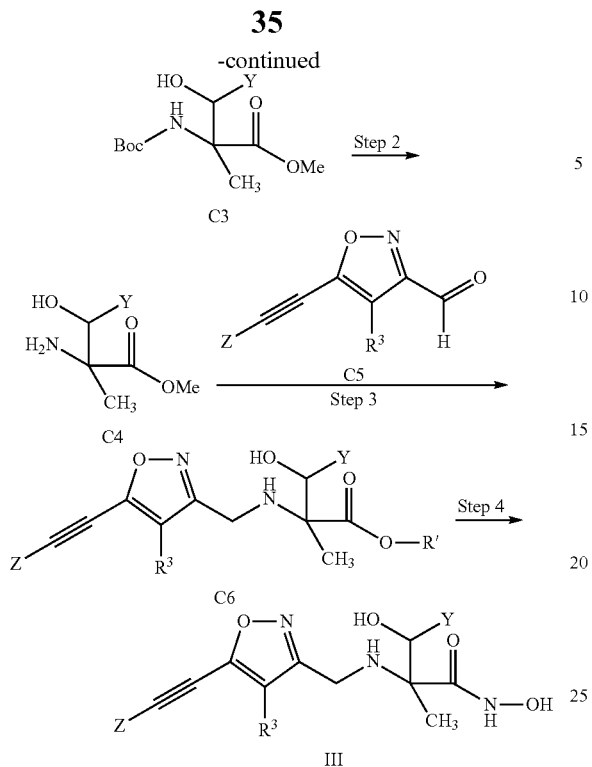

General Conditions:

Mass spectra were run on LC-MS systems using electrospray ionization. These were WATERS Acquity Single Quard Detector. [M+H]$^+$ refers to mono-isotopic molecular weights.

NMR spectra were run on open access Varian 400 or Varian 500 NMR spectrometers. Spectra were measured at 298K and were referenced using the solvent peak. Chemical shifts for $^1$H NMR are reported in parts per million (ppm).

Mass spectra were run on LC-MS systems with one of the following conditions:
 1. Waters Acquity UPLC-H class system equipped with SQD detector.
    Column: ACQUITY UPLC HSS C18 (50*2.1) mm, 1.8u.
    Column temperature: Ambient.
    Mobile Phase: A) 0.1% FA+5 mM Ammonium Acetate in Water.
      B) 0.1% FA in Acetonitrile.
    Gradient: 5-5% solvent B in 0.40 min, 5-35% solvent B in 0.80 min, 35-55% solvent B in 1.2 min, 55-100% solvent B in 2.5 min.
    Flow rate: 0.55 mL/min.
    Compounds were detected by a Waters Photodiode Array Detector.
 2. Waters LCMS system equipped with ZQ 2000 detector.
    Column: X-BRIDGE C18 (50*4.6) mm, 3.5u.
    Column temperature: Ambient.
    Mobile Phase: A) 0.1% NH3 in Water.
      B) 0.1% NH3 in Acetonitrile.
    Gradient: 5-95% solvent B in 5.00 min.
    Flow rate: 1.0 mL/min.
    Compounds were detected by a Waters Photodiode Array Detector.
 3. Waters ACQUITY UPLC system and equipped with a ZQ 2000 MS system.
    Column: Kinetex by Phenomenex, 2.6 um, 2.1×50 mm
    Column temperature: 50° C.

Gradient: 2-88% (or 00-45%, or 65-95%) solvent B over a 1.29 min period
    Flow rate: 1.2 mL/min.
    Compounds were detected by a Waters Photodiode Array Detector.

I.1. Synthesis of (R)-4-(5-(cyclopropylethynyl)isoxazol-3-yl)-N-hydroxy-2-methyl-2-(methylsulfonyl)butanamide [1.1]

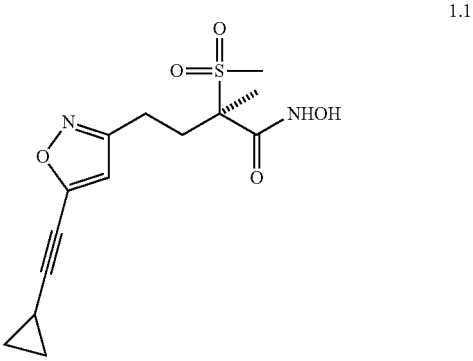

Method A

Step 1. Synthesis of (cyclopropylbuta-1,3-diyn-1-yl)trimethylsilane [1.1a]

To a solution of (bromoethynyl)cyclopropane (60 g, 414 mmol) in piperidine (345 ml) at 0° C. was added ethynyltrimethylsilane (44.7 g, 455 mmol) and CuI (7.88 g, 41.4 mmol). The solution was then stirred at rt for 2 hours. The reaction was quenched by adding sat. aq. NH$_4$Cl solution and then extracted with TBME. The organic layer was washed with water, brine, dried over MgSO$_4$ and concentrated. The crude material was purified by silica gel column chromatography, heptane as eluant to give product (42 g, 62% yield). $^1$H NMR (400 MHz, CDCl$_3$) 0.13-0.24 (m, 9H) 0.72-0.91 (m, 4H) 1.25-1.36 (m, 1H)

Step 2. Synthesis of ethyl 5-chloro-5-(hydroxyimino)-2-methyl-2-(methylsulfonyl)pentanoate [1.1b]

NCS (10.8 g, 81 mmol, 1.2 equiv) was added to a solution of ethyl 5-(hydroxyimino)-2-methyl-2-(methylsulfonyl)pentanoate (17 g, 67.6 mmol) in DMF (34 mL) and the resulting mixture was stirred at rt for 3 hours. The solvent was then removed under vacuum. The residue was dissolved in EtOAc, washed with water, brine, dried over Na$_2$SO$_4$ and concentrated to afford product (19 g, 98% yield). The crude material was continued to the next step with no further purification. LCMS (m/z): 286.2 [M+H]$^+$.

Step 3. Synthesis of (R)-ethyl 4-(5-(cyclopropylethynyl)isoxazol-3-yl)-2-methyl-2-(methylsulfonyl)butanoate [1.1c]

To a solution of 1.1a (8.4 g, 51.8 mmol) in MeOH (25 mL) was added K$_2$CO$_3$ (14.3 g, 104 mmol) and the mixture was stirred at rt for 18 hours. The mixture was then diluted with CH$_2$Cl$_2$ (75 mL) and filtered. The filtrate was then placed in an ice-water bath and 1.1.b (14.79 g, 51.8 mmol) was added. TEA (14.43 ml, 104 mmol) was then added to the above solution over 30 mins and the mixture was stirred at rt for 4 hours. The solvent was removed under reduced pressure. The residue was diluted with TBME and washed with water, brine, dried over Na$_2$SO$_4$ and concentrated. The residue was purified by silica gel column chromatography, EtOAc/heptane 0 to 60%, to give (±)-1.1c (9.0 g, 51%). The two enantiomers were separated by chiral HPLC.

Separation condition: Chiral AD column; flow rate: 30 ml/min; solvent: Heptane/EtOH=50/50; pressure 1263 psi. Product 1: tR 3.76 min, product 2: tR 4.73 min. Product 2 is the desired isomer 1.1c (3.0 g). $^1$H NMR (400 MHz, CDCl$_3$) 0.84-1.08 (m, 4H) 1.32 (t, J=7.14 Hz, 3H) 1.45-1.56 (m, 2H) 1.68 (s, 3H) 2.17 (s, 1H) 2.25-2.40 (m, 1H) 2.53-2.71 (m, 2H) 2.80 (d, J=5.04 Hz, 1H) 3.05 (s, 3H) 4.27 (q, J=7.11 Hz, 2H) 6.17 (s, 1H). LCMS (m/z): 340.3 [M+H]$^+$.

Step 4. Synthesis of (R)-4-(5-(cyclopropylethynyl)isoxazol-3-yl)-2-methyl-2-(methylsulfonyl)butanoic acid [1.1d]

LiOH.H$_2$O (0.3 g, 2.0 mmol) was added to a solution of 1.1c (1.2 g, 3.5 mmol) in THF/MeOH/water (12 mL, 1/1/1) and the resulting solution was stirred at rt for 1 hour. The solvent was then removed under reduced pressure. The remaining material was acidified with 3.0 N HCl aq. solution and extracted with EtOAc. The organic layer was washed with brined, dried over Na$_2$SO$_4$ and concentrated to give product (1.1 g, quantitative yield). The crude material was continued to the next step with no further purification. LCMS (m/z): 312.3 [M+H]$^+$.

Step 5. Synthesis of (2R)-4-(5-(cyclopropylethynyl)isoxazol-3-yl)-2-methyl-2-(methylsulfonyl)-N-((tetrahydro-2H-pyran-2-yl)oxy)butanamide [1.1e]

To a solution of 1.1d (1.1 g, 3.53 mmol) in DMF (6 mL) at rt was added aza-HOBt (0.866 g, 6.36 mmol), EDC (1.016 g, 5.30 mmol), and O-(tetrahydro-2H-pyran-2-yl)hydroxylamine (0.621 g, 5.30 mmol), TEA (1.477 ml, 10.60 mmol). The solution was stirred at 45° C. for 3 hours then rt for 18 hours. The solvent was removed under reduced pressure. The residue was diluted with EtOAc, washed with sat. aq. NaHCO$_3$ solution. The organic layer was washed with brine, dried over Na$_2$SO$_4$ and concentrated. The residue was purified by silica gel column chromatography, EtOAc/heptane 0 to 70% to give product 1.2 g (83% yield). LCMS (m/z): 411.3 [M+H]$^+$.

Step 6. Synthesis of (R)-4-(5-(cyclopropylethynyl)isoxazol-3-yl)-N-hydroxy-2-methyl-2-(methylsulfonyl)butanamide [1.1]

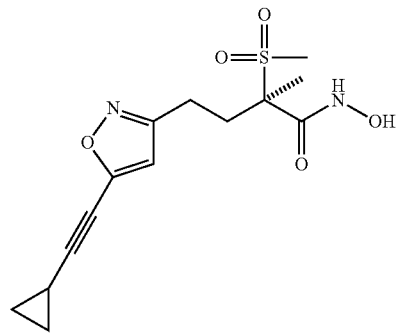

1.1

To a solution of 1.1e (1.2 g, 2.92 mmol) in MeOH (5.0 mL) and DCM (5.0 mL) at 0° C. was added HCl (0.731 mL, 4.0 M in dioxane, 2.92 mmol). The solution was stirred at rt for 1 hour. The solvent was then removed under reduced pressure. The remaining material was purified by silica gel column chromatography, acetone/heptane 0 to 60% to give product 0.79 g (81% yield). $^1$H NMR (400 MHz, DMSO): 10.97 (s, 1H), 9.24 (s, 1H), 6.73 (s, 1H), 3.06 (s, 3H), 2.71 (dd, J=17.3, 9.1 Hz, 1H), 2.56 (d, J=4.0 Hz, 1H), 2.47-2.40 (m, 1H), 2.06-1.95 (m, 1H), 1.69 (ddd, J=13.3, 8.3, 5.0 Hz, 1H), 1.50 (s, 3H), 0.99 (td, J=6.8, 4.0 Hz, 2H), 0.88-0.82 (m, 2H). LCMS (m/z): 327.3 [M+H]$^+$.

Method B

Alternative Synthesis of 1.1c

Step 7. Synthesis of ethyl 2-methyl-2-(methylsulfonyl)hex-5-enoate [1.1f]

To a solution of ethyl 2-(methylsulfonyl)propanoate (50 g, 277 mmol) in DMF (277 ml) at 0° C. was added NaH (14.43 g, 60%, 361 mmol) and the mixture was stirred at rt for 2 hours. The mixture was then cooled at 0° C. and 4-bromobut-1-ene (41.2 g, 305 mmol) was added over 30 mins. The mixture was then stirred at rt for 18 hours. The solvent was removed under high vacuum. To the residue was added TBME and then quenched with sat. aq. NH$_4$Cl solution. The phases were separated and the aqueous layer was extracted with TBME. The combined organic layer was washed with brine and concentrated. The residue was purified by silica gel column chromatography, EtOAc/heptane 0 to 50% to give product. $^1$H NMR (400 MHz, CDCl$_3$): 1.32 (t, J=7.14 Hz, 3H) 1.62 (s, 3H) 1.91-2.06 (m, 2H) 2.12-2.42 (m, 2H) 3.04 (s, 3H) 4.28 (q, J=7.14 Hz, 2H) 4.92-5.14 (m, 2H) 5.64-5.86 (m, 1H)

Step 8. Separation of 1.1f to Provide 1.1f-I and 1.1f-II

The racemic material 1.1f was separated into enantiomer 1.1f-I and 1.1f-II by simulated moving bed chromatography.

| | |
|---|---|
| Instrumentation | BAYCC50 SMB unit |
| Flow rate | Eluent: 13.58 L/h |
| | Feed: 0.53 L/h |
| | Extract: 11.2 L/h |
| | Raffinate: 2.9 L/h |
| | Recycle: 24.00 L/h |
| Mobile phase | Heptane:EtOH 80:20 |
| Column | Chiralpak AD 20 uM 8 × (100 × 50 mm) |
| Switch time | 71 sec |
| Temperature | 25° C. |
| Peak 1 | 5.5 min |
| Peak 2 | 8.9 min |

The second peak is the desired isomer ethyl (R)-2-methyl-2-(methylsulfonyl)hex-5-enoate 1.1f-II.

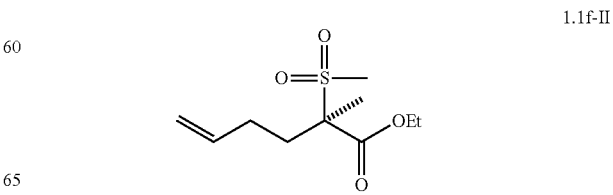

1.1f-II

Step 9. Synthesis of ethyl (R)-2-methyl-2-(methylsulfonyl)-5-oxopentanoate [1.1g]

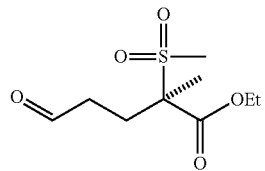

1.1g

To a solution of 1.1f-II (6 g, 25.6 mmol) in dioxane (128 mL) and water (43 mL) was added 2,6-lutidine (5.49 g, 51.2 mmol) and OsO$_4$ (3.25 g, 4% in water, 0.512 mmol). After 30 mins, the solution was placed in an ice water bath and NaIO$_4$ (21.91 g, 102 mmol) was added. The mixture was then stirred at rt for 18 hours. The mixture was then filtered and the filtrate was concentrated. The residue was dissolved in EtOAc and washed with 1.0 HCl aq solution, brine, dried over Na$_2$SO$_4$ and concentrated. The crude material was continued to the next step with no further purification. $^1$H NMR (400 MHz, Solvent): 1.32 (t, J=7.14 Hz, 3H) 1.61 (s, 3H) 2.22-2.36 (m, 1H) 2.43-2.62 (m, 2H) 2.63-2.76 (m, 1H) 3.07 (s, 3H) 4.28 (q, J=7.14 Hz, 2H) 9.69-9.92 (m, 1H)

Step 10. Synthesis of ethyl (R)-5-(hydroxyimino)-2-methyl-2-(methylsulfonyl)pentanoate [1.1 h]

To a solution of hydroxylamine hydrochloride (2.0 g, 28.2 mmol) in Water (26 mL) was added NaHCO$_3$ (2.4 g). After stirring at rt for 10 mins, a solution of 1.1g (6.0 g, 25 mmol) in EtOH (26 mL) was added and the solution was stirred at rt for 18 hours. The solvent was removed under reduced pressure. The remaining material was extracted with EtOAc. The organic layer was washed with brine, dried over Na$_2$SO$_4$ and concentrated to give product 6.4 g. The crude material was continued to the next step with no further purification. LCMS (m/z): 252.1 [M+H]$^+$.

Step 11. Synthesis of Synthesis of (R)-ethyl 4-(5-(cyclopropylethynyl)isoxazol-3-yl)-2-methyl-2-(methylsulfonyl)butanoate [1.1c]

Compound 1.1c was synthesized from 1.1h by the procedure of example 1.1 step 2-3. The chiral separation in step 3 is unnecessary since 1.1h is enantiomerically pure.

I.2. Synthesis of (R)-4-(5-(cyclobutylethynyl)isoxazol-3-yl)-N-hydroxy-2-methyl-2-(methylsulfonyl)butanamide [1.2]

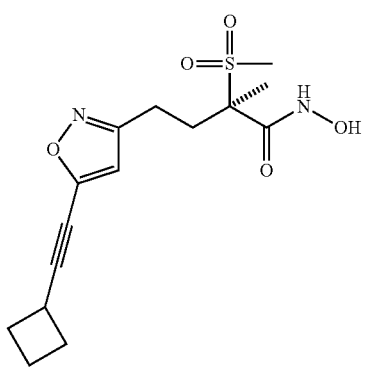

1.2

Step 1. Synthesis of (iodoethynyl)cyclobutane [1.2a]

n-BuLi (53.6 mL, 2.5M in hexane, 86 mmol) was added to a solution of 6-chlorohex-1-yne (5.21 mL, 42.9 mmol) in THF (107 mL) at −78° C. and the resulting solution was stirred at rt for 24 hours. Iodine (10.88 g, 42.9 mmol) was then added and the solution was stirred at rt for 3 hours. The solvent was removed under reduced pressure and the residue was partitioned between TBME and water. The organic layer was washed with brine, dried over Na$_2$SO$_4$ and concentrated. The residue was purified by silica gel column chromatography, heptane 100%, to give product 3.4 g (38% yield). $^1$H NMR (400 MHz, CDCl$_3$) 1.79-1.96 (m, 2H) 2.08-2.31 (m, 4H) 3.16 (m, 1H)

Step 2. Synthesis of (cyclobutylbuta-1,3-diyn-1-yl)trimethylsilane [1.2b]

A flask was charged with piperidine (11 mL) and degassed. At 0° C., 1a (2.8 g, 13.59 mmol) was added followed by CuI (0.259 g, 1.359 mmol) and ethynyltrimethylsilane (1.468 g, 14.95 mmol). The mixture was stirred at 0° C. for 1 hour and at rt for 1 hour. The mixture was diluted with TBME and washed with sat. aq. NH$_4$Cl solution, brine and concentrated. The residue was purified by silica gel column chromatography, heptane 100%, to give product 1.7 g (yield 71%). $^1$H NMR (400 MHz, CDCl$_3$): 0.12-0.28 (m, 9H), 1.92 (m, 2H), 2.09-2.33 (m, 4H), 3.06 (m, 1H)

Step 3. Synthesis of (R)-benzyl 2-methyl-2-(methylsulfonyl)pent-4-enoate [1.2c]

Into a 20-L 4-necked round-bottom flask, purged and maintained with an inert atmosphere of nitrogen, was placed benzyl 2-methanesulfonylpropanoate (960 g, 3.96 mol, 1.00 equiv), CH$_3$CN (14.4 L), and Cs$_2$CO$_3$ (2585 g, 7.93 mol, 2.00 equiv). This was followed by the addition of 3-bromoprop-1-ene (667 g, 5.51 mol, 1.40 equiv) dropwise with stirring at 0° C. in 30 mins. The resulting solution was stirred for overnight at room temperature. The solids were filtered out. The solids were washed with EtOAc and the organic layers were combined. The resulting mixture was concentrated under vacuum. The residue was applied onto a silica gel column with ethyl acetate/petroleum ether (1:15) to afford product 860 g (77%). $^1$H NMR (300 MHz, CDCl$_3$): 1.61 (s, 3H), 2.56-2.63 (m, 1H), 2.97-3.05 (m, 4H), 5.13-5.28 (m, 4H), 5.54-5.68 (m, 1H), 7.34-7.41 (m, 5H). LCMS (m/z): 283 [M+H]$^+$.

The material was separated by simulated moving bed chromatography:
Column: CHIRALPAK AY-PREP
Solvent: Heptane/EtOH 50/50
Flow: 1.0 mL/min
Engine: Agilent 1200 DAD Magellan
The first peak is the desired enantiomer 1.2c, tR 6.9 min.
The second peak is the undesired enantiomer: tR 9.6 min.

Step 4. Synthesis of (R)-benzyl 5-hydroxy-2-methyl-2-(methylsulfonyl)pentanoate [1.2d]

To a solution of 1.2c (10 g, 35.4 mmol) in THF (38 mL) at 0° C. was added BH$_3$.THF complex (39.0 mL, 1.0 M solution in THF, 39.0 mmol) and the solution was stirred at rt for 30 mins. The solution was then placed in an ice-water bath and H$_2$O$_2$ (10.85 mL, 30% in water, 177 mmol) was added over 10 mins while the internal temperature was kept below 10° C. Afterwards, a solution of NaOH aq solution (35.4 mL, 1.0 N, 35.4 mmol) was added over 5 mins. After stirring at 0° C. for 30 mins, the solution was diluted EtOAc. The phases were separated. The organic layer was washed with brine, dried over Na$_2$SO$_4$ and concentrated. The crude material was purified by silica gel column chromatography, EtOAc/heptane 0 to 100%, to give product 7.2 g (yield 67%). $^1$H NMR (400 MHz, CDCl$_3$): 1.13-1.70 (m, 4H), 1.80-2.31 (m, 2H), 3.01 (s, 3H), 3.62 (m, 2H), 5.25 (s, 2H), 7.29-7.44 (m, 5H). LCMS (m/z): 301.3 [M+H]$^+$.

Step 5. Synthesis of (R)-benzyl 2-methyl-2-(methylsulfonyl)-5-oxopentanoate [1.2e]

To a solution of oxalyl chloride (2.62 mL, 30.0 mmol) in DCM (82 mL) at −78° C. was added DMSO (4.25 mL, 59.9 mmol). After 10 mins, a solution of 1.2d (7.5 g, 24.97 mmol) in DCM (5 mL) was added and the resulting solution was stirred at −78° C. for 20 mins. TEA (13.92 mL, 100 mmol) was then added and the mixture was stirred at −78° C. for 10 mins before slowly warmed to 0° C. The reaction was then quenched by adding sat. aq. NH$_4$Cl solution. The phase were separated and the aqueous layer was extracted with DCM. The combined organic layer was washed with brine, dried over MgSO$_4$ and concentrated. The residue was purified by silica gel column chromatography, EtOAc/heptane 0 to 60% to afford product 5.3 g (yield 71%). LCMS (m/z): 299.3 [M+H]$^+$. $^1$H NMR (400 MHz, CDCl$_3$) 1.62 (s, 3H) 2.23-2.39 (m, 1H) 2.43-2.55 (m, 2H) 2.58-2.70 (m, 1H) 2.99 (s, 3H) 5.15-5.34 (m, 2H), 7.30-7.50 (m, 6H) 9.71 (s, 1H)

Step 6. Synthesis of (R)-benzyl 5-(hydroxyimino)-2-methyl-2-(methylsulfonyl)pentanoate [1.2f]

NaHCO$_3$ (1.6 g, 19.5 mmol) was added to a solution of hydroxylamine hydrochloride (1.36 g, 19.5 mmol) in water (30.0 mL). After stirring at rt for 10 mins, a solution of 1.2d (5.3 g, 17.7 mmol) in EtOH (30 mL) was added and the resulting solution was stirred at rt for 18 hours. The solvent was removed under reduced pressure and the remaining material was extracted with EtOAc. The organic layer was washed with brine, dried over MgSO$_4$ and concentrated. The crude material was continued to the next step with no further purification. LCMS (m/z): 314.5 [M+H]$^+$.

Step 7. Synthesis of (R)-4-(5-(cyclobutylethynyl)isoxazol-3-yl)-N-hydroxy-2-methyl-2-(methylsulfonyl)butanamide [1.2]

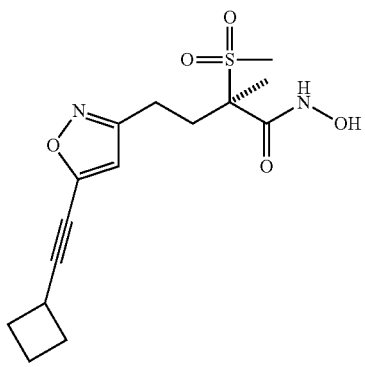

1.2

Compound 1.2 was synthesized from 1.2b and 1.2f by the process of Example 1.1 step 2-6. $^1$H NMR (500 MHz, DMSO-d6): 10.98 (s, 1H), 9.24 (s, 1H), 6.77 (s, 1H), 3.46-3.38 (m, 1H), 3.06 (s, 3H), 2.70-2.76 (m, 1H), 2.43-2.57 (m, 2H), 2.30-2.35 (m, 2H), 2.22-2.12 (m, 2H), 2.06-1.88 (m, 3H), 1.51 (s, 3H). LCMS (m/z): 341.3 [M+H]$^+$.

I.3. Synthesis of (R)-4-(5-(3,3-dimethylbut-1-yn-1-yl)isoxazol-3-yl)-N-hydroxy-2-methyl-2-(methylsulfonyl)butanamide [1.3]

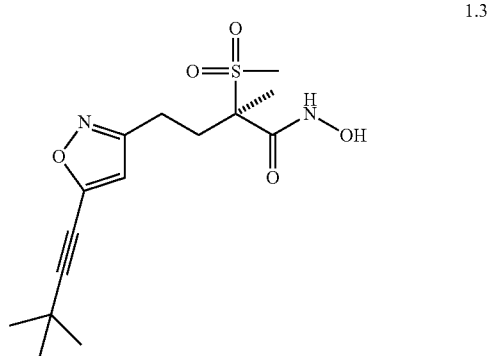 [SMILES: CC(C)(C)C#Cc1cc(CC[C@](C)(C(=O)NO)S(C)(=O)=O)no1]

1.3

Compound 1.3 was synthesized following the process of Example 1.2. $^1$H NMR (500 MHz, DMSO-d6): 1.31 (s, 9H), 1.51 (s, 3H), 1.84-2.10 (m, 1H), 2.36-2.58 (m, 2H), 2.67-2.80 (m, 1H), 3.34 (s, 3H), 6.76 (s, 1H), 9.12-9.31 (m, 1H), 10.89-11.04 (m, 1H). LCMS (m/z): 343.3 [M+H]$^+$.

I.4. Synthesis of (R)—N-hydroxy-2-methyl-2-(methylsulfonyl)-4-(5-(prop-1-yn-1-yl)isoxazol-3-yl)butanamide [1.4]

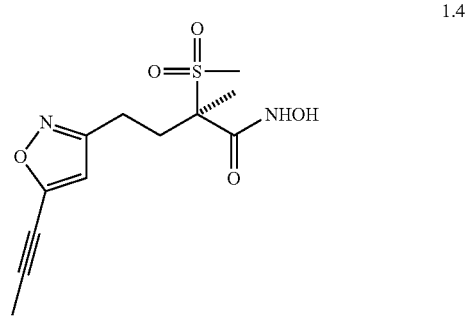

1.4

Compound 1.4 was synthesized following the process of Example 1.1 method B. The intermediate trimethyl(penta-1,3-diyn-1-yl)silane was synthesized as described in *Tetrahedron Lett.* 1980, 21, 3111. $^1$H NMR (400 MHz, DMSO): 1.49 (s, 3H); 1.93-2.03 (m, 1H); 2.15 (s, 3H); 2.39-2.45; (m, 1H); 2.51-2.55 (m, 1H); 2.64-2.78 (m, 1H); 3.03 (s, 3H; 6.45-7.09 (m, 1H); 8.96-9.65 (m, 1H); 10.75-11.32 (m, 1H). LCMS (m/z): 300.1 [M+H]$^+$.

I.5. Synthesis of (R)-4-(5-(but-1-yn-1-yl)isoxazol-3-yl)-N-hydroxy-2-methyl-2-(methylsulfonyl)butanamide [1.5]

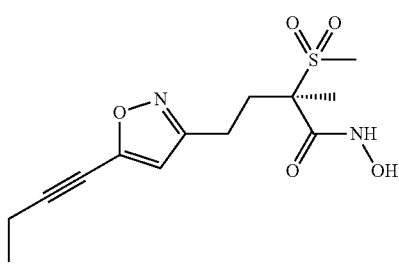

Compound 1.5 was synthesized following the process of Example 1.1 method B. The intermediate hexa-1,3-diyn-1-yltrimethylsilane was synthesized as described in *Tetrahedron Lett.* 1980, 21, 3111. $^1$H NMR (400 MHz, CD$_3$OD): 1.20-1.24 (t, 3H) 1.60 (s, 3H) 2.07-2.10 (m, 2H) 2.44-2.52 (m, 1H) 2.60-2.701.90-2.11 (m, 2H) 2.78-2.83 (m, 1H) 3.03 (s, 3H) 6.42 (s, 3H). LCMS (m/z): 315.2 [M+H]$^+$.

I.6. Synthesis of (R)—N-hydroxy-2-methyl-4-(5-(3-methylbut-1-yn-1-yl)isoxazol-3-yl)-2-(methylsulfonyl)butanamide [1.6]

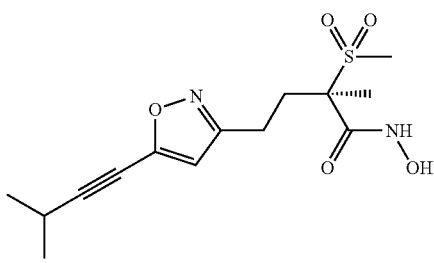

Compound 1.6 was synthesized following the process of Example 1.1 method B. $^1$H NMR (400 MHz, DMSO-d6): 1.11-1.25 (m, 6H) 1.40-1.55 (m, 3H) 1.88-2.09 (m, 1H) 2.37-2.58 (m, 4H) 2.63-2.80 (m, 1H) 2.82-2.96 (m, 1H) 3.03 (s, 3H) 6.73 (s, 1H) 10.93 (br. s., 1H). LCMS (m/z): 329.3 [M+H]$^+$.

I.7. Synthesis of (R)—N-hydroxy-2-methyl-2-(methylsulfonyl)-4-(5-(pent-1-yn-1-yl)isoxazol-3-yl)butanamide [1.7]

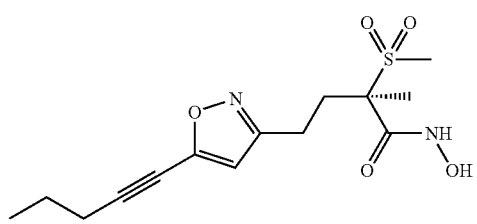

Compound 1.7 was synthesized following the process of Example 1.1 method B. The intermediate hepta-1,3-diyn-1-yltrimethylsilane was synthesized as described in *Tetrahedron* 2004, 60, 11421.

$^1$H NMR (500 MHz, DMSO-d$_6$): 1.00 (t, J=7.39 Hz, 4H) 1.46-1.55 (m, 4H) 1.55-1.65 (m, 3H) 2.03 (s, 1H) 2.37-2.50 (m, 1H) 2.59-2.68 (m, 1H) 2.68-2.81 (m, 1H) 3.07 (s, 2H) 6.69-6.84 (m, 1H). LCMS (m/z): 329.2 [M+H]$^+$.

I.8. Synthesis of (R)—N-hydroxy-2-methyl-4-(5-((1-methylcyclopropyl)ethynyl)isoxazol-3-yl)-2-(methylsulfonyl)butanamide [1.8]

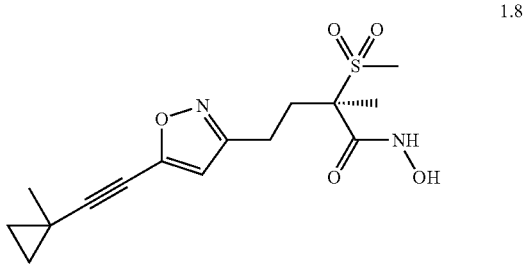 [SMILES: CC1(C#Cc2cc(CC[C@](C)(C(=O)NO)S(C)(=O)=O)no2)CC1]

Step 1: Synthesis of Trimethyl((1-methylcyclopropyl)buta-1,3-diyn-1-yl)silane [1.8a]

To a solution of (cyclopropylbuta-1,3-diyn-1-yl)trimethylsilane (600 mg, 3.70 mmol) in Et$_2$O (5 mL) was added dropwise BuLi (1.479 mL, 3.70 mmol) at 0° C., and the reaction mixture, was stirred at ambient temperature for 6 hours. Then dimethyl sulfate (0.883 mL, 9.24 mmol) was added dropwise at −10° C., the resulting solution was stirred at 10° C. and then at 20° C. for 30 min each. The reaction was quenched by adding sat. aq. NH4Cl, and the mixture then stirred at ambient temp. for 1 h. The aqueous phase was extracted with diethyl ether (20 mL), and the combined organic layers were washed with brine solution (10 mL) and H$_2$O (10 mL), dried (MgSO4) and concentrated. The crude product was purified by silica gel column chromatography, heptane 100%, to give product. (470 mg, 72.1% yield)

Step 2: Synthesis of 1-(buta-1,3-diyn-1-yl)-1-methylcyclopropane [1.8 b]

To trimethyl((1-methylcyclopropyl)buta-1,3-diyn-1-yl)silane (200 mg, 1.134 mmol) was added THF (1 mL), MeOH (0.5 mL), then followed by NaOH (0.681 mL, 3.40 mmol) The resultant mixture was stirred for 2 hour. The mixture was diluted with 3 mL of DCM, dried over Na$_2$SO$_4$, filtered, and the filtered solution was used immediately at the next step.

Step 3: Synthesis of (R)—N-hydroxy-2-methyl-4-(5-((1-methylcyclopropyl)ethynyl)isoxazol-3-yl)-2-(methylsulfonyl)butanamide [1.8]

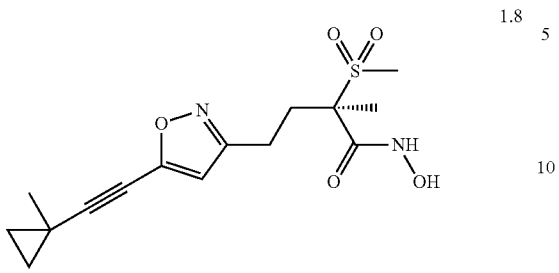

Compound 1.8 was synthesized following the process of Example 1.1 method B. $^1$H NMR (400 MHz, DMSO-d6): 0.70-1.09 (m, 5H) 1.21-1.57 (m, 7H) 1.88-2.11 (m, 1H) 2.34-2.56 (m, 3H) 2.59-2.80 (m, 1H) 2.93-3.10 (m, 3H) 6.59-6.84 (m, 1H) 10.93 (br. s., 1H). LCMS (m/z): 341.2 [M+H]$^+$.

I.9. Synthesis of (R)-4-(5-(5-fluorobut-1-yn-1-yl)isoxazol-3-yl)-N-hydroxy-2-methyl-2-(methylsulfonyl)butanamide [1.9]

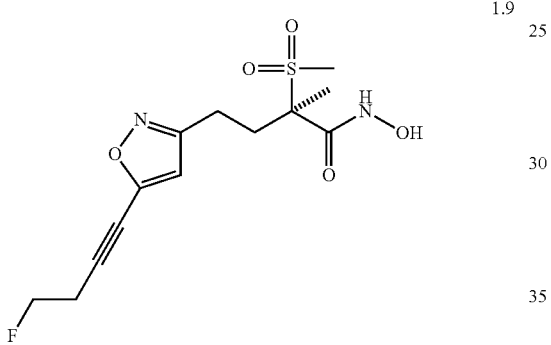

Compound 1.9 was synthesized following the process of Example 1.2. $^1$H NMR (400 MHz, DMSO-d$_6$) 10.95 (s, 1H), 9.22 (s, 1H), 6.81 (s, 1H), 4.60 (dt, J=46.8, 5.8 Hz, 2H), 3.05 (s, 3H), 3.05-2.92 (m, 2H), 2.79-2.64 (m, 1H), 2.51-2.39 (m, 2H), 2.15-1.93 (m, 1H), 1.51 (s, 3H). LCMS (m/z): 333.1 [M+H]$^+$.

I.10 Synthesis of (R)-4-(5-(5-fluoropent-1-yn-1-yl)isoxazol-3-yl)-N-hydroxy-2-methyl-2-(methylsulfonyl)butanamide [1.10]

Step 1. Synthesis of (2R)-4-(5-(5-hydroxypent-1-yn-1-yl)isoxazol-3-yl)-2-methyl-2-(methylsulfonyl)-N-((tetrahydro-2H-pyran-2-yl)oxy)butanamide [1.10a]

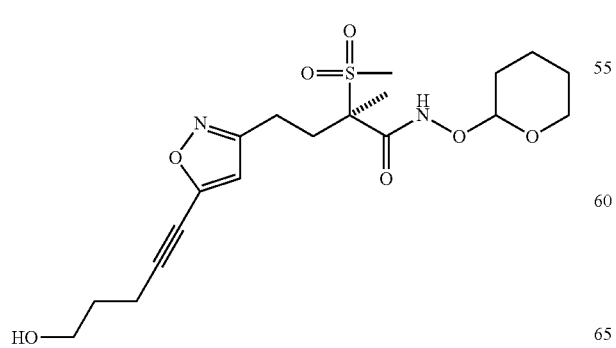

Compound 1.10a was synthesized from pent-4-yn-1-ol by the process of Example 1.1.

LCMS (m/z): 345.2 [M+H-THP]$^+$.

Step 2. Synthesis of (2R)-4-(5-(5-fluoropent-1-yn-1-yl)isoxazol-3-yl)-2-methyl-2-(methylsulfonyl)-N-((tetrahydro-2H-pyran-2-yl)oxy)butanamide [1.10b]

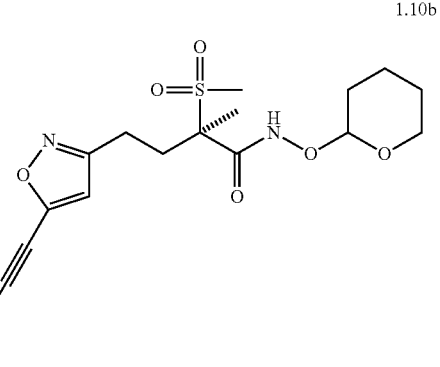

To a stirring solution of 1.10a (80 mg, 0.19 mmol) at 0° C. in DCM (2 mL) was added DAST (0.05 mL, 0.37 mmol). After completion of the reaction (1.5 hour), the mixture was diluted with DCM and washed with water, brine, dried over Na$_2$SO$_4$ and concentrated. The residue was purified by silica gel column chromatography (EtOAc/heptane, 40% to 100%) to give product 1.10b (11.5 mg, yield 14%). LCMS (m/z): 347.2 [M-THP+H]$^+$.

Step 3. (R)-4-(5-(5-fluoropent-1-yn-1-yl)isoxazol-3-yl)-N-hydroxy-2-methyl-2-(methylsulfonyl)butanamide [1.10]

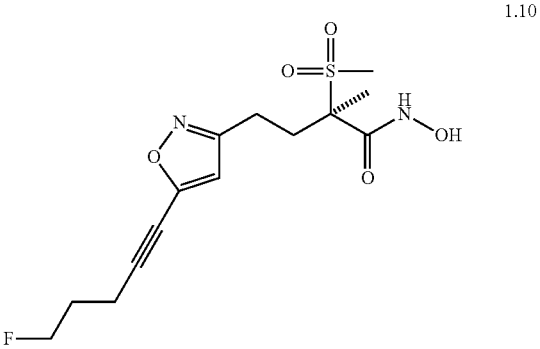 [SMILES: C[C@@](CCc1cc(C#CCCCF)on1)(C(=O)NO)S(C)(=O)=O]

Compound 1.10 was synthesized from 1.10b following the process of Example 1.1 Step 6. $^1$H NMR (400 MHz, DMSO-d$_6$) 10.95 (s, 1H), 9.21 (s, 1H), 6.78 (s, 1H), 4.54 (dt, J=47.3, 5.8 Hz, 2H), 3.05 (s, 3H), 2.75-2.67 (m, 1H), 2.64 (t, J=7.1 Hz, 2H), 2.52-2.43 (m, 2H), 2.05-1.88 (m, 3H), 1.51 (s, 3H). LCMS (m/z): 347.2 [M+H]$^+$.

I.11 Synthesis of Compound 1.11

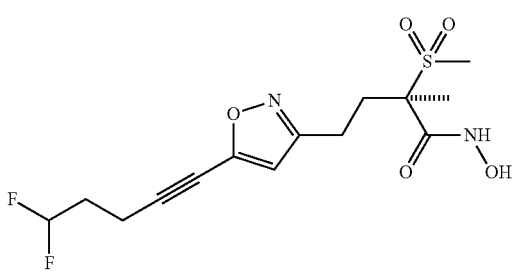

Step 1: Synthesis of (R)-Benzyl 4-(5-(5-hydroxy-pent-1-yn-1-yl)isoxazol-3-yl)-2-methyl-2-(methyl-sulfonyl)butanoate [1.11a]

Compound 1.11a was synthesized from pent-4-yn-1-ol by the process of Example 1.1. LCMS (m/z): 420.1 [M+H]$^+$.

Step 2: Synthesis of (R)-Benzyl 2-methyl-2-(methylsulfonyl)-4-(5-(5-oxopent-1-yn-1-yl)isoxazol-3-yl)butanoate [1.11b]

To a solution of 1.11a (100 mg, 0.238 mmol) in DCM (0.9 mL) at 0° C. was added DIPEA (0.200 mL, 1.14 mmol), followed by a solution of Py.SO$_3$ (114 mg, 0.715 mmol) in DMSO (0.3 mL). The solution was stirred at 0° C. for 30 min and then quenched by adding saturated aqueous NH$_4$Cl solution. The mixture was with EtOAc. The combined organics were washed with brine, dried over Na$_2$SO$_4$, filtered, and concentrated. The crude material was purified by silica gel column chromatography (EtOAc/heptane 40 to 90%) to give product (73 mg, 73.4% yield). LCMS (m/z): 418.3 [M+H]$^+$.

Step 3: Synthesis of (R)-Benzyl 4-(5-(5,5-difluoro-pent-1-yn-1-yl)isoxazol-3-yl)-2-methyl-2-(methyl-sulfonyl)butanoate [1.11c]

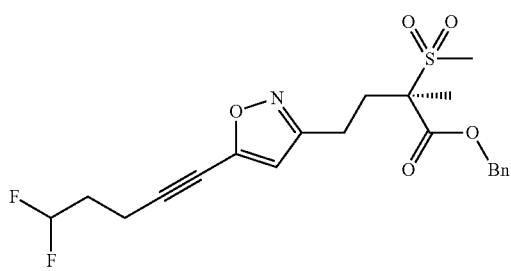

To a solution of 1.11b (73 mg, 0.175 mmol) in DCM (0.6 mL) was added DAST (0.069 mL, 0.525 mmol) at ambient temperature and the resulting solution was stirred for 1 hour. The reaction was quenched by adding saturated aqueous NaHCO$_3$ and the mixture was extracted with EtOAc. The combined organic layers were dried over sodium sulfate, filtered, and concentrated. The residue was purified by silica gel column chromatography (EtOAc/heptane, 10-70%) to give product (67 mg, 87% yield). LCMS (m/z): 440.3 [M+H]$^+$.

Steps 4: Synthesis of (R)-4-(5-(5,5-Difluoropent-1-yn-1-yl)isoxazol-3-yl)-N-hydroxy-2-methyl-2-(methylsulfonyl)butanamide [1.11]

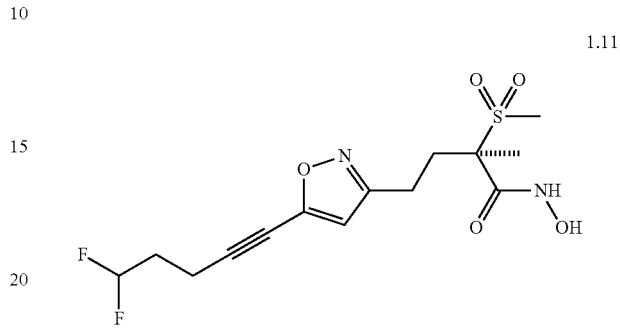

Compound 1.11 was synthesized from 1.11c by the process of Example 1.1 Steps 4-6. $^1$H NMR (400 MHz, CD$_3$OD): 6.54 (s, 1H) 5.86-6.22 (m, 1H) 3.08 (s, 3H) 2.78-2.90 (m, 1H) 2.58-2.77 (m, 4H) 2.09-2.29 (m, 3H) 1.65 (s, 3H). LCMS (m/z): 365.2 [M+H]$^+$.

I.12. Synthesis of (R)-4-(5-((3,3-difluorocyclobutyl)ethynyl)isoxazol-3-yl)-N-hydroxy-2-methyl-2-(methylsulfonyl)butanamide [1.12]

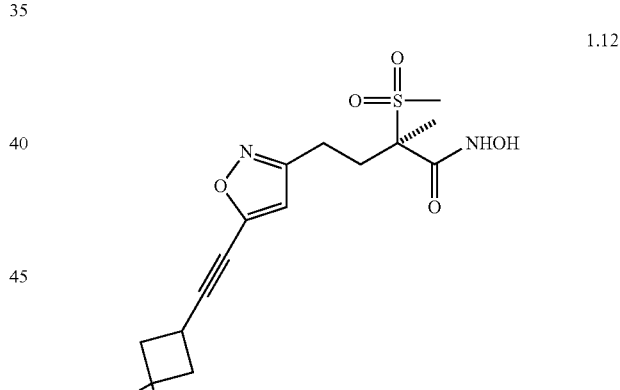

Step 1. Synthesis of (3-((tert-butyldimethylsilyl)oxy)cyclobutyl)methanol [1.12a]

A solution of LiAlH$_4$ in THF (77 ml, 1.0 M in THF, 1.1 equiv) was added dropwise to a solution of methyl 3-((tert-butyldimethylsilyl)oxy)cyclobutane-1-carboxylate (17 g, 69.6 mmol) in THF (139 ml) at 0° C. and the resulting solution was stirred at rt for 2 hours. The reaction mixture was then cooled in ice-water bath and quenched by adding sat. aq. Na$_2$SO$_4$ solution (10 ml). After stirred at rt for 30 mins, the mixture was filtered and the filtrate was concentrated. The residue was dissolved in EtOAc and dried over MgSO$_4$ and concentrated. The crude material was continued to the next step with no further purification.

Step 2. Synthesis of 3-((tert-butyldimethylsilyl)oxy)cyclobutane-1-carbaldehyde [1.12b]

To a solution of oxalyl chloride (5.8 ml, 66.5 mmol, 1.2 equiv) in DCM (165 mL) at −78° C. was added DMSO (9.4 ml, 133 mmol, 2.4 equiv). After stirred for 10 mins, a solution of (3-((tert-butyldimethylsilyl)oxy)cyclobutyl)methanol (12 g, 55.5 mmol) in DCM (20 ml) was added and the resulting solution was stirred at −78° C. for 20 mins. TEA (23 mL, 166 mmol, 3.0 equiv) was added and the mixture was stirred at −78° C. for 10 mins then slowly warmed to 0° C. The reaction was quenched by adding sat. aq. NH$_4$Cl solution. The phase were separated and the aqueous layer was extracted with DCM. The combined organic layer was washed with brine, dried over MgSO$_4$ and concentrated. The residue was purified by silica gel column chromatography, EtOAc/heptane 0 to 20%, to afford product 5.2 g (44% yield). $^1$H NMR: (400 MHz, CDCl$_3$) −0.2 (s, 6H), 0.8 (s, 9H), 1.94-2.27 (m, 2H), 2.48-2.65 (m, 2H), 2.93-3.15 (m, 1H), 4.17-4.50 (m, 1H), 9.8 (s, 1H).

Step 3. Synthesis of tert-butyl(3-ethynylcyclobutoxy)dimethylsilane [1.12c]

To a solution of 3-((tert-butyldimethylsilyl)oxy)cyclobutane-1-carbaldehyde (5.2 g, 24.2 mmol, 1.0 equiv) and dimethyl (1-diazo-2-oxopropyl)phosphonate (10.10 g, 48.5 mmol, 2.0 equiv) in MeOH (81 ml) at 0° C. was added K$_2$CO$_3$ (10.06 g, 72.8 mmol, 3.0 equiv) and the resulting mixture was stirred at rt for 18 hours. The mixture was filtered and the filtrate was concentrated. The residue was dissolved in EtOAc and washed with water, brine, dried over Na$_2$SO$_4$ and concentrated. The residue was purified by silica gel column chromatography, EtOAc/heptane 0 to 10%, to give product 4.0 g (78 yield). $^1$H NMR (400 MHz, CDCl$_3$): 0.04 (s, 6H), 0.88 (s, 9H), 2.1 (s, 1H), 2.18-2.51 (m, 4H) 2.80-3.04 (m, 1H) 4.30-4.73 (m, 1H)

Step 4. Synthesis of benzyl (R)-4-(5-((3-((tert-butyldimethylsilyl)oxy)cyclobutyl)ethynyl)isoxazol-3-yl)-2-methyl-2-(methylsulfonyl)butanoate [1.12d]

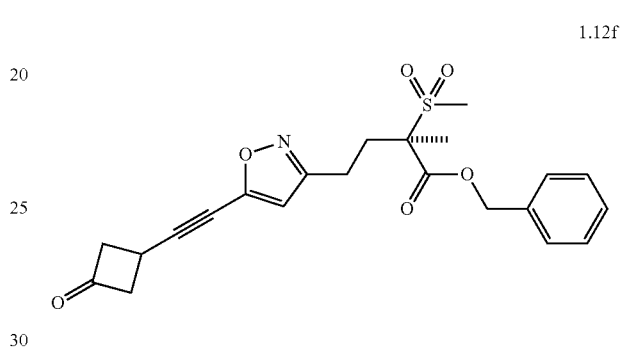

1.12d

Compound 1.12d was synthesized from 1.12c following the process of Example 1.1 method B. LCMS (m/z): 347.4 [M+H]$^+$.

Step 5. Synthesis of benzyl (R)-4-(5-((3-hydroxycyclobutyl)ethynyl)isoxazol-3-yl)-2-methyl-2-(methylsulfonyl)butanoate [1.12e]

TBAF solution (1.0 M in THF, 4.4 ml, 4.4 mmol, 1.5 equiv) was added to a solution of benzyl (R)-4-(5-((3-((tert-butyldimethylsilyl)oxy)cyclobutyl)ethynyl)isoxazol-3-yl)-2-methyl-2-(methylsulfonyl)butanoate (1.6 g, 2.93 mmol, 1.0 equiv) in THF (5.8 ml) at rt and the resulting solution was stirred at rt for 30 mins. The mixture was then loaded directly to silica gel and flushed with acetone/heptane 0 to 60%, to afford product 0.86 g (68% yield). $^1$H NMR (400 MHz, CDCl$_3$): 1.69 (s, 3H), 2.24-2.42 (m, 3H), 2.51-2.66 (m, 4H), 2.72-2.85, (m, 1H), 2.96 (s, 3H), 3.18-3.35 (m, 1H), 4.46-4.74 (m, 1H), 5.23 (m, 2H), 6.14 (s, 1H) 7.30-7.43 (m, 5H). LCMS (m/z): 432.6 [M+H]$^+$.

Step 6. Synthesis of benzyl (R)-2-methyl-2-(methylsulfonyl)-4-(5-((3-oxocyclobutyl)ethynyl)isoxazol-3-yl)butanoate [1.12f]

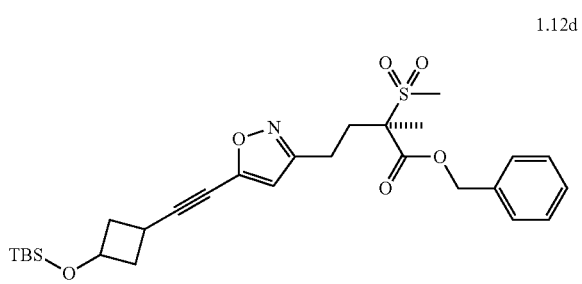

1.12f

To a solution of benzyl (R)-4-(5-((3-hydroxycyclobutyl)ethynyl)isoxazol-3-yl)-2-methyl-2-(methylsulfonyl)butanoate (230 mg, 0.533 mmol, 1.0 equiv) in DCM (2.0 ml) at 0° C. was added DIPEA (0.465 ml, 2.67 mmol, 5.0 equiv) and a solution of pyridine sulfur trioxide (255 mg, 1.6 mmol, 3.0 equiv) in DMSO (0.6 ml). After stirred at rt for 30 mins, the reaction was quenched by adding sat. aq. NaHCO$_3$ solution and then extracted with EtOAc. The organic layer was washed with brine, dried over Na$_2$SO$_4$ and concentrated. The residue was purified by silica gel column chromatography, acetone/heptane 0 to 50%, to afford product 200 mg (yield 87%). $^1$H NMR (400 MHz, CDCl$_3$): 1.70 (s, 3H), 2.26-2.40 (m, 1H), 2.55-2.68 (m, 2H), 2.78-2.87 (m, 1H), 2.96 (s, 3H), 3.29-3.68 (m, 5H), 5.24 (d, J=0.78 Hz, 2H), 6.20 (s, 1H), 7.38 (s, 5H). LCMS (m/z): 430.3 [M+H]$^+$.

Step 7. Synthesis of benzyl (R)-4-(5-((3,3-difluorocyclobutyl)ethynyl)isoxazol-3-yl)-2-methyl-2-(methylsulfonyl)butanoate [1.12g]

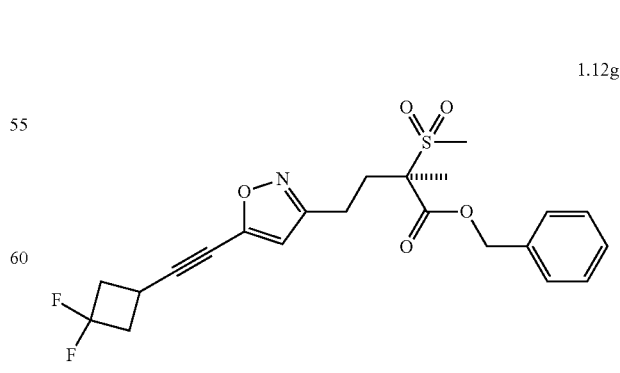

1.12g

To a solution of benzyl (R)-2-methyl-2-(methylsulfonyl)-4-(5-((3-oxocyclobutyl)ethynyl)isoxazol-3-yl)butanoate (170 mg, 0.396 mmol) in DCM (1.3 ml) at rt was added DAST (0.157 ml, 1.187 mmol, 3.0 equiv) and the resulting solution was stirred at rt for 18 hours. The reaction was quenched by adding sat. aq. NaHCO₃ solution and then extracted with EtOAc. The organic layer was washed with brine, dried over Na₂SO₄ and concentrated. The residue was purified by silica gel column chromatography, acetone/heptane 0 to 60%, to afford product 140 mg (78% yield). $^1$H NMR (400 MHz, CDCl₃): 1.70 (s, 3H); 2.23-2.41 (m, 1H); 2.54-2.68 (m, 2H); 2.74-2.88 (m, 3H); 2.96 (s, 3H); 2.99-3.06 (m, 2H); 3.11-3.27 (m, 1H); 5.12-5.43 (m, 2H); 6.19 (s, 1H); 7.37 (m, 5H). LCMS (m/z): 452.0 [M+H]⁺.

Step 8. Synthesis of (R)-4-(5-((3,3-difluorocyclobutyl)ethynyl)isoxazol-3-yl)-N-hydroxy-2-methyl-2-(methylsulfonyl)butanamide [1.12]

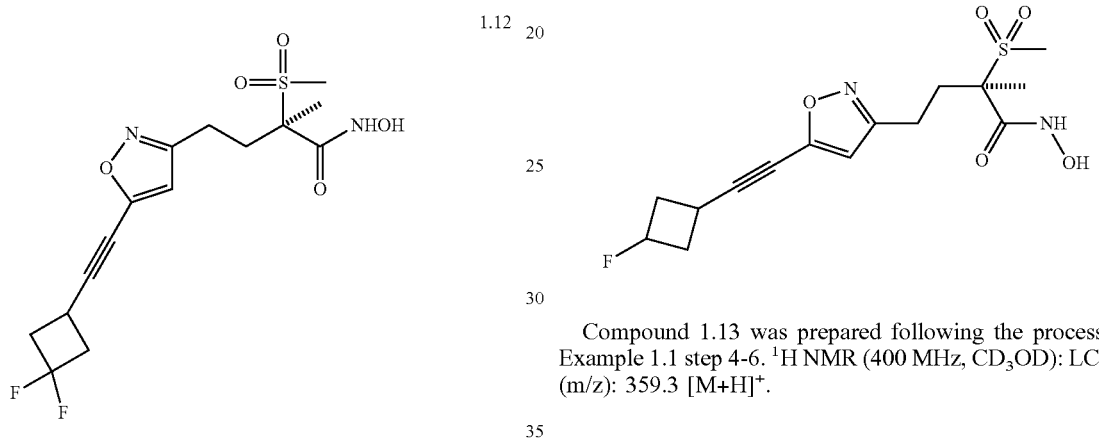

Compound 1.12 was synthesized following the process of Example 1.1 step 4-6. $^1$H NMR (400 MHz, DMSO): 1.49 (s, 3H); 1.94-2.04 (m, 1H); 2.4-2.51 (m, 1H); 2.63-2.84 (m, 4H); 3.03 (s, 3H); 3.05-3.14 (m, 2H); 3.34-3.47 (m, 1H); 5.53-5.95 (m, 1H); 6.63-6.94 (m, 1H); 8.98-9.56 (m, 1H). LCMS (m/z): 377.5 [M+H]⁺.

1.13. Synthesis of (R)-4-(5-((3-fluorocyclobutyl)ethynyl)isoxazol-3-yl)-N-hydroxy-2-methyl-2-(methylsulfonyl)butanamide [1.13]

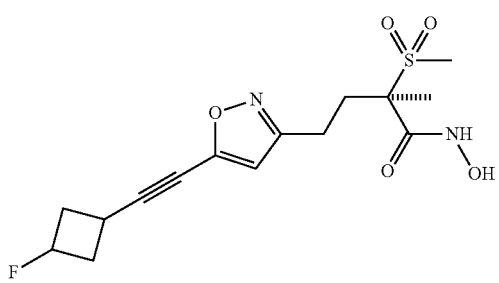 [SMILES: C[C@@](CCc1cc(C#CC2CC(F)C2)on1)(C(=O)NO)S(C)(=O)=O]

Step 1: (R)-benzyl 4-(5-((3-fluorocyclobutyl)ethynyl)isoxazol-3-yl)-2-methyl-2-(methylsulfonyl)butanoate [1.13a]

To a solution of 1.12e (55 mg, 0.13 mmol) in DCM (1.2 mL) was added DeoxoFluor, 50% in toluene (0.11 mL, 0.26 mmol) at 0° C. The reaction was stirred overnight while warming to ambient temperature. Additional DeoxoFluor, 50% in toluene (0.11 mL, 0.26 mmol) was added and the reaction was stirred for 24 hr. The reaction was quenched with ethanol (0.149 mL, 2.55 mmol), followed by aqueous pH 7 phosphate buffer, and extracted with EtOAc. The organic layer was washed with brine, dried over Na₂SO₄, filtered, and concentrated. The crude material was purified by flash chromatography over silica gel (EtOAc/heptane) to give product 16 mg (29.0% yield). LCMS (m/z): 434.3 [M+H]⁺.

Steps 2: (R)-4-(5-((3-fluorocyclobutyl)ethynyl)isoxazol-3-yl)-N-hydroxy-2-methyl-2-(methylsulfonyl)butanamide [1.13]

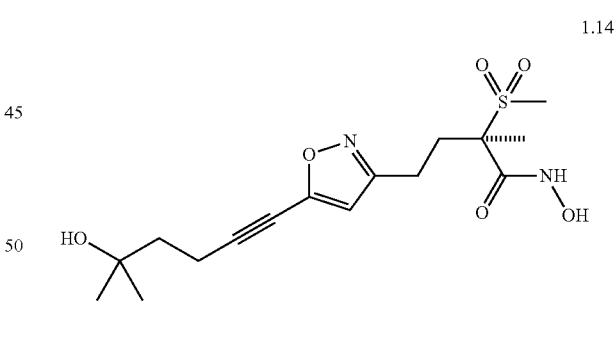

Compound 1.13 was prepared following the process of Example 1.1 step 4-6. $^1$H NMR (400 MHz, CD₃OD): LCMS (m/z): 359.3 [M+H]⁺.

1.14. Synthesis of (R)—N-hydroxy-4-(5-(5-hydroxy-5-methylhex-1-yn-1-yl)isoxazol-3-yl)-2-methyl-2-(methylsulfonyl)butanamide [1.14]

Step 1: Synthesis of 6-(Trimethylsilyl)hex-5-yn-2-one [1.14a]

To a stirred solution of dichloro(p-cymene)ruthenium(II) dimer (0.919 g, 1.50 mmol) in benzene (150 mL) was added pyrrolidine (0.496 mL, 6.00 mmol) and the mixture was then stirred for 30 min at ambient temperature. TMS-acetylene (4.24 mL, 30.0 mmol) and methyl vinyl ketone (7.38 mL, 90.0 mmol) were added. After stirring at 60° C. for 22 hr, the mixture was cooled at rt and filtered. The filtrate was concentrated and purified by silica gel chromatography (diethyl ether/pentane, 0-50%) to give product 1.47 g (29.1% yield). LCMS (m/z): 286.2 [M+H+H₂O]⁺. ¹H NMR (400 MHz, CDCl₃): 2.62-2.73 (m, 2H) 2.42-2.53 (m, 2H) 2.17 (s, 3H) 0.13 (s, 9H).

Step 2: Synthesis of 2-Methyl-6-(trimethylsilyl)hex-5-yn-2-ol [1.14b]

Methylmagnesium bromide (1.4 M in 1:3 THF/toluene, 9.36 mL, 13.1 mmol) was added dropwise to a solution of 1.14a (1.47 g, 8.73 mmol) in THF (40 mL) at 0° C. and the resulting solution was stirred at 0° C. for 1 hr. The reaction was quenched with saturated aqueous NH₄Cl and extracted with EtOAc. The combined organics were washed with brine, dried over Na₂SO₄, and concentrated to give product 1.61 g (100% yield). The crude material was continued to the next step with no further purification. LCMS (m/z): 185.2 [M+H]⁺.

Step 3: Synthesis of 2-Methylhex-5-yn-2-ol [1.14c]

A solution of 1.14b (1.61 g, 8.73 mmol) in methanol (50 mL) was treated with potassium carbonate (3.62 g, 26.2 mmol). The reaction was stirred for 1 hr at ambient temperature. The reaction was diluted with DCM (100 mL), filtered, and concentrated. The crude material was purified by flash chromatography over silica gel column chromatography, heptane/EtOAc 0-60%, to provide product (0.64 g, 53% yield). LCMS (m/z): 113.1 [M+H]⁺. ¹H NMR (400 MHz, CDCl₃) δ ppm 2.31 (td, J=7.75, 2.69 Hz, 1H) 1.97 (t, J=2.67 Hz, 1H) 1.70-1.79 (m, 2H) 1.24 (s, 6H).

Step 4: Synthesis of 2-Methyl-8-(trimethylsilyl)octa-5,7-diyn-2-ol [1.14d]

To a solution of 1.14c (0.502 g, 4.48 mmol) in piperidine (3.8 mL) at 0° C. was added (bromoethynyl)trimethylsilane (0.872 g, 4.92 mmol) and CuI (0.085 g, 0.448 mmol). The solution was stirred at ambient temperature for 2.5 hours. The reaction was quenched by adding saturated aqueous NH₄Cl solution and then extracted with EtOAc. The combined organic layers were washed sequentially with water and brine, dried over sodium sulfate, and concentrated. The crude material was purified by silica gel column chromatography (EtOAc/heptane 0 to 50%) to give product 395 mg (42.4% yield). LCMS (m/z): 209.2 [M+H]⁺.

Steps 5: Synthesis of (R)—N-hydroxy-4-(5-(5-hydroxy-5-methylhex-1-yn-1-yl)isoxazol-3-yl)-2-methyl-2-(methylsulfonyl)butanamide [1.14]

1.14

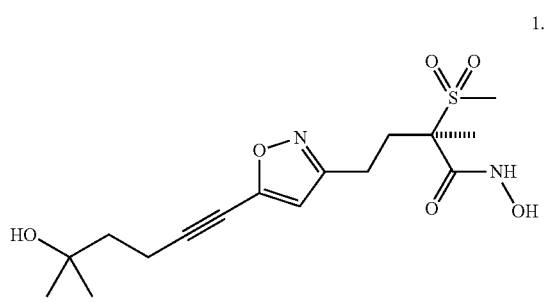

Compound 1.14 was synthesized from 1.14d following the process of Example 1.1 method B. ¹H NMR (400 MHz, CD₃OD) δ ppm 6.45 (s, 1H) 3.06 (s, 3H) 2.73-2.88 (m, 1H) 2.52-2.72 (m, 4H) 2.09-2.23 (m, 1H) 1.74-1.85 (m, 2H) 1.62 (s, 3H) 1.23 (s, 6H). LCMS (m/z): 373.3 [M+H]⁺.

I.15. Synthesis of (R)—N-hydroxy-4-(5-((3-(methoxymethyl)cyclobutyl)ethynyl)isoxazol-3-yl)-2-methyl-2-(methylsulfonyl)butanamide [1.15]

1.15

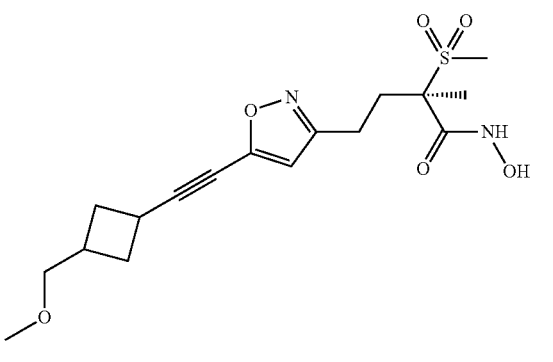

Step 1: Synthesis of Methyl 3-oxocyclobutanecarboxylate [1.15a]

To a solution of oxalyl chloride (5.25 mL, 60.0 mmol) in DCM (200 ml) at −78° C. was added DMSO (7.10 mL, 100 mmol). After 30 minutes, a solution of methyl 3-hydroxycyclobutanecarboxylate (6.51 g, 50 mmol) in methylene chloride (50 mL) was added. The mixture was stirred for 30 minutes at −78° C. and TEA (27.9 mL, 200 mmol) was then added. The mixture was allowed to warm to room temperature over 2 hours. To the reaction mixture was then added water and the layers separated. The organic phase was washed with water, dried over Na₂SO₄ and concentrated to give product (quantitative yield). ¹H NMR (400 MHz, CDCl₃): 3.14-3.32 (m, 3H) 3.32-3.46 (m, 2H) 3.73 (s, 3H)

Step 2: Synthesis of Methyl 3-(methoxymethylene)cyclobutanecarboxylate [1.15b]

A mixture of methoxymethyl)triphenyl-phosphine bromide (16.02 g, 46.8 mmol) and THF (100 mL) was placed in an ice/water bath and potassium tert-butoxide (5.25 g, 46.8 mmol) was added. The mixture was then stirred for 15 mins at 0° C. and 90 mins at rt. The mixture was cooled to 0° C. and methyl 3-oxocyclobutanecarboxylate (3 g, 23.41 mmol) was added as a solution in THF (5 mL). The resultant mixture was stirred at rt for 3 hours, then for another three hours at 70° C. The mixture was diluted with EtOAc and washed with water. The organic layer was separated and dried over Na₂SO₄, and concentrated. The crude product was purified by silica gel column chromatography, (EtOAc/heptane, 0 to 80%) to give product 1.2 g (32.8% yield). ¹H NMR (400 MHz, CDCl₃): 2.76-2.91 (m, 2H) 2.91-3.01 (m, 2H) 3.07-3.24 (m, 1H) 3.47-3.58 (m, 3H) 3.63-3.74 (m, 4H) 5.80 (quin, J=2.29 Hz, 1H)

Step 3: Synthesis of Methyl 3-formylcyclobutanecarboxylate [1.15c]

To a solution of the methyl 3-(methoxymethylene)cyclobutanecarboxylate (750 mg, 4.80 mmol) in DCM (30 mL) was added TFA (0.740 mL, 9.60 mmol) and water (2.2 mL). The resulted mixture was stirred at rt for 3 hours. The phases were separated and the aqueous layer was extracted with DCM. The organic layers were combined and concentrated. The crude product was purified by silica gel column chromatography (EtOAc/heptane 5 to 50%) to give product 640 mg (94% yield). $^1$H NMR (400 MHz, CDCl$_3$): 2.28-2.66 (m, 4H) 2.95-3.38 (m, 2H) 3.57-3.81 (m, 3H) 9.49-10.11 (m, 1H)

Step 4: Synthesis of Methyl 3-ethynylcyclobutanecarboxylate [1.15d]

To a solution of methyl 3-formylcyclobutanecarboxylate (640 mg, 4.50 mmol) in MeOH (14 mL) at 0° C. was added dimethyl (1-diazo-2-oxopropyl)phosphonate (1.107 mL, 7.20 mmol) and potassium carbonate (1244 mg, 9.00 mmol). The mixture was stirred at 0° C. for 1 h and then at rt for 3 hours. The mixture was diluted with EtOAc, washed with water and brine, dried over Na$_2$SO$_4$ and concentrated. The crude material was purified by silica gel column chromatography (EtOAc/heptane) to provide product 350 mg (56.3% yield). $^1$H NMR (400 MHz, CDCl$_3$): 2.07-2.26 (m, 1H) 2.30-2.67 (m, 4H) 2.82-3.06 (m, 1H) 3.06-3.35 (m, 1H) 3.63-3.71 (m, 3H)

Step 5: Synthesis of (3-ethynylcyclobutyl)methanol [1.15e]

To a solution of methyl 3-ethynylcyclobutanecarboxylate (377 mg, 2.73 mmol) in THF (20 mL) at 0° C. was added LiAlH$_4$ (2.73 mL, 2.73 mmol) and the mixture was stirred at 0° C. for 2 hours. The reaction was then quenched by adding water (0.45 mL) and NaOH solution (0.115 mL, 5.0 M in water, 0.573 mmol). After stirring for 5 min, the mixture was treated with Na$_2$SO$_4$, then filtered through Celite. The filtrate was concentrated to provide product (290 mg, 96% yield). The crude material was continued to the next step with no further purification.

Step 6: Synthesis of 1-ethynyl-3-(methoxymethyl)cyclobutane [1.15f]

A solution of (3-ethynylcyclobutyl)methanol (200 mg, 1.816 mmol) and MeI (0.227 mL, 3.63 mmol) in THF (4 mL) was added dropwise to a suspension of NaH (116 mg, 2.91 mmol) in THF (5 mL) at 0° C. After stirring at rt for 3 hours, the reaction was quenched by adding water (0.1 mL). The mixture was then dried over Na$_2$SO$_4$ and concentrated. The crude material was continued to the next step with no further purification. $^1$H NMR (400 MHz, CDCl$_3$): 1.87-1.96 (m, 1H) 2.01-2.30 (m, 2H) 2.33-2.54 (m, 2H) 2.82-3.11 (m, 1H) 3.24-3.44 (m, 5H)

Step 7: Synthesis of (3-(methoxymethyl)cyclobutyl) buta-1,3-diyn-1-yl)trimethylsilane [1.15g]

To a solution of 1-ethynyl-3-(methoxymethyl)cyclobutane (226 mg, 1.8 mmol) in THF (0.3 mL) at 0° C. was added CuI (34.7 mg, 0.18 mmol), piperidine (2 mL) and (iodoethynyl)trimethylsilane (0.307 mL, 2.0 mmol). The resulted mixture was stirred at 0° C. for 30 min and then at rt for 3 hours. To the mixture was then added sat. aq. NH$_4$Cl solution and TBME. The organic phase was washed with water and brine, dried over Na$_2$SO$_4$ and concentrated. The crude material was purified by silica gel column chromatography (EtOAc/Heptane, 0 to 10%) to give product 215 mg (53.6% yield). $^1$H NMR (400 MHz, CDCl$_3$): 0.18 (s, 9H) 1.91 (d, J=9.39 Hz, 2H) 2.01-2.30 (m, 2H) 2.30-2.54 (m, 2H) 3.31 (br. s., 5H)

Step 8: Synthesis of 1-(buta-1,3-diyn-1-yl)-3-(methoxymethyl)cyclobutane [1.15h]

To a solution of ((3-(methoxymethyl)cyclobutyl)buta-1,3-diyn-1-yl)trimethylsilane (215 mg, 0.976 mmol) in THF/MeOH (4.5 mL, 2/1) added NaOH (5.0 M in water, 0.585 mL, 2.93 mmol) and the resulted mixture was stirred at rt for 2 hours. The mixture was diluted with DCM, dried over Na$_2$SO$_4$ and concentrated to give product 145 mg (100% yield). The crude material was used in the next step with no further purification.

Step 9: Synthesis of (R)-benzyl 4-(5-((3-(methoxymethyl)cyclobutyl)ethynyl)isoxazol-3-yl)-2-methyl-2-(methylsulfonyl)butanoate [1.15i]

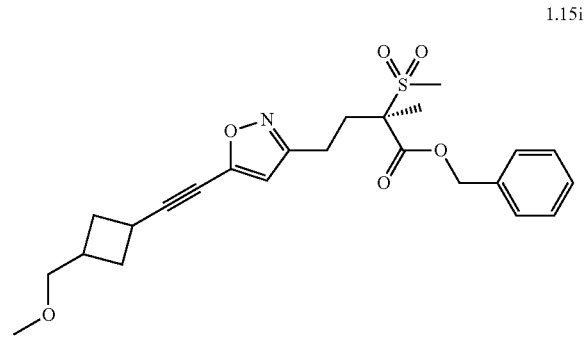 [SMILES: COCC1CC(C#Cc2cc(CC[C@](C)(C(=O)OCc3ccccc3)S(C)(=O)=O)no2)C1]

1.15i

To a solution of 1-(buta-1,3-diyn-1-yl)-3-(methoxymethyl)cyclobutan (142 mg, 0.957 mmol) and (R,E)-benzyl 5-(hydroxyimino)-2-methyl-2-(methylsulfonyl)pentanoate (200 mg, 0.638 mmol) in DCM (5 mL) was added NaClO$_2$ (0.5 M in water, 2.57 mL, 1.276 mmol) and the mixture was stirred at rt for 3 hours. The mixture was then diluted with DCM, washed with water, dried over Na$_2$SO$_4$ and concentrated. The crude material was purified by silica gel column chromatography (EtOAc/heptane, 10 to 80%) to give product 81 mg (27.6 yield). LC-MS (m/z): 460.3 [M+H]$^+$.

Step 10: Synthesis of (R)—N-hydroxy-4-(5-((3-(methoxymethyl)cyclobutyl)ethynyl)isoxazol-3-yl)-2-methyl-2-(methylsulfonyl)butanamide [1.15] [1.15a j]

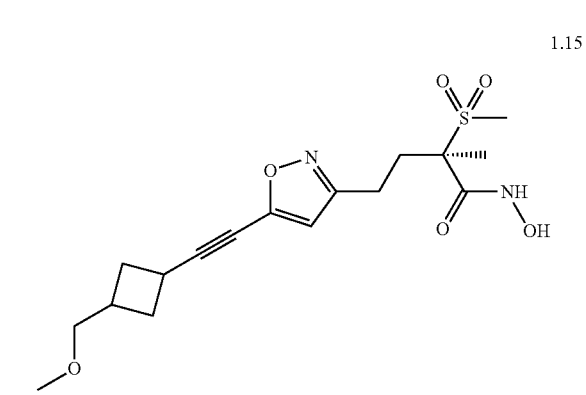 [SMILES: COCC1CC(C#Cc2cc(CC[C@](C)(C(=O)NO)S(C)(=O)=O)no2)C1]

1.15

To a solution of (R)-benzyl 4-(5-((3-(methoxymethyl)cyclobutyl)ethynyl)isoxazol-3-yl)-2-methyl-2-(methylsulfonyl)butanoate (80 mg, 0.174 mmol) in THF/MeOH (2.0 mL, 1/1) was added NH$_2$OH (50% in water, 0.460 mL) and NaOH (27.9 mg, 0.696 mmol). The resulted solution was stirred at 25° C. for 1 hour and then diluted with DMSO (3.0 mL). The mixture was placed in an ice water bath and neutralized with 5.0 N HCl aq. solution. The solvent was then removed the remaining material was purified on reverse phase HPLC to provide product 1.15a (5.0 mg, 7.10% yield) and 1.15b (2 mg, 2.84% yield).

1.15a: $^1$H NMR (400 MHz, CDCl$_3$): 1.53-1.64 (m, 3H) 1.98-2.05 (m, 1H) 2.09-2.24 (m, 1H) 2.38-2.49 (m, 3H) 2.49-2.66 (m, 5H) 2.69-2.85 (m, 3H) 2.95-3.03 (m, 3H) 3.29 (s, 3H) 3.34 (d, J=5.92 Hz, 2H) 6.35-6.49 (m, 1H). LCMS (m/z): 385.2 [M+H]$^+$.

1.15b: $^1$H NMR (400 MHz, CDCl$_3$): 1.59 (d, J=6.50 Hz, 3H) 2.08-2.36 (m, 4H) 2.60-2.85 (m, 6H) 2.92-3.02 (m, 4H) 3.27-3.35 (m, 3H), 3.40 (d, J=6.70 Hz, 2H) 6.28-6.51 (m, 1H). LCMS (m/z): 385.2 [M+H]$^+$.

I.16. Synthesis of (R)—N-hydroxy-4-(5-((3-(2-hydroxypropan-2-yl)cyclobutyl)ethynyl)isoxazol-3-yl)-2-methyl-2-(methylsulfonyl)butanamide [1.16]

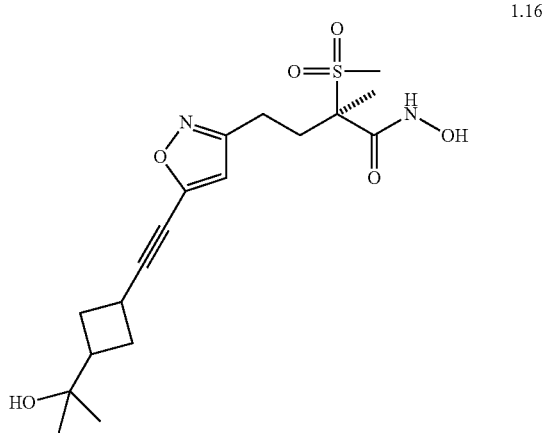 [SMILES: CC(C)(O)C1CC(C#Cc2cc(CC[C@](C)(C(=O)NO)S(C)(=O)=O)no2)C1]

1.16

Step 1. Synthesis of 2-(3-(hydroxymethyl)cyclobutyl)propan-2-ol [1.16a]

To a solution of methyl 3-(hydroxymethyl)cyclobutane-1-carboxylate (1.5 g, 10.4 mmol) at 0° C. in THF (50 mL) was added methyl magnesium bromide (27.7 mL, 1.5 M solution, 41.6 mmol) and the resulted mixture was stirred at rt for 1 h. The reaction mixture was placed in an ice water bath and quenched by adding sat. aq. NH$_4$Cl solution and EtOAc. The phases were separated and the aqueous layer was extracted EtOAc. The organic layers were combined, dried over Na$_2$SO$_4$ and concentrated. The residue was purified by silica gel column chromatography, EtOAc/heptane, 20% to 100%, to give product 1.16 g (77% yield). $^1$H NMR (400 MHz, CDCl$_3$): 3.69 (d, J=7.3 Hz, 1H, 1 isomer), 3.56 (d, J=5.8 Hz, 1H, 1 isomer), 2.45-2.17 (m, 2H), 2.12-1.92 (m, 2H), 1.77-1.65 (m, 2H), 1.13 (s, 3H), 1.10 (s, 3H).

Step 2. Synthesis of 3-(2-hydroxypropan-2-yl)cyclobutane-1-carbaldehyde [1.16b]

To a solution of oxalyl chloride (0.84 mL, 9.6 mmol) in DCM (30 mL) at −78° C. was added DMSO (1.36 mL, 19.1 mmol). After stirring for 10 mins, a solution of 1.16a (1.15 g, 7.97 mmol) in DCM (10 mL) was added and the resulting solution was stirred at −78° C. for 20 mins. Et$_3$N (4.45 mL, 31.9 mmol) was then added and the mixture was stirred at −78° C. for 10 min then slowly warmed to 0° C. To the mixture was then added sat. aq. NH$_4$Cl solution. the phase were separated and the aqueous layer was extracted with DCM. The combined organic layers were washed with brine, dried over MgSO$_4$ and concentrated. The residue was purified by silica gel column chromatography, EtOAc/heptane 0 to 50% to give product 525 mg (46% yield) as mixtures of cis/trans isomers. $^1$H NMR (400 MHz, Chloroform-d) 9.84 (d, J=1.7 Hz, 1H, 1 isomer), 9.66 (s, 1H, 1 isomer), 3.04-2.87 (m, 1H), 2.42-2.31 (m, 1H), 2.31-1.98 (m, 4H), 1.12 (d, J=7.5 Hz, 6H).

Step 3. Synthesis of 2-(3-ethynylcyclobutyl)propan-2-ol [1.16c]

To a solution of 1.16b (168 mg, 1.18 mmol) in MeOH (8 mL) at 0° C. was added Ohira Bestmann reagent (340 mg, 1.77 mmol) and potassium carbonate (327 mg, 2.36 mmol) sequentially. The reaction mixture was then stirred at rt for 2 hours. To the reaction mixture was then added water and Et$_2$O. The phases were separated and the aqueous layer was extracted twice with Et$_2$O. The organic layers were washed with brine, dried over Na$_2$SO$_4$, filtered and concentrated. The residue was purified by silica gel column chromatography, EtOAc/heptane 0 to 20% to give product 138 mg (85% yield). $^1$H NMR (400 MHz, CDCl$_3$): 2.93-2.85 (m, 0.5H), 2.83-2.73 (m, 0.5H), 2.67-2.53 (m, 0.5H), 2.33-2.20 (m, 2.5H), 2.16 (d, J=2.4 Hz, 0.5H), 2.13 (d, J=2.3 Hz, 0.5H), 2.08-2.00 (m, 2H), 1.12 (s, 3H), 1.10 (s, 3H).

Step 4. Synthesis of (R)—N-hydroxy-4-(5-((3-(2-hydroxypropan-2-yl)cyclobutyl)ethynyl)isoxazol-3-yl)-2-methyl-2-(methylsulfonyl)butanamide [1.16]

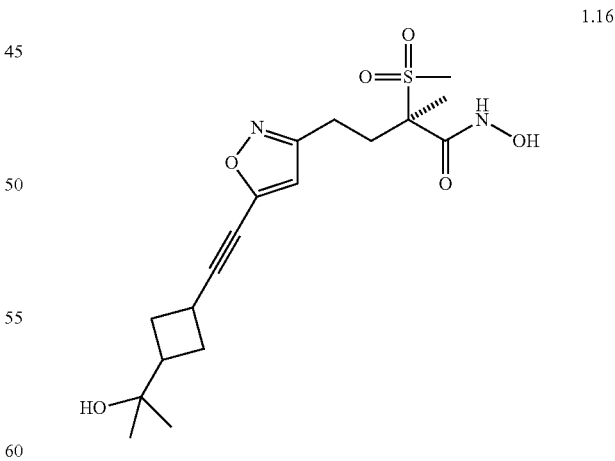

1.16

Compound 1.16 was synthesized from 1.16c by the process of Example 1.1 method B. $^1$H NMR (400 MHz, DMSO-d$_6$) δ 10.95 (s, 1H), 6.74 (s, 1H), 3.11-3.00 (m, 1H), 3.05 (s, 3H), 2.77-2.67 (m, 1H), 2.51-2.38 (m, 2H), 2.24-1.95 (m, 6H), 1.50 (s, 3H), 0.96 (s, 6H). LCMS (m/z): 399.2 [M+H]$^+$.

II.1 Synthesis of N-hydroxy-4-(5-((4-(hydroxymethyl)phenyl)ethynyl)isoxazol-3-yl)-2-methyl-2-(methylsulfonyl)butanamide [2.1]

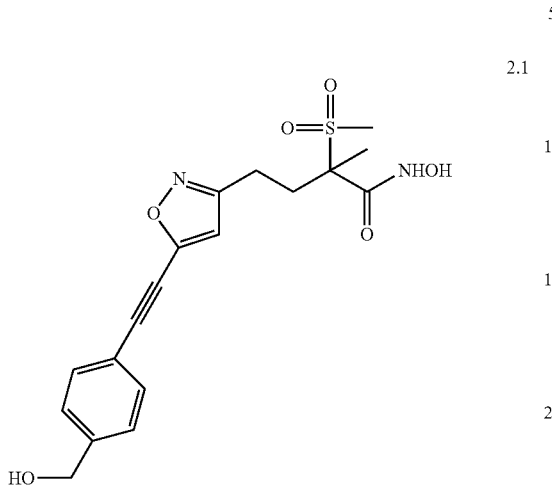

Step 1. Synthesis of buta-1,3-diyn-1-yltrimethylsilane [2.1a]

To an ice bath-cooled solution of 1,4-bis(trimethylsilyl)buta-1,3-diyne (12.5 g, 64.3 mmol) in diethyl ether (400 mL) under an inert atmosphere was cannulated methyllithium-lithium bromide complex (1.5 M in ether, 100 mL, 150 mmol). The solution was stirred for 3.5 hours at ambient temperature. The solution was cooled in an ice water bath and quenched by the dropwise addition of methanol (6.06 mL, 150 mmol). The mixture was washed sequentially with saturated aqueous NH₄Cl solution and brine, dried over magnesium sulfate, filtered, and partially concentrated to give product 2.1a (26 g of approximately 23% by weight solution in ether.) $^1$H NMR (400 MHz, CDCl₃): 2.10 (s, 1H), 0.20 (s, 9H).

Step 2. Synthesis of Ethyl 4-(5-ethynylisoxazol-3-yl)-2-methyl-2-(methylsulfonyl)butanoate [2.1b]

To a solution of 1.1b (4.3 g, 15 mmol) in MeOH (4 mL) and DCM (12 mL) was added the crude ether solution of 2.1a (12 mL, 17 mmol). Triethylamine (4.2 ml, 30 mmol) was then added dropwise over 30 mins, and the mixture was stirred at ambient temperature for 2 hours. The reaction mixture was diluted with water (30 mL) and extracted with diethyl ether. The combined extracts were washed with brine, dried over Na₂SO₄ and concentrated. The crude material was allowed to stand at ambient temperature overnight, allowing the TMS group to be cleaved. The residue was then purified by silica gel column chromatography, heptane/EtOAc 20-70%, to give product 2.1b (1.8 g, 41%). $^1$H NMR (400 MHz, CDCl₃): 6.39 (s, 1H) 4.28 (q, J=7.16 Hz, 2H) 3.61 (s, 1H) 3.06 (s, 3H) 2.81-2.94 (m, 1H) 2.66-2.78 (m, 1H) 2.60 (ddd, J=13.52, 11.30, 5.26 Hz, 1H) 2.33 (ddd, J=13.52, 11.40, 5.16 Hz, 1H) 1.69 (s, 3H) 1.33 (t, J=7.14 Hz, 3H). LCMS (m/z): 300.0 [M+H]⁺.

Step 3. Synthesis of Ethyl 4-(5-(bromoethynyl)isoxazol-3-yl)-2-methyl-2-(methylsulfonyl)butanoate [2.1c]

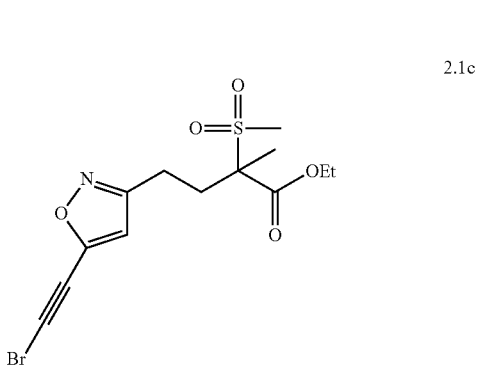 [SMILES: CCOC(=O)C(C)(CCc1cc(C#CBr)on1)S(C)(=O)=O]

Bromine (0.114 mL, 2.21 mmol) was added dropwise to 3.0 M aqueous sodium hydroxide (1.67 mL, 5.01 mmol) that was cooled in an ice bath. A pre-cooled solution of 2.1b (600 mg, 2.00 mmol) in THF (0.8 mL) was added dropwise over 5 mins. The biphasic mixture was stirred vigorously for 30 mins at 0° C. The reaction was quenched by the addition of saturated aqueous ammonium chloride and extracted with diethyl ether. The combined extracts were washed with brine, dried over sodium sulfate, filtered, and concentrated. The crude material was purified by silica gel column chromatography, EtOAc/heptane 10-50%, to afford product 575 mg (76% yield). $^1$H NMR (400 MHz, CDCl₃): 6.33 (s, 1H) 4.28 (q, J=7.14 Hz, 2H) 3.06 (s, 3H) 2.79-2.94 (m, 1H) 2.65-2.78 (m, 1H) 2.59 (ddd, J=13.53, 11.24, 5.26 Hz, 1H) 2.33 (ddd, J=13.55, 11.37, 5.16 Hz, 1H) 1.69 (s, 3H) 1.33 (t, J=7.12 Hz, 3H). LCMS (m/z): 377.9/379.9 [M+H]⁺.

Step 4. Synthesis of Ethyl 4-(5-((4-(hydroxymethyl)phenyl)ethynyl)isoxazol-3-yl)-2-methyl-2-(methylsulfonyl)butanoate [2.1d]

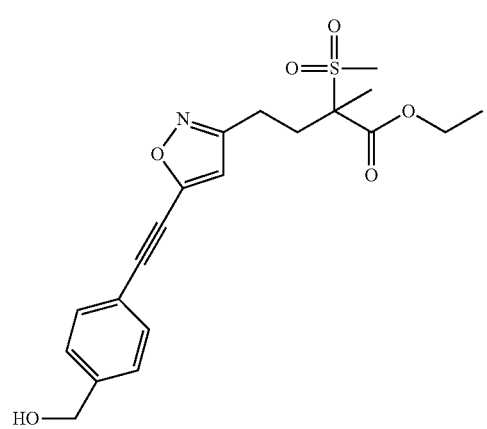

To a degassed mixture of 2.1c (120 mg, 0.317 mmol) and (4-(hydroxymethyl)phenyl)boronic acid (72.3 mg, 0.476 mmol) in DMF (1.5 mL) and 2.0M aqueous sodium carbonate (0.555 mL, 1.11 mmol) was added PdCl₂(dppf)·CH₂Cl₂ adduct (25.9 mg, 0.032 mmol). The reaction mixture was heated at 110° C. in the microwave for 15 mins. The reaction mixture was diluted with water and extracted with EtOAc. The combined extracts were dried over sodium sulfate, filtered, and concentrated. The crude material was purified by silica gel column chromatography, MeOH/DCM 0-8%, to give 2.1d (40 mg, 31 yield). LCMS (m/z): 406.1 [M+H]$^+$.

Step 5. Synthesis of N-hydroxy-4-(5-((4-(hydroxymethyl)phenyl)ethynyl)isoxazol-3-yl)-2-methyl-2-(methylsulfonyl)butanamide [2.1]

Powdered sodium hydroxide (19.7 mg, 0.493 mmol) was added to a mixture of 2.1d (40 mg, 0.099 mmol) and hydroxylamine (0.151 mL, 2.47 mmol) in 1:1 THF:MeOH (1 mL). The reaction was stirred at ambient temperature for 15 min. Volatiles were removed under reduced pressure. The crude material was purified by reverse-phase HPLC to afford give 2.1 (9 mg, 20% yield). $^1$H NMR (400 MHz, CD$_3$OD): 7.54-7.60 (m, 2H), 7.41-7.46 (m, 2H), 6.64-6.67 (m, 1H), 4.63-4.67 (m, 2H), 3.08 (s, 3H), 2.81-2.92 (m, 1H), 2.61-2.76 (m, 2H), 2.14-2.28 (m, 1H), 1.65 (s, 3H). LCMS (m/z): 393.3 [M+H]$^+$.

II.2 Synthesis of N-hydroxy-4-(5-((4-(2-hydroxyethyl)phenyl)ethynyl)isoxazol-3-yl)-2-methyl-2-(methylsulfonyl)butanamide [2.2]

Compound 2.2 was prepared following the process of Example 2.1. $^1$H NMR (400 MHz, CD$_3$OD): 7.48-7.53 (m, 2H) 7.30-7.35 (m, 2H) 6.63-6.65 (m, 1H) 3.75-3.83 (m, 2H) 3.05-3.09 (s, 3H) 2.78-2.93 (m, 3H) 2.59-2.76 (m, 2H) 2.13-2.27 (m, 1H) 1.62-1.68 (s, 3H). LCMS (m/z): 407.3 [M+H]$^+$.

II.3 Synthesis of N-hydroxy-4-(5-((4-(2-hydroxy-1-methoxyethyl)phenyl)ethynyl) isoxazol-3-yl)-2-methyl-2-(methylsulfonyl)butanamide [2.3]

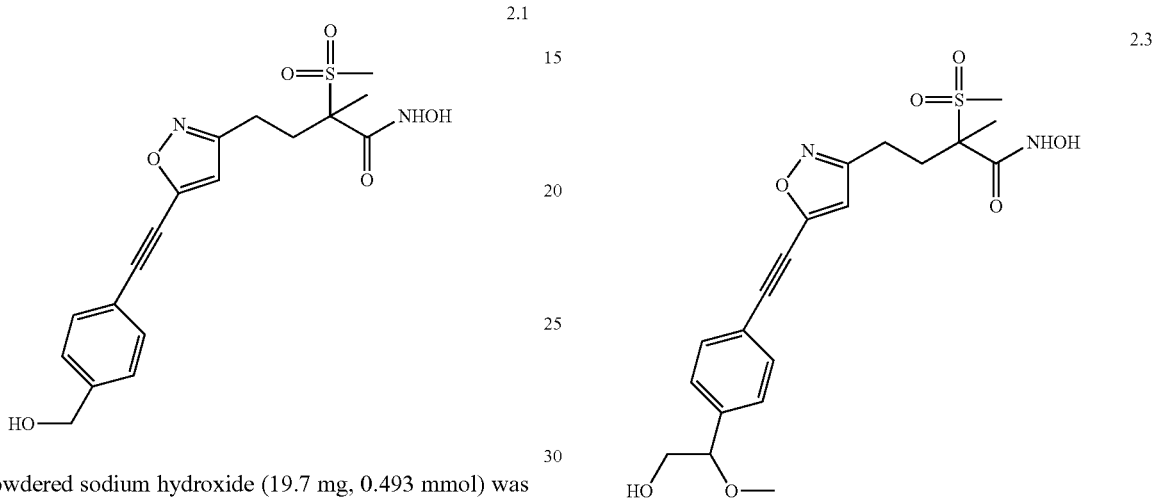

Compound 2.3 was prepared following the process of Example 2.1. $^1$H NMR (400 MHz, CD$_3$OD): 7.56-7.62 (m, 2H) 7.39-7.45 (m, 2H) 6.65-6.68 (m, 1H) 4.27-4.36 (m, 1H) 3.52-3.71 (m, 2H) 3.04-3.10 (s, 3H) 2.79-2.93 (m, 1H) 2.60-2.76 (m, 2H) 2.14-2.26 (m, 1H) 1.61-1.68 (s, 3H). LCMS (m/z): 437.3 [M+H]$^+$.

II.4 Synthesis of N-hydroxy-2-methyl-2-(methylsulfonyl)-4-(5-(phenylethynyl)isoxazol-3-yl)butanamide [2.4]

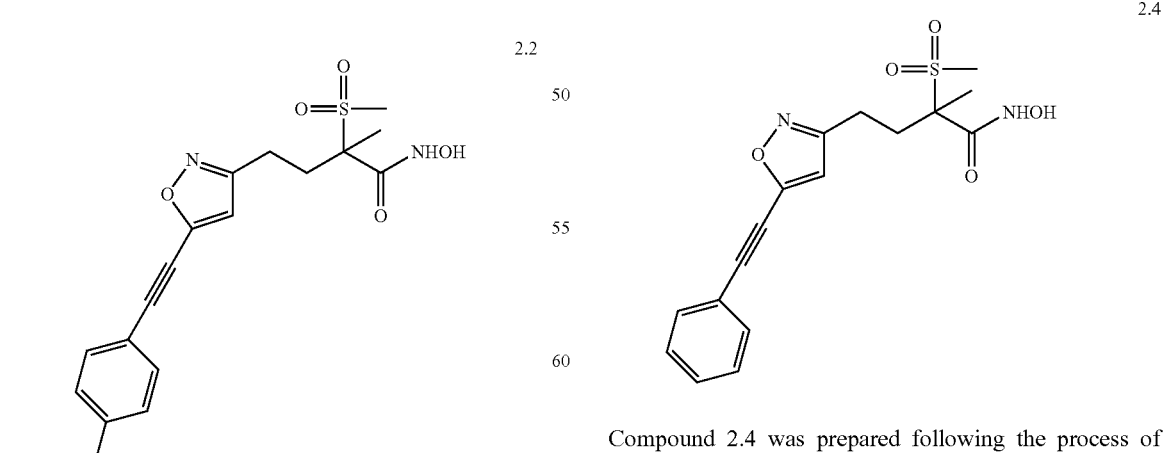

Compound 2.4 was prepared following the process of Example 2.1. 1H NMR (400 MHz, CD$_3$OD): 7.54-7.61 (m, 2H) 7.40-7.49 (m, 3H) 6.64-6.68 (m, 1H) 3.07 (s, 3H) 2.79-2.91 (m, 1H) 2.60-2.76 (m, 2H) 2.13-2.26 (m, 1H) 1.64 (s, 3H). LCMS (m/z): 363.1 [M+H]$^+$.

II.5 Synthesis of N-hydroxy-4-(5-((4-((R)-2-hydroxypropyl)phenyl)ethynyl)isoxazol-3-yl)-2-methyl-2-(methylsulfonyl)butanamide [2.5]

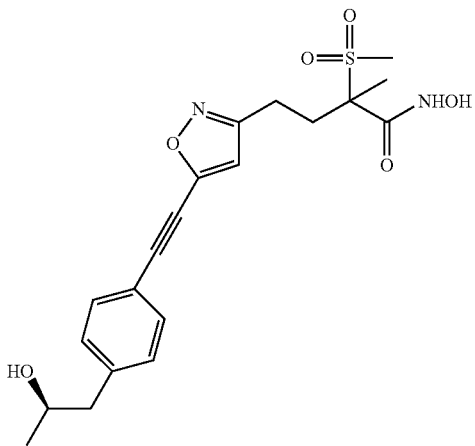

Compound 2.5 was prepared following the process of Example 2.1. $^1$H NMR (400 MHz, CD$_3$OD): 7.48-7.53 (m, 2H) 7.27-7.33 (m, 2H) 6.62-6.64 (m, 1H) 3.92-4.03 (m, 1H) 3.05-3.10 (s, 3H) 2.59-2.91 (m, 5H) 2.14-2.26 (m, 1H) 1.60-1.68 (s, 3H) 1.12-1.22 (m, 3H). LCMS (m/z): 421.0 [M+H]$^+$.

II.6 Synthesis of (R)—N-hydroxy-4-(5-((4-((S)-2-hydroxy-1-methoxyethyl)phenyl)ethynyl)-isoxazol-3-yl)-2-methyl-2-(methylsulfonyl)butanamide [2.6]

Step 1. Synthesis of benzyl (R)-4-(5-ethynylisoxazol-3-yl)-2-methyl-2-(methylsulfonyl)butanoate [2.6a]

Compound 2.6a was synthesized from 1.2f and 2.1a following the process of Example 1.1 step 2-3. LCMS (m/z): 362.0 [M+H]$^+$.

Step 2. Synthesis of (R)—N-hydroxy-4-(5-((4-((S)-2-hydroxy-1-methoxyethyl)phenyl)ethynyl)-isoxazol-3-yl)-2-methyl-2-(methylsulfonyl)butanamide [2.6]

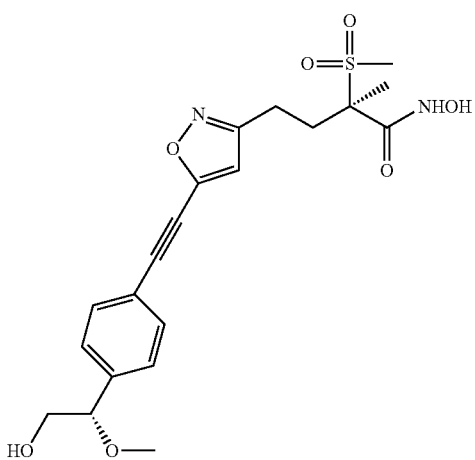

Compound 2.6 was prepared from 2.6a following the process of Example 2.1 step 3-4 and Example 1.1 step 4-6. $^1$H NMR (400 MHz, DMSO-d$_6$): 10.15 (d, J=0.88 Hz, 1H) 8.40 (d, J=1.47 Hz, 1H) 6.82 (d, J=8.22 Hz, 2H) 6.59 (d, J=8.17 Hz, 2H) 6.15 (s, 1H) 4.04 (s, 1H) 3.44 (d, J=1.71 Hz, 1H) 2.68-2.79 (m, 1H) 2.58-2.67 (m, 1H) 2.39 (s, 3H) 2.25 (s, 3H) 1.90-2.03 (m, 1H) 1.70-1.82 (m, 1H) 1.17-1.31 (m, 1H) 0.71 (s, 3H). LCMS (m/z): 437.0 [M+H]$^+$.

II.7 Synthesis of (R)-4-(5-((4-((S)-1,2-dihydroxyethyl)phenyl)ethynyl)isoxazol-3-yl)-N-hydroxy-2-methyl-2-(methylsulfonyl)butanamide [2.7]

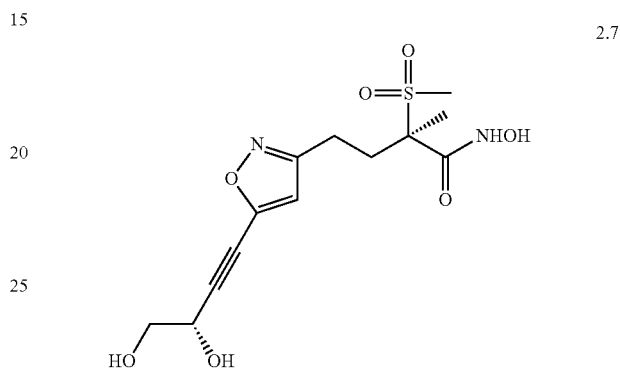

Compound 2.7 was prepared following the process of Example 2.6. $^1$H NMR (500 MHz, CD$_3$OD): 7.57 (d, J=8.20 Hz, 2H) 7.47 (d, J=8.20 Hz, 2H) 6.67 (s, 1H) 4.73 (d, J=7.25 Hz, 1H) 4.61 (s, 1H) 3.57-3.68 (m, 1H) 3.07 (s, 3H) 2.84 (m, 1H) 2.58-2.75 (m, 2H) 2.13-2.26 (m, 1H) 1.64 (s, 3H). LCMS (m/z): 423.2 [M+H]$^+$.

II.8 Synthesis of (R)-4-(5-((4-((R)-1,2-dihydroxyethyl)phenyl)ethynyl)isoxazol-3-yl)-N-hydroxy-2-methyl-2-(methylsulfonyl)butanamide [2.8]

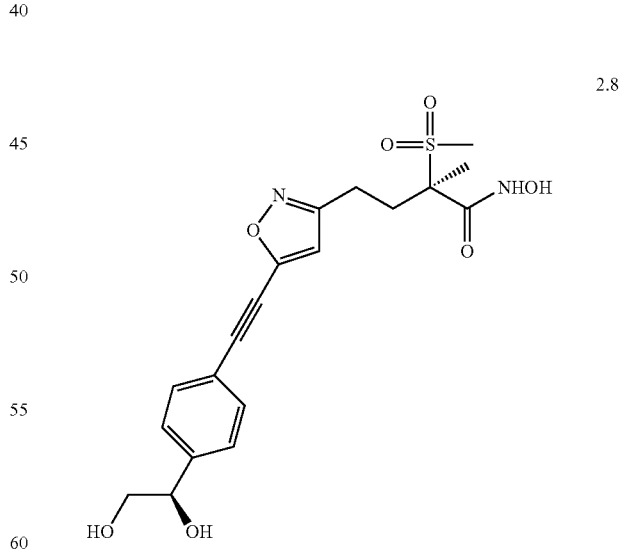

Compound 2.8 was prepared following the process of Example 2.6. $^1$H NMR 400 MHz, CD$_3$OD): 7.55-7.64 (m, 2H) 7.49 (d, J=8.17 Hz, 2H) 6.68 (s, 1H) 4.75 (dd, J=6.68, 5.06 Hz, 1H) 3.58-3.73 (m, 2H) 3.10 (s, 3H) 2.82-2.95 (m, 1H) 2.61-2.79 (m, 2H) 2.15-2.28 (m, 1H) 1.67 (s, 3H). LCMS (m/z): 423.2 [M+H]$^+$.

III.1 Synthesis of (2S,3R)-2-(((5-(cyclopropylethynyl)isoxazol-3-yl)methyl)amino)-N,3-dihydroxy-2-methyl-3-(5-methylisoxazol-3-yl)propanamide [3.1]

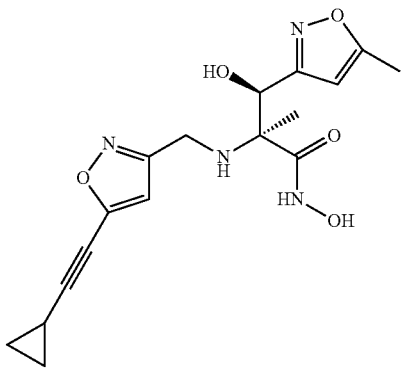

3.1

Step 1. Synthesis of ethyl 5-(tributylstannyl)isoxazole-3-carboxylate [3.1a]

Tributyl(ethynyl)stannane (4 g, 12.7 mmol, 1.0 equiv) and ethyl (E)-2-chloro-2-(hydroxyimino)acetate (1.92 g, 12.7 mmol, 1.0 equiv) were dissolved in diethyl ether (40 mL). TEA (6.41 g, 63.5 mmol, 5.0 equiv) was added dropwise and the reaction mixture was stirred at room temperature for 4 hours. The reaction was quenched with water and extracted with EtOAc. The organic layer was washed with brine, dried over sodium sulfate and concentrated. The residue was purified by silica gel column chromatography (10-15 EtOAc in Hexane) to afford product (2.5 g, 45.7% yield). $^1$H NMR (400 MHz, CDCl$_3$) δ 6.82 (s, 1H), 4.46 (q, J=7.1 Hz, 2H), 1.62 (d, J=7.0 Hz, 2H), 1.58-1.53 (m, 2H), 1.44 (t, J=7.1 Hz, 3H), 1.34 (ddd, J=26.0, 16.7, 9.4 Hz, 8H), 1.26-1.14 (m, 6H), 0.92 (t, J=7.3 Hz, 9H).

Step 2. Synthesis of ethyl 5-(cyclopropylethynyl)isoxazole-3-carboxylate [3.1 b]

(Iodoethynyl)cyclopropane (8 g, 0.041 mmol, 1.2 equiv) and 3.1 (15 g, 34.0 mmol, 1.0 equiv) were dissolved in 1,4-dioxane (80 mL). The reaction mixture was degassed for 10 minutes. PdCl$_2$(pph$_3$)$_2$ (0.48 g, 0.6 mmol, 0.02 equiv) was added and the reaction mixture was stirred at 100° C. for 2 hours. The reaction mixture was quenched with water and extracted with EtOAc. The organic layer was washed with brine, dried over sodium sulfate and concentrated. The crude residue was purified by silica gel column chromatography (10-25% EtOAc/Hexane) to afford product (4.02 g, 50% yield). LCMS (m/z): 206.1 [M+H]$^+$.

Step 3. Synthesis of (5-(cyclopropylethynyl)isoxazol-3-yl) methanol [3.1c]

Ethyl 5-(cyclopropylethynyl) isoxazole-3-carboxylate (4 g, 19.0 mmol, 1.0 equiv) was dissolved in THF (40 mL) and cooled to 0° C. Sodium borohydride (1.52 g, 39.0 mmol, 2.0 equiv) was added in portion wise. Methanol (4 mL) was then added and the reaction mixture was stirred at room temperature for 4 hours. The reaction mixture was quenched with water and extracted with EtOAc. The organic layer was washed with brine, dried over sodium sulfate and concentrated. The crude residue was purified by silica gel column chromatography (30-40% EtOAc/Hexane) to afford product (1.72 g, 65% yield). LCMS (m/z): 163.8 [M+H]$^+$. $^1$H NMR (400 MHz, DMSO-d$_6$) δ ppm 0.84-0.88 (m, 2H) 0.97-1.02 (m, 2H) 1.69 (m, 1H) 5.52 (t, J=5.95 Hz, 1H) 6.67 (s, 1H).

Step 4. Synthesis of 5-(cyclopropylethynyl) isoxazole-3-carbaldehyde [3.1d]

(5-(cyclopropylethynyl) isoxazol-3-yl) methanol (1.72 g, 10.0 mmol, 1.0 equiv) was dissolved in dichloromethane (50 mL) and cooled to 0° C. Dess-Martin periodinane (6.71 g, 15.0 mmol, 1.5 equiv) was added in portion wise and the reaction mixture was stirred at room temperature for 5 hours. The reaction mixture was quenched with saturated aqueous sodium bicarbonate solution: sodium thiosulphate solution (1:1) and extracted with EtOAc. The organic layer was washed with brine, dried over sodium sulfate and concentrated. The crude residue was purified by silica gel column chromatography (10-12% EtOAc/Hexane) to afford product (1.2 g, 68% yield). LCMS (m/z): 162.1 [M+H]$^+$. $^1$H NMR (400 MHz, DMSO-d$_6$) δ ppm 0.89-0.92 (m, 2H) 1.01-1.05 (m, 2H) 1.69-1.78 (m, 1H) 7.15 (s, 1H) 10.07 (s, 1H).

Step 5. Synthesis of (2S,3R)-methyl 2-((tert-butoxycarbonyl)amino)-3-hydroxy-2-methyl-3-(5-methylisoxazol-3-yl)propanoate [3.1e]

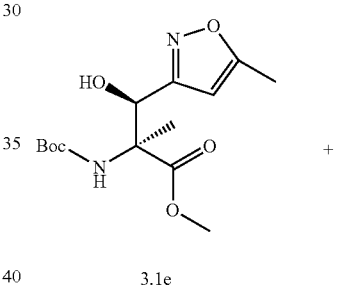

3.1e

+

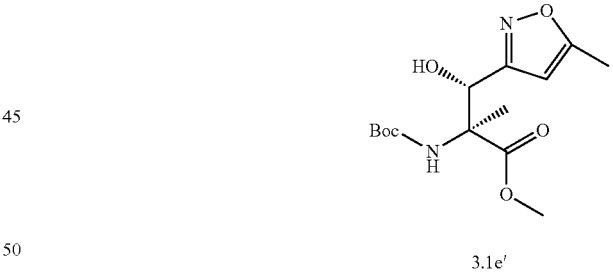

3.1e'

To a solution of diisopropylamine (16.97 mL, 119 mmol) in THF (60 mL), butyllithium (74.4 mL, 119 mmol) was slowly added. The reaction was stirred at −78° C. for 1 hour, at which time a solution of (S)-methyl 2-((tert-butoxycarbonyl)amino)propanoate (11 g, 54.1 mmol) in 40 mL THF was added. The reaction was allowed to stir for another 2 hours, at which time 5-methylisoxazole-3-carbaldehyde (7.82 g, 70.4 mmol) in 10 mL THF was added. The reaction was allowed to stir at −78° C. for another 2 hours and then warm −40° C. The reaction was quenched with saturated aqueous NH$_4$Cl solution and was then allowed to warm to room temperature. The mixture was extracted with EtOAc. The organic layer was washed with brine, dried over magnesium sulfate and concentrated. The crude material was purified by silica gel column chromatography, (EtOAc/ heptane, 0-30%) to afford (±)-3.1e (5.3 g, 31% yield) and (±)-3.1.e' (5.4 g, 17.18 mmol, 31.7% yield). The less polar fraction is the desired diastereomers (±)-3.1e.

(±)-3.1e: $^1$H NMR (400 MHz, CDCl3) 6.03-6.14 (m, 1H), 6.00 (s, 1H), 5.78-5.89 (m, 1H), 5.31 (d, J=9.5 Hz, 1H), 3.85 (s, 3H), 2.40 (d, J=0.6 Hz, 3H), 1.70 (s, 3H), 1.43 (s, 9H). LCMS (m/z): 315.3 [M+H]$^+$.

The diastereomer (±)-3.1e was separated by chiral SFC to afford two enantiomers: Isomer 1: tR 1.45 min and isomer 2: tR 2.76 min. The isomer 2 is the desired enantiomer 3.1e.

SFC separation condition:

Chiral AD column; flow rate 100 ml/min; CO$_2$/EtOH=90/10; 293 bar.

Step 6. Synthesis of (2S,3R)-methyl 2-amino-3-hydroxy-2-methyl-3-(5-methylisoxazol-3-yl)propanoate HCl salt [3.1f]

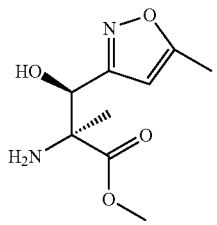

3.1f

A solution of 3.1e (2.1 g, 6.68 mmol) and HCl in MeOH (66.8 ml, 66.8 mmol) was stirred at room temperature for 24 hours. The reaction was concentrated in vacuo to afford 3.1f as a HCl salt (1.5 g, 5.74 mmol, 86% yield). $^1$H NMR (DMSO-d$_6$) 8.72 (br. s., 3H), 7.05 (d, J=5.4 Hz, 1H), 6.21 (s, 1H), 5.00 (d, J=5.0 Hz, 1H), 3.62-3.80 (m, 3H), 2.39-2.43 (m, 3H), 1.34-1.57 (m, 3H). LCMS (m/z): 216.3 [M+H]$^+$.

Step 7. Synthesis of (2S,3R)-methyl 2-(((5-(cyclopropylethynyl)isoxazol-3-yl)methyl)amino)-3-hydroxy-2-methyl-3-(5-methylisoxazol-3-yl)propanoate [3.1g]

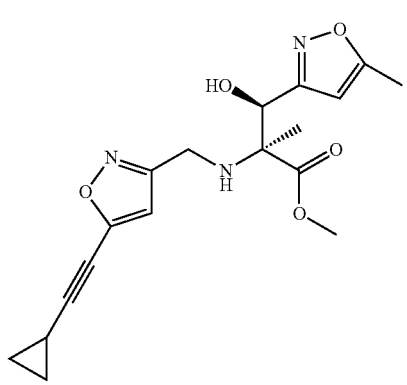

3.1g

Triethylamine (0.280 ml, 2.007 mmol) was added to a solution of 3.1d (420 mg, 2.007 mmol) and 3.1f (528 mg, 2.107 mmol) in DCE. After 10 mins, AcOH (0.230 ml, 4.01 mmol) was then added and the reaction stirred at rt for 18 hours. Sodium triacetoxyborohydride (1.2 g, 5.66 mmol) was then added and the mixture was stirred for 3 hours. The reaction was quenched by adding water and sat. aq. NaHCO$_3$ solution. The mixture was extracted with DCM. The organic layer was dried over Na$_2$SO$_4$ and concentrated. The crude material was purified by silica gel column chromatography, EtOAc/heptane, 0 to 100% to afford product 436 mg (yield 60%). LCMS (m/z): 360.4 [M+H]$^+$.

Step 8. Synthesis of (2S,3R)-2-(((5-(cyclopropylethynyl)isoxazol-3-yl)methyl)amino)-N,3-dihydroxy-2-methyl-3-(5-methylisoxazol-3-yl)propanamide [3.1]

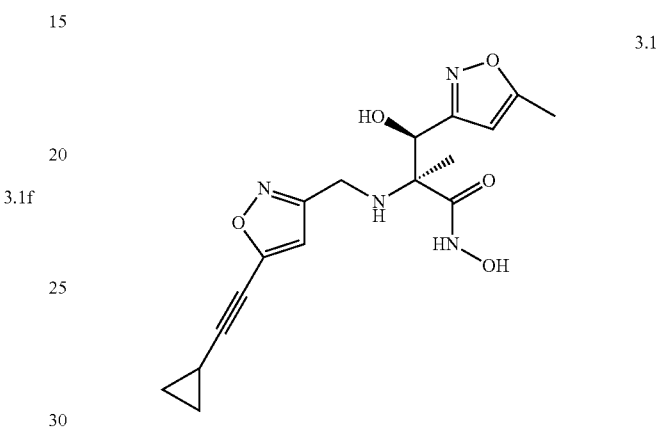

3.1

Hydroxylamine solution (50% in water, 5662 mg, 86 mmol) and sodium hydroxide (110 mg, 2.75 mmol) were added to a solution of 3.1 g (880 mg, 1.7 mmol) in MeOH and the resulting solution was stirred at rt for 3 hours. The mixture was then concentrated and the residue was purified by reverse phase HPLC (10-50% MeCN-Water, 3.75 mM Ammonium Acetate buffer) to afford product 177 mg (yield 27%). 1H NMR (400 MHz, CDCl$_3$): 0.82-1.05 (m, 4H), 1.33 (s, 3H), 1.47-1.51 (m, 1H), 2.39 (s, 3H) 3.68-4.03 (m, 2H), 5.10 (s, 1H) 6.10 (s, 1H) 6.24 (s, 1H). LCMS (m/z): 361.3 [M+H]$^+$.

III.2. Synthesis of (2S,3R)-2-(((5-(cyclobutylethynyl)isoxazol-3-yl)methyl)amino)-N,3-dihydroxy-2-methyl-3-(5-methylisoxazol-3-yl)propanamide [3.2]

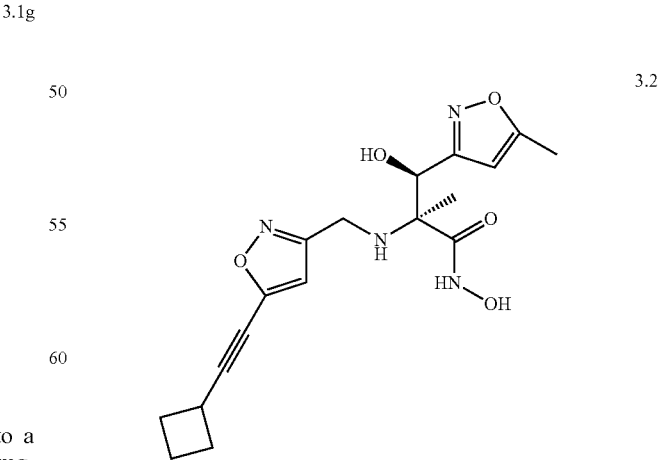

3.2

Compound 3.2 was synthesized by the process of Example 3.1. $^1$H NMR (500 MHz, CDCl$_3$): 1.41 (s, 3H), 1.86-2.08 (m, 2H), 2.16-2.43 (m, 5H), 2.46 (s, 3H), 3.28-3.32 (m, 1H), 3.83 (m, 1H), 4.09 (m, 1H), 5.06-5.31 (m, 1H), 6.03-6.19 (m, 2H) 6.28 (s, 1H). LCMS (m/z): 375.2 [M+H]$^+$.

III.3 Synthesis of (2S,3R)—N,3-dihydroxy-2-methyl-3-(5-methylisoxazol-3-yl)-2-(((5-(phenylethynyl)isoxazol-3-yl)methyl)amino)propanamide [3.3]

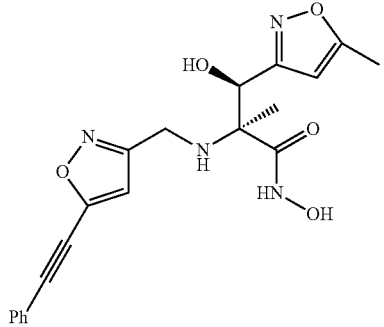

Compound 3.3 was synthesized by the process of Example 3.1. $^1$H NMR (500 MHz, DMSO-d6): 1.14 (s, 3H), 2.38 (s, 3H), 3.70-3.80 (m, 2H), 4.76-4.77 (m, 1H), 5.91-6.02 (m, 1H) 6.14 (s, 1H), 6.97 (s, 1H), 7.39-7.57 (m, 3H), 7.63-7.76 (m, 2H), 8.68-8.88 (m, 1H). LCMS (m/z): 397.3 [M+H]$^+$.

III.4. Synthesis of N,3-dihydroxy-3-(5-(hydroxymethyl)isoxazol-3-yl)-2-methyl-2-(((5-(phenylethynyl)isoxazol-3-yl)methyl)amino)propanamide] [3.4]

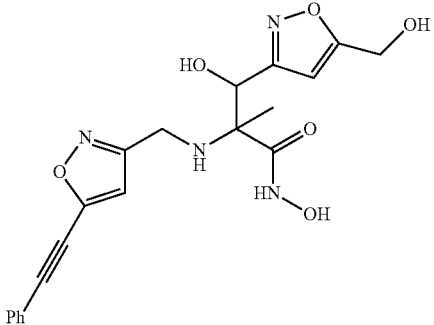

Compound 3.4 was synthesized by the process of Example 3.1. $^1$H NMR (METHANOL-d4) δ: 7.58-7.65 (m, 2H), 7.42-7.53 (m, 3H), 6.77 (s, 1H), 6.39 (s, 1H), 4.96 (s, 1H), 4.67 (s, 2H), 3.90-3.95 (m, 1H), 3.81-3.88 (m, 1H), 1.36 (s, 3H). LCMS (m/z): 413.2 [M+H]$^+$.

III.5. Synthesis of (2S,3R)—N,3-dihydroxy-2-(((5-(6-methoxyhex-1-yn-1-yl)isoxazol-3-yl)methyl)amino)-2-methyl-3-(5-methylisoxazol-3-yl)propanamide [3.5]

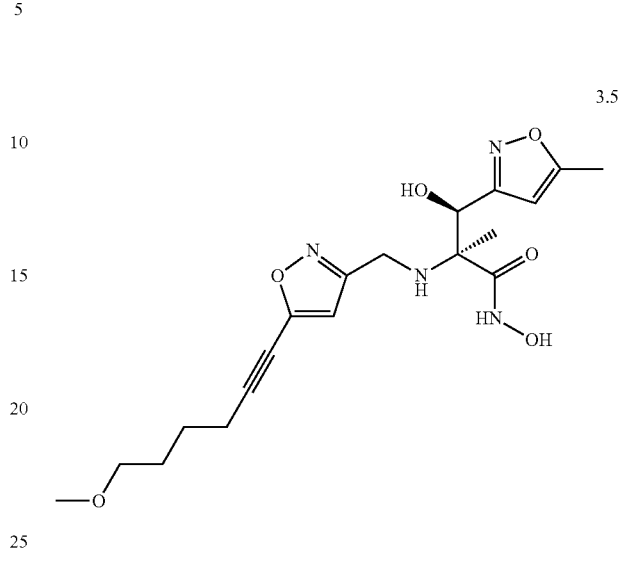

Compound 3.5 was synthesized by the process of Example 3.1. $^1$H NMR (400 MHz, DMSO) δ 10.38 (s, 1H), 8.76 (s, 1H), 6.72 (s, 1H), 6.12 (s, 1H), 5.94 (s, 1H), 4.75 (s, 1H), 3.68 (s, 2H), 3.36 (s, 2H), 3.24 (s, 3H), 2.56 (s, 2H), 2.37 (s, 3H), 1.62 (s, 4H), 1.14 (s, 3H). LCMS (m/z): 407.6 [M+H]$^+$.

III.6. Synthesis of 2-(((5-(cyclopropylethynyl) isoxazol-3-yl) methyl) amino)-3-(5-cyclopropylisoxazol-3-yl)-N, 3-dihydroxy-2-methylpropanamide [3.6]

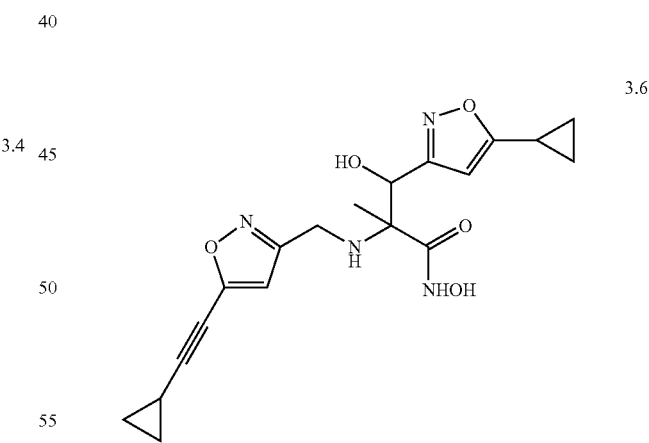

Compound 3.6 was synthesized by the process of Example 3.1. $^1$H NMR (400 MHz, DMSO) δ 6.66 (s, 1H), 6.07 (s, 1H), 5.99 (s, 1H), 4.71 (s, 1H), 3.65 (s, 2H), 2.62 (m, 1H), 2.10 (ddd, J=13.3, 8.4, 4.9 Hz, 1H), 1.69 (ddd, J=13.2, 8.3, 5.1 Hz, 1H), 1.11 (s, 3H), 1.08-0.93 (m, 4H), 0.90-0.82 (m, 4H). LCMS (m/z): 387.3 [M+H]$^+$.

IV.1. Synthesis of (R,E)-4-(5-(but-1-en-1-yl)isox-azol-3-yl)-N-hydroxy-2-methyl-2-(methylsulfonyl)butanamide [4.1]

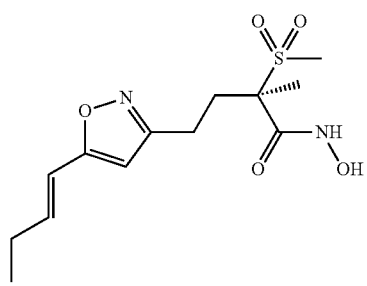

4.1

Step 1: Synthesis of (2R)-benzyl 4-(5-(2-hydroxy-butyl)isoxazol-3-yl)-2-methyl-2-(methylsulfonyl)butanoate [4.1a]

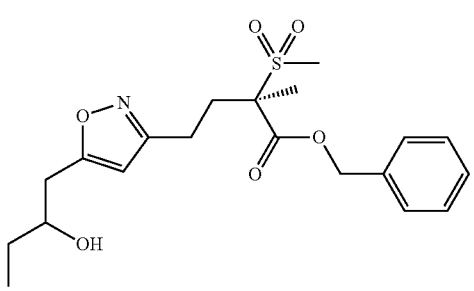

4.1a

To a solution of hex-5-yn-3-ol (125 mg, 1.276 mmol) and (R,E)-benzyl 5-(hydroxyimino)-2-methyl-2-(methylsulfonyl)pentanoate (200 mg, 0.638 mmol) in DCM (5 mL) was added NaClO$_2$ (2.66 g, 1.276 mmol) and the mixture was stirred at rt for 15 hours. The reaction mixture was then diluted with DCM and the phases were separated. The organic layer was washed with water, dried over Na$_2$SO$_4$, and concentrated. The remaining material was purified by silica gel column chromatography, EtOAc/heptane 5 to 80%, to give product 91 mg (34.8% yield). LCMS (m/z): 410.3 [M+H]$^+$.

Step 2: Synthesis of benzyl (2R)-2-methyl-2-(methylsulfonyl)-4-(5-(2-((methylsulfonyl)oxy)butyl)isoxazol-3-yl)butanoate [4.1 b]

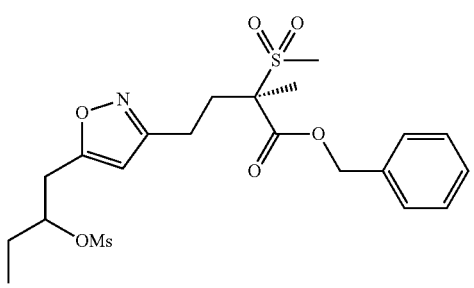

4.1b

To a solution of (2R)-benzyl 4-(5-(2-hydroxybutyl)isoxazol-3-yl)-2-methyl-2-(methylsulfonyl)butanoate (92 mg, 0.225 mmol) in dichloromethane (2 mL) at 0° C. was added methanesulfonyl chloride (0.021 mL, 0.270 mmol) and TEA (0.063 mL, 0.449 mmol). The reaction was stirred at rt stirred for 3 hour before quenched by adding water. The phases were separated and the organic layer was extracted with DCM. The organic layer was washed with brine, dried over Na$_2$SO$_4$ and concentrated to give product 108 mg (99% yield). The crude material was continued to the next step with no further purification. LCMS (m/z): 488.3 [M+H]$^+$.

Step 3: Synthesis of (R,E)-4-(5-(but-1-en-1-yl)isox-azol-3-yl)-N-hydroxy-2-methyl-2-(methylsulfonyl)butanamide [4.1]

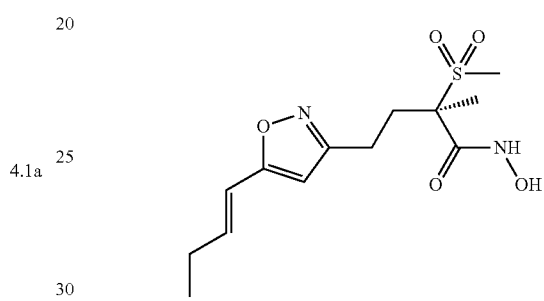

4.1

To a solution of (2R)-benzyl 2-methyl-2-(methylsulfonyl)-4-(5-(2-((methylsulfonyl)oxy)butyl)isoxazol-3-yl)butanoate (108 mg, 0.221 mmol) in MeOH (1 mL) and THF (1 mL) at rt was added NH$_2$OH (0.585 mL, 50% in water, 8.86 mmol) and NaOH (89 mg, 2.215 mmol). After stirring at rt for 1 h, the mixture was then diluted with DMSO (1.5 mL) and the volatile solvent was removed under vacuum. The mixture was neutralized with 3N HCl and then filtered. The crude material was purified by reverse phase prep HPLC to give product 10 mg (13.98% yield). $^1$H NMR (400 MHz, DMSO-d$_6$): 1.02 (t, J=7.41 Hz, 3H) 1.41-1.54 (m, 3H) 1.97 (td, J=12.36, 4.87 Hz, 1H) 2.13-2.28 (m, 2H) 2.32-2.45 (m, 2H) 2.58-2.74 (m, 1H) 2.98-3.10 (m, 3H) 6.33-6.43 (m, 2H) 6.45-6.63 (m, 1H) 10.94 (s, 1H). LCMS (m/z): 317.2 [M+H]$^+$.

IV.2. Synthesis of (R,E)-4-(5-(2-cyclopropylvinyl)isoxazol-3-yl)-N-hydroxy-2-methyl-2-(methylsulfonyl)butanamide [4.2]

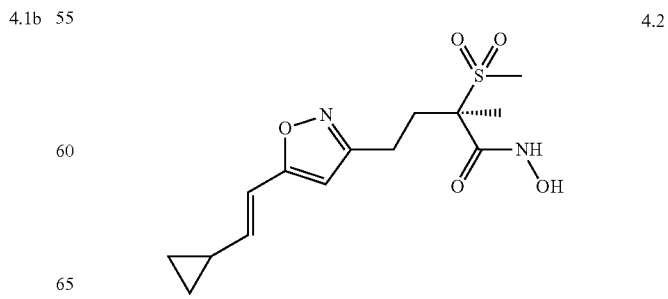

4.2

Step 1: Synthesis of (E)-(4-cyclopropylbut-3-en-1-yn-1-yl)trimethylsilane, (Z)-(4-cyclopropylbut-3-en-1-yn-1-yl)trimethylsilane [4.2a]

To a suspension of triphenyl[3-(trimethylsilyl)prop-2-yn-1-yl]phosphonium bromide (1.4 g, 3.09 mmol) in THF (15 mL) at −78° C. was added n-BuLi (1.360 mL, 2.5 M in heptane, 3.40 mmol) and the resulting reaction mixture was stirred at −78° C. for 45 min. A solution of cyclopropanecarbaldehyde (0.231 mL, 3.09 mmol) in THF (4.0 mL) was added slowly and the mixture was then stirred at −78° C. for 30 min and at rt for 2 hours. The volatile solvent was removed under vacuum. The residue was filtrated through silica gel column and rinsed with heptane. The filtrate was concentrated under vacuum to give product 158 mg (31.1 yield) as mixtures of cis and trans isomers.

Step 2: Synthesis of (R,E)-4-(5-(2-cyclopropylvinyl)isoxazol-3-yl)-N-hydroxy-2-methyl-2-(methylsulfonyl)butanamide [4.2]

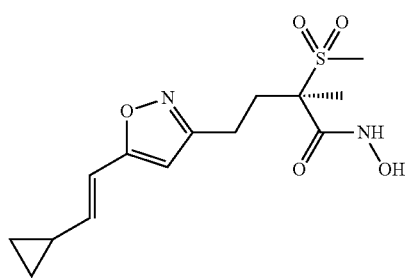

4.2

Compound 4.2 was synthesized following the process of Example 1.15 step 8-10. $^1$H NMR (400 MHz, DMSO-d$_6$): 0.45-0.66 (m, 2H) 0.77-0.94 (m, 2H) 1.46-1.53 (m, 3H) 1.54-1.70 (m, 1H) 1.84-2.10 (m, 2H) 2.26-2.44 (m, 2H) 2.57-2.74 (m, 2H) 3.03 (s, 3H) 5.91-6.07 (m, 1H) 6.26-6.36 (m, 1H) 6.39-6.55 (m, 1H). LCMS (m/z): 329.0 [M+H]$^+$.

IV.3. Synthesis of (R,E)-4-(5-(but-2-en-2-yl)isoxazol-3-yl)-N-hydroxy-2-methyl-2-(methylsulfonyl)butanamide [4.3-1] and (R,Z)-4-(5-(but-2-en-2-yl)isoxazol-3-yl)-N-hydroxy-2-methyl-2-(methylsulfonyl)butanamide [4.3-2]

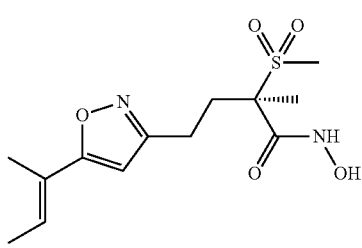

4.3-1

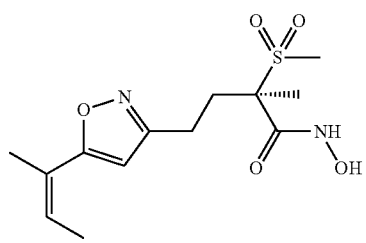

4.3-2

Compound 4.3-1 and 4.3-2 were synthesized following the process of Example 4.1 starting from commercial available 3-methylpent-1-yn-3-ol. The two isomers were separated by reverse phase HPLC.

4.3-1: $^1$H NMR (400 MHz, DMSO-d$_6$): 1.45-1.54 (m, 3H) 1.78 (d, J=7.04 Hz, 3H) 1.85-1.93 (m, 3H) 1.98 (td, J=12.43, 4.82 Hz, 1H) 2.33-2.45 (m, 1H) 2.50-2.57 (m, 1H) 2.59-2.75 (m, 1H) 3.04 (s, 3H) 6.26-6.38 (m, 1H) 6.44 (s, 1H). LCMS (m/z): 317.3 [M+H]$^+$.

4.3-2: $^1$H NMR (400 MHz, DMSO-d$_6$): 1.09 (t, J=7.41 Hz, 3H) 1.43-1.54 (m, 4H) 1.99 (td, J=12.35, 4.89 Hz, 2H) 2.32-2.43 (m, 3H) 2.51-2.60 (m, 1H) 2.61-2.77 (m, 1H) 2.99-3.11 (m, 3H) 5.32 (s, 1H) 5.71 (s, 1H) 6.61 (s, 1H). LCMS (m/z): 317.3 [M+H]$^+$

IV.5 and IV.6. Synthesis of (R,Z)-4-(5-(2-cyclopropyl-1-fluorovinyl)isoxazol-3-yl)-N-hydroxy-2-methyl-2-(methylsulfonyl)butanamide and (R,E)-4-(5-(2-cyclopropyl-1-fluorovinyl)isoxazol-3-yl)-N-hydroxy-2-methyl-2-(methylsulfonyl)butanamide [4.5-1] and [4.5-2]

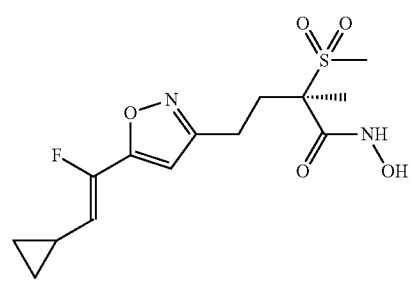

4.5-1

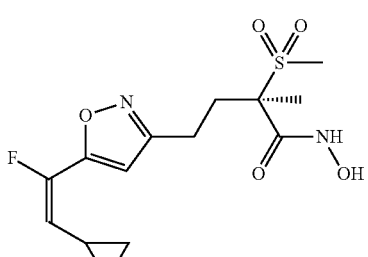

4.5-2

Step 1: Synthesis of (E)-(2-bromo-2-fluorovinyl)cyclopropane [4.5a]

A mixture of cyclopropanecarbaldehyde (0.897 mL, 12 mmol), tribromofluoromethane (1.648 mL, 16.80 mmol) and PPh$_3$ (6.29 g, 24.00 mmol) in THF (7 mL) in a 20 ml microwave vial (20 mL) was sealed and was stirred at 75° C. for 6 hours. The reaction mixture was cooled to ambient temperature and diluted with pentane. The mixture was filtered and the volatile solvent was removed carefully under vacuum to give product as a light yellow solution in THF. The product is a mixture of trans/cis isomer.

Step 2: synthesis of (4-cyclopropyl-3-fluorobut-3-en-1-yn-1-yl)trimethylsilane [4.5b]

To a mixture of 4.5a (0.5 g, 3.03 mmol), CuI (0.029 g, 0.152 mmol) and PdCl$_2$(PPh$_3$)$_2$ (0.053 g, 0.076 mmol) was added ethynyltrimethylsilane (0.476 g, 4.85 mmol) and Et$_3$N (2.71 mL, 21.21 mmol). The resulting mixture was sealed and was stirred at 25° C. for 16 hours. The volatile solvent was then removed in vacuo and to the residue was added DCM. The mixture was filtered and the filtrate was concentrated. The crude product was used at the next step with no further purification.

Step 3. Synthesis of (R,Z)-4-(5-(2-cyclopropyl-1-fluorovinyl)isoxazol-3-yl)-N-hydroxy-2-methyl-2-(methylsulfonyl)butanamide and (R,E)-4-(5-(2-cyclopropyl-1-fluorovinyl)isoxazol-3-yl)-N-hydroxy-2-methyl-2-(methylsulfonyl)butanamide [4.5-1] and [4.5-2]

Compound 4.5 was synthesized following the process of Example 1.15 step 8-10. The crude product was purified by reverse phase Prep HPLC to give pure isomers 4.5-1 and 4.5-2.

4.5-1: $^1$H NMR (400 MHz, CD$_3$CN): 0.49-0.60 (m, 4H) 0.89-1.03 (m, 4H) 1.61 (t, J=3.99 Hz, 7H) 2.00-2.10 (m, 2H) 2.10-2.27 (m, 4H) 2.51-2.70 (m, 8H) 2.72-2.90 (m, 3H) 2.93-3.04 (m, 5H) 5.12-5.34 (m, 2H) 6.36-6.63 (m, 2H). LCMS (m/z): 347.2 [M+H]$^+$ 4.5-2: $^1$H NMR (400 MHz, CD$_3$CN): 0.53-0.70 (m, 3H) 0.88-1.04 (m, 3H) 1.52-1.66 (m, 4H) 1.76-1.90 (m, 2H) 2.05-2.29 (m, 2H) 2.47-2.67 (m, 4H) 2.71-2.86 (m, 2H) 2.91-3.06 (m, 4H) 5.20-5.41 (m, 1H) 6.31-6.45 (m, 1H) 9.58 (br. s., 1H). LCMS (m/z): 347.2 [M+H]$^+$

IV.7 Synthesis of (R,Z)-4-(5-(2-cyclopropyl-2-fluorovinyl)isoxazol-3-yl)-N-hydroxy-2-methyl-2-(methylsulfonyl)butanamide [4.7]

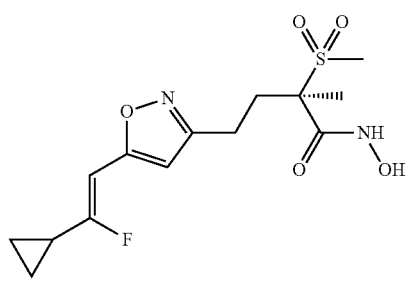

4.7

Step 1. Synthesis of (Z)-(2-bromo-1-fluorovinyl)cyclopropane [4.7a]

To a mixture of NBS (2.3 g, 12.98 mmol) and silver fluoride (3.71 g, 29.5 mmol) in acetonitrile/water (18/1, 19 mL) was added ethynylcyclopropane (780 mg, 11.80 mmol). The resulting mixture was sealed and stirred at 80° C. for 18 hours. The mixture was cooled at room temperature and filtered. To the filtrate was added EtOAc and the solution was filtered again. The filtrate was dried over Na$_2$SO$_4$ and concentrated to give product 1.0 g (51.4 yield). The crude material was used in the next step with no further purification. $^1$H NMR (500 MHz, CDCl$_3$): 0.72-0.84 (m, 4H) 1.60 (d, J=18.29 Hz, 1H) 5.16-5.43 (m, 1H).

Step 2: Synthesis of (Z)-(4-cyclopropyl-4-fluorobut-3-en-1-yn-1-yl)trimethylsilane [4.7b]

To a mixture of Ph$_3$P (0.079 g, 0.303 mmol), CuI (0.058 g, 0.303 mmol) and PdCl$_2$(PPh$_3$)$_2$ (0.106 g, 0.152 mmol) was added acetonitrile (8 mL), (Z)-(2-bromo-1-fluorovinyl)cyclopropane (0.5 g, 3.03 mmol) and ethynyltrimethylsilane (0.476 g, 4.85 mmol), followed by Et$_3$N (1.356 mL, 10.61 mmol). The resulting mixture was sealed and stirred at 70° C. for 10 hours. The mixture was cooled ambient temperature and the volatile solvent was removed in vacuo. The crude material was purified by silica column chromatography with DCM as elute to give product 0.552 g (100% yield). $^1$H NMR (500 MHz, CDCl$_3$): 0.15-0.32 (m, 9H) 0.75-0.92 (m, 4H) 1.58 (s, 1H) 4.72-5.04 (m, 1H)

Step 3. Synthesis of (R,Z)-4-(5-(2-cyclopropyl-2-fluorovinyl)isoxazol-3-yl)-N-hydroxy-2-methyl-2-(methylsulfonyl)butanamide [4.7]

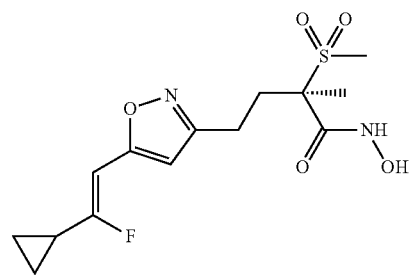

4.7

Compound 4.7 was synthesized following the process of Example 1.15 step 8-10. $^1$H NMR (400 MHz, DMSO-d6): 0.75-0.97 (m, 4H) 1.49 (s, 3H) 1.77-2.07 (m, 2H) 2.33-2.57 (m, 2H) 2.59-2.76 (m, 1H) 3.03 (s, 3H) 5.99-6.25 (m, 1H) 6.42 (d, J=1.66 Hz, 1H) 10.93 (br. s., 1H). LCMS (m/z): 347.2 [M+H]$^+$.

IV.8. Synthesis of (R)-4-(5-(cyclohex-1-en-1-yl)isoxazol-3-yl)-N-hydroxy-2-methyl-2-(methylsulfonyl)butanamide [4.8]

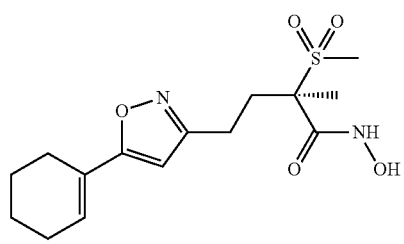

4.8

Compound 4.8 was synthesized following the process of Example 1.1 method B from 1-ethynylcyclohex-1-ene. $^1$H NMR (500 MHz, DMSO-d$_6$): (t, J=4.0 Hz, 1H), 6.44 (s, 1H), 3.06 (s, 3H), 2.77-2.62 (m, 1H), 2.60-2.36 (m, 7H), 2.33-2.14 (m, 4H), 2.00 (td, J=12.5, 4.9 Hz, 1H), 1.78-1.56 (m, 4H), 1.52 (s, 3H). LCMS (m/z): 343.3 [M+H]$^+$.

Pharmaceutical Activity

P. aeruginosa LpxC Inhibition Assay

The P. aeruginosa LpxC protein is produced according to the general method of Hyland et al (Journal of Bacteriology 1997 179, 2029-2037: Cloning, expression and purification of UDP-3-O-acyl-GlcNAc deacetylase from Pseudomonas aeruginosa: a metalloamidase of the lipid A biosynthesis pathway). The LC-MS/MS method for quantitation of LpxC product was developed using an Agilent 1200 Capillary HPLC system coupled to an Applied Biosystems MDS Sciex 4000QTRAP mass spectrometer. Both instruments are controlled using the Applied Biosystems MDS Sciex Analyst software. LpxC reaction product (UDP-3-O—(R-3-hydroxyacyl)-glucosamine) was produced by hydrolysis of LpxC substrate catalyzed by P.a. LpxC and purified using reversed phase chromatography on a Phenomenex Luna C18(2) 4.6×50 mm column. An LpxC product calibration curve was generated to evaluate the sensitivity and dynamic range of the LC-MS/MS method. Briefly, compounds are pre-incubated with 1 nM P. aeruginosa LpxC for 30 min. at room temperature. Reactions are initiated by the addition of 2 μM UDP-3-O—(R-3-hydroxydecanoyl)-GlcNAc. Reactions are conducted in a 384-well plate with a total volume of 50 μL in each well containing 50 mM Sodium phosphate pH 7.5, 0.005% Trition X-100 for 20 min at room temperature. After quenching with 1.8% HOAc (5 μL of a 20% HOAc added to each well), reaction mixtures are analyzed using the LC-MS/MS method and peak areas are transformed into product concentration using a LpxC product calibration curve. Total activity (0% inhibition control) is obtained from reactions with no inhibitors and 100% inhibition control is the background using quenched samples before reaction starts. For IC$_{50}$ determinations, peak areas are converted to percent inhibition in Microsoft Excel. Percent inhibition values are plotted vs. log compound concentration using XLfit. Data is fit to the four-parameter logistic equation using the non-linear regression algorithm in XLfit to return the IC$_{50}$ and hill slope values.

Bacterial Screens and Cultures

Bacterial isolates were cultivated from −70° C. frozen stocks by two consecutive overnight passages at 35° C. in ambient air on 5% blood agar (Remel, Lenexa, Kans.). Quality control strain, P. aeruginosa ATCC 27853, A. baumannii ATCC19606 and E. coli ATCC 25922 are from the American Type Culture Collection (ATCC; Rockville, Md.) and PAO1 was received from Dr. K. Poole.

Susceptibility Testing

Minimal Inhibitory Concentrations (MICs) were determined by the broth microdilution method in accordance with Clinical and Laboratories Institute (CLSI) guidelines (CLSI M100-S25, Performance Standards for Antimicrobial Susceptibility Testing; Twenty-fifth Informational Supplement). In brief, fresh bacterial overnight cultures were resuspended in sterile saline, adjusted to a 0.5 McFarland turbidity standard and then diluted 2000-fold in cation adjusted Mueller-Hinton Broth II (MHB; Remel BBL) to yield a final inoculum of approximately 5×10$^5$ colony-forming units (CFU)/mL. Two-fold serial dilutions of compounds were prepared in 100% dimethyl sulfoxide (DMSO) at 100-fold the highest final assay concentration; the resulting dilution series of compounds were diluted 1:10 with sterile water. Ten μl of the drug dilution series in 10% DMSO was transferred to microtiter wells and 90 μl of bacterial suspension was inoculated into the wells. For testing the ability of compounds to potentiate the activity of known antibiotics, the assay was modified as follows; known antibiotics were added to the bacterial inoculum at 1.1-fold the final assay concentration indicated in Table A. All inoculated microdilution trays were incubated in ambient air at 35° C. for 20 hours. Following incubation, assay plates were read in a microtiter plate reader at 600 nm and visually inspected to confirm the MIC endpoint well with the OD value. The lowest concentration of the compound that prevented visible growth was recorded as the MIC. Performance of the assay was monitored by testing ciprofloxacin against the laboratory quality control strain in accordance with guidelines of the CLSI.

The LpxC inhibitory activity for selected compounds of the invention on LpxC from P. aeruginosa are reported in Table A. The MIC assays for P. aeruginosa, E. coli and A. baumannii were also performed in the presence of sub-inhibitory concentrations of rifampicin to demonstrate the potential for synergy with other antimicrobial agents—see Table B.

TABLE A

Biological data for selected compounds of the invention.

| Compound number | P.A. LpxC IC$_{50}$ [μmol l$^{-1}$] |
|---|---|
| 1.1 | 0.003 |
| 1.2 | <0.001 |
| 1.3 | <0.001 |
| 1.4 | 0.002 |
| 1.5 | 0.001 |
| 1.6 | <0.001 |
| 1.7 | <0.001 |
| 1.8 | <0.001 |
| 1.9 | 0.003 |
| 1.10 | <0.001 |
| 1.11 | 0.001 |
| 1.12 | <0.001 |
| 1.13 | NA |
| 1.14 | 0.002 |
| 1.15a | |
| 1.15b | |
| 1.16 | <0.001 |
| 2.1 | <0.001 |
| 2.2 | <0.001 |
| 2.3 | <0.001 |
| 2.4 | <0.001 |
| 2.5 | <0.001 |
| 2.6 | <0.001 |
| 2.7 | <0.001 |
| 2.8 | <0.001 |
| 3.1 | <0.001 |
| 3.2 | <0.001 |
| 3.3 | <0.001 |
| 3.4 | <0.001 |
| 3.5 | 0.003 |
| 3.6 | 0.002 |
| 4.1 | <0.001 |
| 4.2 | |
| 4.3-1 | 0.003 |
| 4.3-2 | |
| 4.5-1 | <0.001 |
| 4.5-2 | |
| 4.7 | <0.001 |
| 4.8 | <0.001 |

TABLE B

Antibacterial Efficacy and Synergy

| Cmpd No. | P.A. PAO1 NB52019 MIC (µg/ml) | E.C. ATCC 25922 MIC (µg/ml) | E.C. ATCC 29522 (+2 µg/ml RIF) MIC (µg/ml) | A.B. ATCC 19606 MIC (µg/ml) | A.B. ATCC 19606 (+2 µg/ml RIF) MIC (µg/ml) |
|---|---|---|---|---|---|
| 1.1 | 0.25 | 2 | ≤0.06 | >64 | 0.125 |
| 1.2 | 0.125 | 2 | ≤0.06 | >64 | ≤0.06 |
| 1.3 | 0.25 | 8 | 2 | >64 | 0.25 |
| 1.4 | 0.25 | 4 | ≤0.06 | >64 | 2 |
| 1.5 | 0.25 | 4 | ≤0.06 | >64 | ≤0.06 |
| 1.6 | 0.5 | 4 | 0.125 | >64 | 0.125 |
| 1.7 | 0.25 | 2 | ≤0.06 | >64 | 0.125 |
| 1.8 | 0.25 | 8 | 0.25 | >64 | ≤0.06 |
| 1.9 | 1 | 32 | 0.125 | >64 | 1 |
| 1.10 | 0.5 | 8 | 0.25 | >64 | 0.25 |
| 1.11 | 1 | 32 | 0.5 | >64 | 1 |
| 1.12 | 0.5 | 16 | 0.25 | >64 | ≤0.06 |
| 1.13 | 0.5 | 16 | 0.25 | >64 | ≤0.06 |
| 1.14 | 8 | >64 | 16 | >64 | ≤0.06 |
| 1.15a | 2 | 8 | 0.25 | >64 | 0.25 |
| 1.15b | 2 | 4 | 0.25 | >64 | 0.5 |
| 1.16 | 2 | 16 | 4 | >64 | 4 |
| 2.1 | 0.5 | 2 | ≤0.06 | >64 | 2 |
| 2.2 | 0.25 | 0.25 | ≤0.06 | >64 | 0.5 |
| 2.3 | 0.5 | 1 | 0.125 | >64 | 4 |
| 2.4 | 0.5 | 0.5 | ≤0.06 | 64 | ≤0.06 |
| 2.5 | 1 | 0.25 | 0.125 | >64 | 0.5 |
| 2.6 | 0.25 | 0.5 | 0.125 | >64 | 1 |
| 2.7 | 0.25 | 1 | 0.125 | >64 | 6 |
| 2.8 | 0.25 | 1 | 0.125 | >64 | 1 |
| 3.1 | 0.5 | 1 | ≤0.06 | >64 | ≤0.06 |
| 3.2 | 1 | 1 | 0.5 | >64 | ≤0.06 |
| 3.3 | 0.25 | ≤0.06 | 0.06 | 64 | ≤0.06 |
| 3.4 | 0.5 | 1 | ≤0.06 | >64 | 0.125 |
| 3.5 | 16 | 16 | 2 | 32 | 1 |
| 3.6 | 4 | 2 | 0.5 | 64 | 0.125 |
| 4.1 | 0.5 | 8 | 0.125 | >64 | 1 |
| 4.2 | 0.25 | 8 | 0.125 | >64 | 0.5 |
| 4.3-1 | 2 | 32 | 0.5 | >64 | 8 |
| 4.3-2 | 2 | 16 | 0.5 | >64 | 8 |
| 4.5-1 | 0.25 | 2 | 0.25 | >64 | 0.25 |
| 4.5-2 | 8 | 64 | 2 | >64 | 16 |
| 4.7 | 0.5 | 8 | 0.5 | >64 | 0.5 |
| 4.8 | 0.25 | 4 | 0.5 | >64 | 1 |

P.A. = *Pseudomonas aeruginosa*
E.C. = *Escherichia coli*
A.B. = *Acinetobacter baumannii*

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A compound of Formula (I):

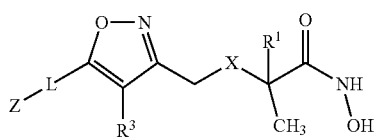

(I)

or a pharmaceutically acceptable salt thereof, wherein:

X is —$CH_2$—, and $R^1$ is —$SO_2R^2$ where $R^2$ is $C_1$-$C_3$ alkyl;

$R^3$ is H or halo;

L is —C≡C— or —$CR^5$=$CR^5$—;

$R^5$ is independently selected at each occurrence from H, halo and methyl;

and

Z is selected from $C_{1-6}$ alkyl, $C_3$-$C_6$ cycloalkyl, pyridinyl, and phenyl, each of which is optionally substituted with up to three groups selected from halogen, hydroxy, $C_{1-4}$ alkoxy, $C_{1-4}$ haloalkoxy, CN, and $C_{1-4}$ alkyl that is optionally substituted with one to three groups selected from halogen, hydroxy, amino, CN, and $C_{1-3}$ alkoxy;

or, when L is —$CR^5$=$CR^5$—, Z taken together with one of the $R^5$ groups and any atoms connecting Z with the $R^5$ group can form a 3-7 membered cycloalkyl or cycloalkenyl group that is optionally substituted with up to three groups selected from halogen, hydroxy, $C_{1-4}$ alkoxy, $C_{1-4}$ haloalkoxy, CN, and $C_{1-4}$ alkyl that is optionally substituted with one to three groups selected from halogen, hydroxy, amino, CN, and $C_{1-3}$ alkoxy.

2. The compound of claim 1, wherein $R^1$ is —$SO_2Me$.
3. The compound of claim 1, wherein $R^3$ is H.
4. The compound of claim 1, wherein L is —C≡C—.
5. The compound of claim 1, wherein Z is phenyl substituted with up to three groups selected from halogen, $C_{1-4}$ alkoxy, $C_{1-4}$ haloalkoxy, CN, and $C_{1-4}$ alkyl optionally substituted with one to three groups selected from halogen, hydroxy, amino, CN, and $C_{1-3}$ alkoxy.

6. The compound of claim 1, wherein Z is $C_1$-$C_4$ alkyl, optionally substituted with up to three groups selected from halogen, $C_{1-4}$ alkoxy, $C_{1-4}$ haloalkoxy, CN, and $C_{1-4}$ alkyl optionally substituted with one to three groups selected from halogen, hydroxy, amino, CN, and $C_{1-3}$ alkoxy.

7. The compound of claim 1, wherein Z is $C_3$-$C_6$ cycloalkyl, optionally substituted with up to three groups selected from halogen, $C_{1-4}$ alkoxy, $C_{1-4}$ haloalkoxy, CN, and $C_{1-4}$ alkyl optionally substituted with one to three groups selected from halogen, hydroxy, amino, CN, and $C_{1-3}$ alkoxy.

8. The compound of claim 7, wherein L is —C≡C—.

9. The compound of claim 1, wherein the compound is of Formula (II):

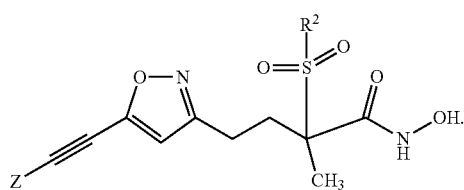

(II)

10. The compound of claim 9, wherein $R^2$ is Me.

11. The compound of claim 1, which is selected from:
   (R)-4-(5-(cyclopropylethynyl)isoxazol-3-yl)-N-hydroxy-2-methyl-2-(methylsulfonyl)butanamide,
   (R)-4-(5-(cyclobutylethynyl)isoxazol-3-yl)-N-hydroxy-2-methyl-2-(methylsulfonyl)butanamide,
   (R)—N-hydroxy-2-methyl-4-(5-(3-methylbut-1-yn-1-yl)isoxazol-3-yl)-2-(methylsulfonyl)butanamide,
   (R)-4-(5-(but-1-yn-1-yl)isoxazol-3-yl)-N-hydroxy-2-methyl-2-(methylsulfonyl)butanamide,
and the pharmaceutically acceptable salts of any of these compounds.

12. A pharmaceutical composition, comprising:
   a compound of claim 11 and
   a pharmaceutically acceptable carrier.

13. A pharmaceutical combination composition, comprising:
   a compound of claim 11,
   an antibacterially effective amount of a second therapeutic agent, and
   a pharmaceutically acceptable carrier.

14. The pharmaceutical combination composition of claim 13, wherein the second therapeutic agent is selected from the group consisting of Ampicillin, Piperacillin, Penicillin G, Ticarcillin, Imipenem, Meropenem, Azithromycin, Erythromycin, Aztreonam, Cefepime, Cefotaxime, Ceftriaxone, Ceftazidime, Ciprofloxacin, Levofloxacin, Clindamycin, Doxycycline, Gentamycin, Amikacin, Tobramycin, Tetracycline, Tigecycline, Rifampicin, Vancomycin and Polymyxin.

15. A method of inhibiting a deacetylase enzyme in a Gram-negative bacterium, comprising contacting the Gram-negative bacteria with the compound of claim 11.

16. A method for treating a subject with a Gram-negative bacterial infection, comprising:
   administering to the subject in need thereof an antibacterially effective amount of the compound of claim 11.

17. The method of claim 16, wherein the Gram negative bacterial infection is an infection comprising at least one bacterium selected from the group consisting of
   *Pseudomonas aeruginosa* and other *Pseudomonas* spp., *Stenotrophomonas maltophilia*, *Burkholderia cepacia* and other *Burkholderia* spp., *Alcaligenes xylosoxidans*, *Acinetobacter* spp., *Achromobacter* spp., *Aeromonas* spp., *Enterobacter* spp., *Eschericia coli*, *Haemophilus* spp., *Klebsiella* spp., *Moraxella* spp., *Bacteroides* spp., *Francisella* spp., *Shigella* spp., *Proteus* spp., *Porphyromonas* spp., *Prevotella* spp., *Mannheimia haemolyiticus*, *Pastuerella* spp., *Providencia* spp., *Vibrio* spp., *Salmonella* spp., *Bordetella* spp., *Borrelia* spp., *Helicobacter* spp., *Legionella* spp., *Citrobacter* spp., *Cedecea* spp., *Serratia* spp., *Campylobacter* spp., *Yersinia* spp., *Fusobacterium* spp., and *Neisseria* spp.

18. The method of claim 17, wherein the bacterium is an Enterobacteriaceae which is selected the group consisting of *Pseudomonas*, *Acinetobacter*, *Stenotrophomonas*, *Burkholderia*, *Serratia*, *Proteus*, *Klebsiella*, *Enterobacter*, *Citrobacter*, *Salmonella*, *Shigella*, *Providencia*, *Morganella*, *Cedecea*, *Yersina* and *Edwardsiella* species and *Escherichia coli*.

19. The method of claim 17, wherein the bacterium is *Pseudomonas aeruginosa*.

* * * * *